United States Patent
Conte et al.

(10) Patent No.: US 7,678,818 B2
(45) Date of Patent: Mar. 16, 2010

(54) ANTHRANILAMIDE AND 2-AMINO-HETEROARENE-CARBOXAMIDE COMPOUNDS

(75) Inventors: Aurelia Conte, Basel (CH); Holger Kuehne, Grenzach-Wyhlen (DE); Thomas Luebbers, Loerrach (DE); Patrizio Mattei, Riehen (CH); Cyrille Maugeais, Mulhouse (FR); Werner Mueller, Aesch BL (CH); Philippe Pflieger, Schwoben (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 553 days.

(21) Appl. No.: 11/655,538

(22) Filed: Jan. 19, 2007

(65) Prior Publication Data

US 2007/0219261 A1    Sep. 20, 2007

(30) Foreign Application Priority Data

Feb. 7, 2006    (EP) .................................. 06101366

(51) Int. Cl.
*A61K 31/44* (2006.01)
*C07D 213/02* (2006.01)

(52) U.S. Cl. .................. 514/357; 546/329; 564/305; 514/372; 514/396; 514/406; 548/206; 548/300.1; 548/356.1; 548/400; 548/950

(58) Field of Classification Search .......... 546/329; 564/305; 514/357, 372, 396, 406; 548/206, 548/300.1, 356.1, 400, 950
See application file for complete search history.

(56) References Cited

U.S. PATENT DOCUMENTS 4,353,827 A    10/1982    Hunkeler et al.

7,332,608 B2 *    2/2008    Brendel et al. .............. 546/300

FOREIGN PATENT DOCUMENTS

EP    0 059 391        9/1982
EP    0 987 251 B1    3/2000

OTHER PUBLICATIONS

Le Goff et al., Pharmacology & Therapeutics, 101, pp. 17-38 (2004).
Okamoto et al., Nature, 406, pp. 203-207 (2000).
Applequist et al., J. Org. Chem., 41, pp. 2262-2266 (1976).
Lunt, E., et al., Journal of Medicinal Chemistry, vol. 30, No. 2, pp. 357-366 (1987), XP001069005.

* cited by examiner

*Primary Examiner*—Golam M Shameem
(74) *Attorney, Agent, or Firm*—George W. Johnston; Dennis P. Tramaloni; Brian C. Remy

(57) ABSTRACT

Compounds of formula I

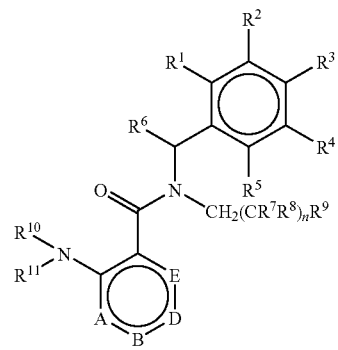

processes for their preparation, their use as pharmaceuticals and to pharmaceutical compositions comprising them.

20 Claims, No Drawings

ANTHRANILAMIDE AND 2-AMINO-HETEROARENE-CARBOXAMIDE COMPOUNDS

PRIORITY TO RELATED APPLICATIONS

This application claims the benefit of European Application No. 06101366.0, filed Feb. 7, 2006, which is hereby incorporated by reference in its entirety.

The present invention relates to novel anthranilamide and 2-amino-heteroarene-carboxamide derivatives, processes for their preparation, their use as pharmaceuticals and to pharmaceutical compositions comprising them.

More particularly, the present invention provides in a first aspect a compound of formula I

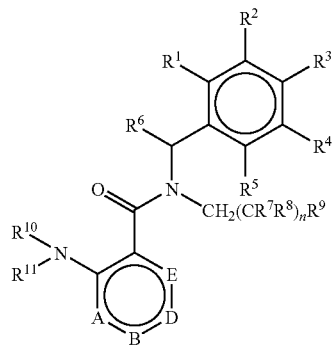

wherein $R^1$, $R^2$, $R^4$ and $R^5$ are independently hydrogen, $C_1$-$C_6$alkyl, $C_1$-$C_6$alkoxy or halogen;

$R^3$ is $C_1$-$C_6$alkyl, halogen-$C_1$-$C_6$alkyl, $C_3$-$C_6$cycloalkyl, Si($C_1$-$C_6$alkyl)$_3$, —$OR^{12}$, wherein $R^{12}$ is $C_1$-$C_6$alkyl, halogen-$C_1$-$C_6$alkyl, $C_3$-$C_6$cycloalkyl, phenyl, benzyl or S(O)$_2$—$C_1$-$C_6$alkyl, or pentafluorosulfuranyl; or $R^2$ and $R^3$ taken together with the carbon atoms they are attached to form a 5- or 6-membered carbocyclic ring or a 5- or 6-membered heterocyclic ring containing one or two heteroatoms selected from N, O or S;

$R^6$ is hydrogen or $C_1$-$C_6$alkyl;

$R^7$ and $R^8$ are independently hydrogen, $C_1$-$C_6$alkyl, hydroxy or halogen;

$R^9$ is hydrogen, $C_1$-$C_6$alkyl, $C_2$-$C_6$alkenyl, halogen-$C_1$-$C_6$alkyl, heterocyclyl, heteroaryl, phenyl, naphthyl, —$OR^{13}$, wherein $R^{13}$ is $C_1$-$C_6$alkyl or phenyl, —$NR^{14}R^{15}$, wherein $R^{14}$ and $R^{15}$ independently are hydrogen, $C_1$-$C_6$alkyl or phenyl, or —C(O)—$OR^{16}$, wherein $R^{16}$ is hydrogen or $C_1$-$C_6$alkyl;

$R^{10}$ and $R^{11}$ are independently hydrogen, halogen, $C_1$-$C_6$alkyl, COR wherein R is $C_1$-$C_6$alkyl, $C_1$-$C_6$alkoxy or $C_3$-$C_6$cycloalkyl, S(O)$_2$—$C_1$-$C_6$alkyl, $C_3$-$C_6$cycloalkyl, or phenyl; or together are $C_1$-$C_6$alkylene;

A is $CR^{17}$ or N, wherein $R^{17}$ is hydrogen, halogen, $C_1$-$C_6$alkyl, $C_1$-$C_6$alkoxy or $C_2$-$C_6$alkenyl;

B is $CR^{18}$ or N, wherein $R^{18}$ is hydrogen, halogen, $C_1$-$C_6$alkyl, $C_1$-$C_6$alkoxy or $C_2$-$C_6$alkenyl;

D is $CR^{19}$ or N, wherein $R^{19}$ is hydrogen, halogen, $C_1$-$C_6$alkyl, $C_1$-$C_6$alkoxy, $C_2$-$C_6$alkenyl or phenyl;

E is $CR^{20}$ or N, wherein $R^{20}$ is hydrogen, halogen, $C_1$-$C_6$alkyl, $C_1$-$C_6$alkoxy or $C_2$-$C_6$alkenyl; or E is $CR^{20}$ and -A-B-D- is —N—O—, —$NR^{21}$—N—, —S—N—, —S—CH— or —CH—S—, wherein $R^{21}$ is hydrogen, halogen, $C_1$-$C_6$alkyl, $C_1$-$C_6$alkoxy or $C_2$-$C_6$alkenyl; or E is N and -A-B-D- is —N—O—, —S—N—, —S—CH—, —CH—CH— or —CH—S—; or E is S and -A-B-D- is —CH—CH—; and n is 1, 2 or 3;

and all pharmaceutically acceptable salts thereof.

The compounds of formula I may bear substituents within their structure, e.g. may bear appropriate alkyl, alkylene or phenyl substituents, e.g. alkyl and alkylene may be substituted by one to thirteen substituents selected from hydroxy, halogen, $C_3$-$C_6$cycloalkyl, cyano, COOH, COOC$_1$-$C_6$alkyl and $C_1$-$C_6$alkoxy; phenyl may be substituted by one to five groups independently selected from $C_1$-$C_6$alkyl, $C_1$-$C_6$alkoxy, halogen-$C_1$-$C_6$alkyl, halogen-$C_1$-$C_6$alkoxy, amino and halogen.

Phenyl and heteroaryl may be annulated with a saturated or unsaturated moiety to form a bicyclic group.

Examples for alkyl, alone or in combination with other groups, include branched or straight-chain monovalent saturated aliphatic hydrocarbon radicals of one to six carbon atoms, e.g. methyl, ethyl, propyl, isopropyl, butyl, isobutyl, tert-butyl, the isomeric pentyls and the isomeric hexyls.

Examples for alkenyl, alone or in combination, include straight-chain or branched hydrocarbon radicals comprising an olefinic bond and up to 6, e.g., up to 4 carbon atoms, e.g. ethenyl, 1-propenyl, 2-propenyl, isopropenyl, 1-butenyl, 2-butenyl, 3-butenyl and isobutenyl. Examples for aryl include phenyl and naphthyl.

Examples for amino include amino, alkylamino, cycloalkylamino, dialkylamino, hydroxyalkylamino, carboxyalkylamino, acylamino, sulfonylamino, acetidin-1-yl and pyrrolidin-1-yl. Heterocyclic groups may be saturated or unsaturated and may contain one or more additional heteroatoms, e.g. nitrogen, oxygen or sulfur.

Examples for an unsaturated heterocyclic group include a heteroaryl group like pyridinyl, pyridazinyl, pyrimidinyl, thiazolyl, oxazolyl, isothiazolyl, isoxazolyl, thiophenyl, furanyl, pyrazolyl, e.g. aminopyridinyl, aminopyridazinyl, aminopyrimidinyl, aminothiophenyl, aminopyrazolyl, aminothiazolyl, aminoisothiazolyl, aminoisoxazolyl, e.g. 2-aminopyridin-3-yl, 3-aminopyridin-2-yl, 4-aminopyridin-3-yl, 3-aminopyridin-4-yl, 3-aminopyrazin-2-yl, 4-aminopyridazin-3-yl, 5-aminopyridazin-4-yl, 3-aminopyridazin-4-yl, 4-aminopyrimidin-5-yl, 5-aminopyrimidin-4-yl, 5-aminothiazol-4-yl, 5-aminoisothiazol-4-yl and 3-aminoisoxazol-4-yl, 2-aminothiophen-3-yl, 3-aminothiophen-2-yl, 3-aminothiophen-4-yl, 5-aminopyrazol-4-yl and may be unsubstituted or substituted by one to three substituents selected from halogen, alkyl, halogenalkyl, cycloalkyl which may again be unsubstituted or substituted by one or more of the above mentioned substituents.

Examples for halogen include fluorine, chlorine, bromine, iodine.

The term halogen-$C_1$-$C_6$alkyl refers to $C_1$-$C_6$alkyl groups as defined above wherein at least one of the hydrogen atoms of the $C_1$-$C_6$alkyl group is replaced by a halogen atom, e.g.

fluoro or chloro. Examples of halogenated $C_1$-$C_6$alkyl groups include trifluoromethyl, difluoromethyl, fluoromethyl and chlorodifluoromethyl.

The term halogen-$C_1$-$C_6$alkoxy refers to $C_1$-$C_6$alkoxy groups as defined above wherein at least one of the hydrogen atoms of the $C_1$-$C_6$alkoxy group is replaced by a halogen atom, e.g. fluoro or chloro. Examples of halogenated $C_1$-$C_6$alkyl groups include trifluoromethoxy, difluoromethoxy, fluoromethoxy and chlorodifluoromethoxy.

The term $C_1$-$C_6$alkoxy-halogen-$C_1$-$C_6$alkyl refers to halogen-$C_1$-$C_6$alkyl groups as defined above wherein at least one of the hydrogen atoms of the halogen-$C_1$-$C_6$alkyl group is replaced by an alkoxy group. An example of a $C_1$-$C_6$alkoxy-halogen-$C_1$-$C_6$alkyl group is 2,2,2-trifluoro-1-methoxy-1-trifluoromethyl-ethyl.

Compounds of the invention exist in free or salt, e.g. acid addition salt form. The invention is to be understood as including the compounds of formula I in free as well as in salt form, e.g. as hydrochloride, sulfate or sodium salt.

In one embodiment the present invention provides a compound of formula I wherein $R^1$ is hydrogen or halogen. In another embodiment the present invention provides a compound of formula I wherein $R^1$ is hydrogen or chlorine. In still another embodiment the present invention provides a compound of formula I wherein $R^1$ is hydrogen.

In one embodiment the present invention provides a compound of formula I wherein $R^2$ is hydrogen or halogen. In another embodiment the present invention provides a compound of formula I wherein $R^2$ is hydrogen, fluorine or chlorine. In still another embodiment the present invention provides a compound of formula I wherein $R^2$ is hydrogen.

In one embodiment the present invention provides a compound of formula I wherein $R^3$ is $C_1$-$C_6$alkyl, halogen-$C_1$-$C_6$alkyl, $C_3$-$C_6$cycloalkyl, $C_3$-$C_6$cycloalkyl which is substituted by one to eleven halogen or $C_1$-$C_6$alkoxy, $Si(C_1$-$C_6$alkyl$)_3$, —$OR^{12}$, wherein $R^{12}$ is $C_1$-$C_6$alkyl which is unsubstituted or substituted by one to six substituents selected from halogen, $COOC_1$-$C_6$alkyl, hydroxy, $C_3$-$C_6$cycloalkyl and phenyl which is unsubstituted or substituted by halogen or cyano; phenyl; or $S(O)_2$—$C_1$-$C_6$alkyl; or pentafluorosulphuranyl. In another embodiment the present invention provides a compound of formula I wherein $R^3$ is $C_1$-$C_6$alkyl, halogen-$C_1$-$C_6$alkyl, $C_3$-$C_6$cycloalkyl, $C_3$-$C_6$cycloalkyl which is substituted by one to eleven halogen or $C_1$-$C_6$alkoxy, —$OR^{12}$, wherein $R^{12}$ is $C_1$-$C_6$alkyl which is unsubstituted or substituted by one to six substituents selected from halogen, hydroxy and $C_3$-$C_6$cycloalkyl; phenyl; or $S(O)_2$—$C_1$-$C_6$alkyl; or pentafluorosulphuranyl. In still another embodiment the present invention provides a compound of formula I wherein $R^3$ is $C_1$-$C_6$alkyl, halogen-$C_1$-$C_6$alkyl, $C_3$-$C_6$cycloalkyl, $C_3$-$C_6$cycloalkyl which is substituted by one to eleven halogen or $C_1$-$C_6$alkoxy, —$OR^{12}$, wherein $R^{12}$ is $C_1$-$C_6$alkyl which is unsubstituted or substituted by one to six halogen. In still another embodiment the present invention provides a compound of formula I wherein $R^3$ is $CH_3$, $CH_2CH_3$, $C(CH_3)_3$, $CH(CH_3)_2$, $CF_3$, $CF(CF_3)_2$, $CF_2CF_3$, cyclopropyl, cyclobutyl, cyclopentyl, 1-fluorocyclopropyl, 1-fluorocyclobutyl, 1-methoxycyclopropyl, 1-methoxycyclobutyl, $OC(CH_3)_3$, $OCF_3$, $OCF_2CHF_2$, $OCH_2COOCH_3$, $OCH_2CH(OH)CF_3$, $OCH_2$cyclopropyl, O-4-fluorobenzyl, O-4-cyanobenzyl, phenoxy, $OS(O)_2CH_3$, $Si(CH_3)_3$ or $SF_5$. In still another embodiment the present invention provides a compound of formula I wherein $R^3$ is $CH_3$, $CH_2CH_3$, $C(CH_3)_3$, $CF_3$, $CF(CF_3)_2$, $CF_2CF_3$, cyclopropyl, cyclobutyl, cyclopentyl, 1-fluorocyclopropyl, 1-fluorocyclobutyl, 1-methoxycyclopropyl, 1-methoxycyclobutyl, $OC(CH_3)_3$, $OCF_3$ or $OCF_2CHF_2$. In another embodiment the present invention provides a compound of formula I wherein $R^3$ is unsubstituted $C_1$-$C_6$alkyl, $C_1$-$C_6$alkyl which is substituted by halogen or unsubstituted $C_3$-$C_6$cycloalkyl. In still another embodiment the present invention provides a compound of formula I wherein $R^3$ is $CH_3$, $CH_2CH_3$, $C(CH_3)_3$, $CH(CH_3)_2$, $CF_3$, $CF(CF_3)_2$, $CF_2CF_3$, cyclopropyl, cyclobutyl or cyclopentyl.

In one embodiment the present invention provides a compound of formula I wherein $R^4$ is hydrogen.

In one embodiment the present invention provides a compound of formula I wherein $R^5$ is hydrogen.

In one embodiment the present invention provides a compound of formula I wherein $R^6$ is hydrogen.

In one embodiment the present invention provides a compound of formula I wherein $R^7$ is hydrogen, hydroxy or halogen.

In one embodiment the present invention provides a compound of formula I wherein $R^8$ is hydrogen, hydroxy or halogen.

In one embodiment the present invention provides a compound of formula I wherein $R^7$ is hydrogen or halogen and $R^8$ is hydrogen, hydroxy or halogen. In another embodiment the present invention provides a compound of formula I wherein $R^7$ is hydrogen and $R^8$ is hydrogen or $R^7$ is hydrogen and $R^8$ is hydroxy or halogen. In another embodiment the present invention provides a compound of formula I wherein $R^7$ is halogen and $R^8$ is halogen.

In one embodiment the present invention provides a compound of formula I wherein $R^9$ is hydrogen, heteroaryl which is unsubstituted or substituted by one to five substituents selected from halogen, $C_1$-$C_6$alkyl, halogen-$C_1$-$C_6$alkyl and phenyl, phenyl which is unsubstituted or substituted by one to five substituents selected from halogen, $C_1$-$C_6$alkyl, halogen-$C_1$-$C_6$alkyl and halogen-$C_1$-$C_6$alkoxy, naphthyl, —$OR^{13}$, wherein $R^{13}$ is $C_1$-$C_6$alkyl or phenyl, or —$NR^4R^5$, wherein $R^{14}$ and $R^{15}$ independently are hydrogen, $C_1$-$C_6$alkyl or phenyl which is unsubstituted or substituted by halogen. In another embodiment the present invention provides a compound of formula I wherein $R^9$ is hydrogen, heteroaryl which is substituted by one to three substituents selected from halogen, $C_1$-$C_6$alkyl, halogen-$C_1$-$C_6$alkyl and phenyl, phenyl which is unsubstituted or substituted by one to three substituents selected from halogen, $C_1$-$C_6$alkyl, halogen-$C_1$-$C_6$alkyl and halogen-$C_1$-$C_6$alkoxy, naphthyl, —$OR^{13}$, wherein $R^{13}$ is phenyl, or —$NR^{14}R^{15}$, wherein $R^{14}$ and $R^{15}$ independently are hydrogen, $C_1$-$C_6$alkyl or phenyl which is substituted by halogen.

In one embodiment the present invention provides a compound of formula I wherein $R^9$ is heteroaryl selected from

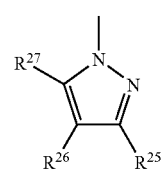

(a)

-continued

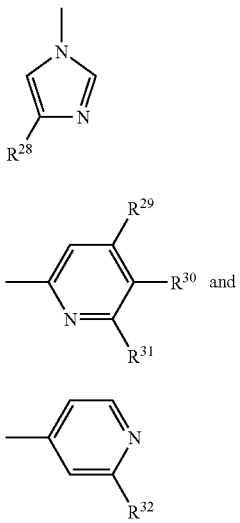

wherein $R^{25}$, $R^{26}$ and $R^{27}$ independently are hydrogen, halogen, $C_1$-$C_6$alkyl, halogen-$C_1$-$C_6$alkyl or phenyl, $R^{28}$ and $R^{32}$ are hydrogen, halogen, $C_1$-$C_6$alkyl, halogen-$C_1$-$C_6$alkyl or phenyl, and $R^{29}$, $R^{30}$ and $R^{31}$ independently are hydrogen, halogen, $C_1$-$C_6$alkyl, halogen-$C_1$-$C_6$alkyl or phenyl.

In another embodiment the present invention provides a compound of formula I wherein $R^9$ is

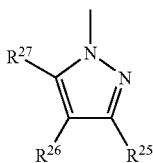

(a)

wherein $R^{25}$ is hydrogen, $C_1$-$C_6$alkyl, halogen-$C_1$-$C_6$alkyl or phenyl;

$R^{26}$ is hydrogen or halogen;

$R^{27}$ is hydrogen, $C_1$-$C_6$alkyl or halogen-$C_1$-$C_6$alkyl.

In another embodiment the present invention provides a compound of formula I wherein $R^9$ is

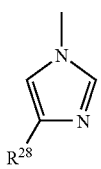

(b)

wherein $R^{28}$ is halogen-$C_1$-$C_6$alkyl.

In another embodiment the present invention provides a compound of formula I wherein $R^9$ is

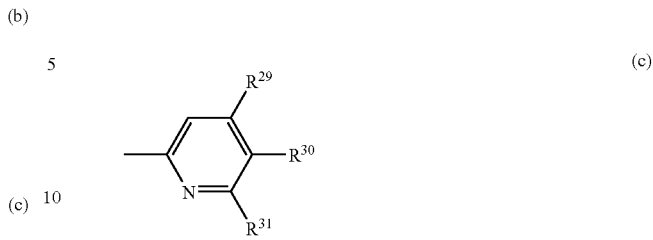

(c)

wherein $R^{29}$ is hydrogen or halogen-$C_1$-$C_6$alkyl;

$R^{30}$ is hydrogen, halogen or halogen-$C_1$-$C_6$alkyl; and $R^{31}$ is hydrogen or halogen-$C_1$-$C_6$alkyl.

In another embodiment the present invention provides a compound of formula I wherein $R^9$ is

(d)

wherein $R^{32}$ is halogen.

In one embodiment the present invention provides a compound of formula I wherein $R^9$ is hydrogen.

In one embodiment the present invention provides a compound of formula I wherein $R^9$ is phenyl which is unsubstituted or substituted by one to five substituents selected from halogen, $C_1$-$C_6$alkyl, halogen-$C_1$-$C_6$alkyl and halogen-$C_1$-$C_6$alkoxy. In another embodiment the present invention provides a compound of formula I wherein $R^9$ is phenyl which is unsubstituted or substituted by one to three substituents selected from halogen, $C_1$-$C_6$alkyl, halogen-$C_1$-$C_6$alkyl and halogen-$C_1$-$C_6$alkoxy.

In still another embodiment the present invention provides a compound of formula I wherein $R^9$ is a group

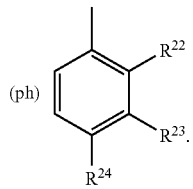

(ph)

wherein $R^{22}$, $R^{23}$ and $R^{24}$ independently are hydrogen, halogen, $C_1$-$C_6$alkyl, halogen-$C_1$-$C_6$alkyl or halogen-$C_1$-$C_6$alkoxy. In still another embodiment the present invention provides a compound of formula I wherein $R^9$ is a group (ph) wherein $R^{22}$ is hydrogen or halogen; $R^{23}$ is hydrogen, halogen, halogen-$C_1$-$C_6$alkyl or halogen-$C_1$-$C_6$alkoxy; and $R^{24}$ is hydrogen, halogen, $C_1$-$C_6$alkyl, halogen-$C_1$-$C_6$alkyl or halogen-$C_1$-$C_6$alkoxy. In still another embodiment the present invention provides a compound of formula I wherein $R^9$ is a group (ph) wherein $R^{22}$ is hydrogen; $R^{23}$ is hydrogen, halogen-$C_1$-$C_6$alkyl or halogen-$C_1$-$C_6$alkoxy; and $R^{24}$ is hydrogen or $C_1$-$C_6$alkyl.

In one embodiment the present invention provides a compound of formula I wherein $R^9$ is naphthyl.

In one embodiment the present invention provides a compound of formula I wherein $R^9$ is —$OR^{13}$, wherein $R^{13}$ is $C_1$-$C_6$alkyl or phenyl. In another embodiment the present invention provides a compound of formula I wherein $R^9$ is —$OR^{13}$, wherein $R^{13}$ is phenyl. In one embodiment the present invention provides a compound of formula I wherein $R^9$ is —$NR^{14}R^{15}$, wherein $R^{14}$ and $R^{15}$ independently are hydrogen, $C_1$-$C_6$alkyl or phenyl which is unsubstituted or substituted by halogen. In another embodiment the present invention provides a compound of formula I wherein $R^9$ is —$NR^{14}R^{15}$, wherein $R^{14}$ and $R^{15}$ independently are hydrogen, $C_1$-$C_6$alkyl or phenyl which is substituted by halogen.

In one embodiment the present invention provides a compound of formula I wherein $R^{10}$ is hydrogen, $C_1$-$C_6$alkyl, $C_1$-$C_6$alkyl which is substituted by hydroxy, cyano, $C_3$-$C_6$cycloalkyl, COOH or COO—$C_1$-$C_6$alkyl; COR wherein R is $C_1$-$C_6$alkyl, halogen-$C_1$-$C_6$alkyl, $C_1$-$C_6$alkoxy or $C_3$-$C_6$cycloalkyl; $S(O)_2$—$C_1$-$C_6$alkyl or $C_3$-$C_6$cycloalkyl. In another embodiment the present invention provides a compound of formula I wherein $R^{10}$ is hydrogen, unsubstituted $C_1$-$C_6$alkyl, $C_1$-$C_6$alkyl which is substituted by cyano; COR wherein R is $C_1$-$C_6$alkyl; or $C_3$-$C_6$cycloalkyl. In still another embodiment the present invention provides a compound of formula I wherein $R^{10}$ is unsubstituted $C_1$-$C_6$alkyl.

In one embodiment the present invention provides a compound of formula I wherein $R^{11}$ is hydrogen or $C_1$-$C_6$alkyl. In another embodiment the present invention provides a compound of formula I wherein $R^{11}$ is hydrogen.

In one embodiment the present invention provides a compound of formula I wherein $R^{10}$ and $R^{11}$ together are $C_1$-$C_6$alkylene which is unsubstituted or substituted by hydroxy.

In one embodiment the present invention provides a compound of formula I wherein E is $CR^{20}$ and -A-B-D- is —$CR^{17}$—$CR^{18}$—$CR^{19}$—, —N—$CR^{18}$—$CR^{19}$—, —$CR^{17}$—N—$CR^{19}$—, —$CR^{17}$—$CR^{18}$—N—, —N—$CR^{18}$—N—, —N—N—$CR^{19}$—, —N—O—, —$NR^{21}$—N—, —S—N—, —S—CH— or —CH—S—, wherein $R^{17}$, $R^{18}$ and $R^{20}$ independently are hydrogen, halogen, $C_1$-$C_6$alkyl, $C_1$-$C_6$alkoxy or $C_2$-$C_6$alkenyl, and $R^{19}$ is hydrogen, halogen, $C_1$-$C_6$alkyl, $C_1$-$C_6$alkoxy, $C_2$-$C_6$alkenyl or phenyl. In another embodiment the present invention provides a compound of formula I wherein E is $CR^{20}$ and -A-B-D- is —$CR^{17}$—$CR^{18}$—$CR^{19}$—, —N—$CR^{18}$—$CR^{19}$—, —$CR^{17}$—N—$CR^{19}$—, —$CR^{17}$—$CR^{18}$—N—, —N—$CR^{18}$—N—, —N—N—$CR^{19}$—, —N—O—, —$NR^{21}$—N—, —S—N— or —S—CH—, wherein $R^{17}$ is hydrogen, halogen or $C_1$-$C_6$alkyl; $R^{18}$ is hydrogen; $R^{19}$ is hydrogen, halogen, $C_1$-$C_6$alkyl, halogen-$C_1$-$C_6$alkyl, $C_1$-$C_6$alkoxy, $C_2$-$C_6$alkenyl or phenyl; $R^{20}$ is hydrogen, halogen or $C_1$-$C_6$alkyl; and $R^{21}$ is $C_1$-$C_6$alkyl.

In still another embodiment the present invention provides a compound of formula I wherein E is $CR^{20}$ and -A-B-D- is —$CR^{17}$—$CR^{18}$—$CR^{19}$—, —N—$CR^{18}$—$CR^{19}$—, —$CR^{17}$—N—$CR^{19}$—, —N—$CR^{18}$—N—, —N—N—$CR^{19}$—, —S—N— or —S—CH—, wherein $R^{17}$ is hydrogen or halogen; $R^{18}$ is hydrogen; $R^{19}$ is hydrogen, halogen, $C_1$-$C_6$alkyl, halogen-$C_1$-$C_6$alkyl or $C_2$-$C_6$alkenyl; and $R^{20}$ is hydrogen or halogen.

In one embodiment the present invention provides a compound of formula I wherein E is N and -A-B-D- is —$CR^{17}$—$CR^{18}$—$CR^{19}$—, —N—$CR^{18}$—$CR^{19}$—, —$CR^{17}$—N—$CR^{19}$—, —N—O—, —S—N—, —S—CH—, —CH—CH— or —CH—S—, wherein $R^{17}$, $R^{18}$ and $R^{20}$ independently are hydrogen, halogen, $C_1$-$C_6$alkyl, $C_1$-$C_6$alkoxy or $C_2$-$C_6$alkenyl, and $R^{19}$ is hydrogen, halogen, $C_1$-$C_6$alkyl, $C_1$-$C_6$alkoxy, $C_2$-$C_6$alkenyl or phenyl. In another embodiment the present invention provides a compound of formula I wherein E is N and -A-B-D- is —$CR^{17}$—$CR^{18}$—$CR^{19}$—, —N—$CR^{18}$—$CR^{19}$—, —$CR^{17}$—N—$CR^{19}$— or —S—N—, wherein $R^{17}$ is hydrogen or halogen; $R^{18}$ is hydrogen; and $R^{19}$ is hydrogen, halogen or $C_1$-$C_6$alkyl.

In still another embodiment the present invention provides a compound of formula I wherein E is N and -A-B-D- is —$CR^{17}$—$CR^{18}$—$CR^{19}$—, —N—$CR^{18}$—$CR^{19}$— or —$CR^{17}$—N—$CR^{19}$—, wherein $R^{17}$ is hydrogen or halogen; $R^{18}$ is hydrogen; and $R^{19}$ is hydrogen, halogen or $C_1$-$C_6$alkyl.

In one embodiment the present invention provides a compound of formula I wherein E is S and -A-B-D- is —CH—CH—.

In one embodiment the present invention provides a compound of formula I wherein n is 1. In one embodiment the present invention provides a compound of formula I wherein n is 3.

In addition to the foregoing the present invention also provides a process for the production of a compound of formula I

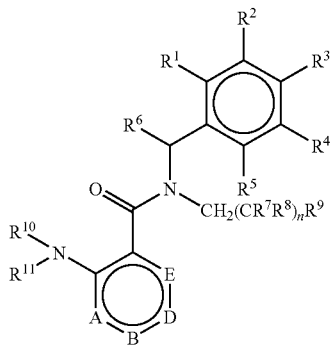

(I)

wherein $R^1$, $R^2$, $R^4$ and $R^5$ are independently hydrogen, $C_1$-$C_6$alkyl, $C_1$-$C_6$alkoxy or halogen;

$R^3$ is $C_1$-$C_6$alkyl, halogen-$C_1$-$C_6$alkyl, $C_3$-$C_6$cycloalkyl, $Si(C_1$-$C_6$alkyl$)_3$, —$OR^{12}$, wherein $R^{12}$ is $C_1$-$C_6$alkyl, halogen-$C_1$-$C_6$alkyl, $C_3$-$C_6$cycloalkyl, phenyl, benzyl or $S(O)_2$—$C_1$-$C_6$alkyl, or pentafluorosulphuranyl; or $R^2$ and $R^3$ taken together with the carbon atoms they are attached to form a 5- or 6-membered carbocyclic ring or a 5- or 6-membered heterocyclic ring containing one or two heteroatoms selected from N, O or S;

$R^6$ is hydrogen or $C_1$-$C_6$alkyl;

$R^7$ and $R^8$ are independently hydrogen, $C_1$-$C_6$alkyl, hydroxy or halogen;

$R^9$ is hydrogen, $C_1$-$C_6$alkyl, $C_2$-$C_6$alkenyl, halogen-$C_1$-$C_6$alkyl, heterocyclyl, heteroaryl, phenyl, naphthyl, —$OR^{13}$, wherein $R^{13}$ is $C_1$-$C_6$alkyl or phenyl, —$NR^{14}R^{15}$, wherein $R^{14}$ and $R^{15}$ independently are hydrogen, $C_1$-$C_6$alkyl or phenyl, or —C(O)—$OR^{16}$, wherein $R^{16}$ is hydrogen or $C_1$-$C_6$alkyl;

$R^{10}$ and $R^{11}$ are independently hydrogen, halogen, $C_1$-$C_6$alkyl, COR wherein R is $C_1$-$C_6$alkyl, $C_1$-$C_6$alkoxy or $C_3$-$C_6$cycloalkyl, $S(O)_2$—$C_1$-$C_6$alkyl, $C_3$-$C_6$cycloalkyl, or phenyl; or together are $C_1$-$C_6$alkylene;

A is $CR^{17}$ or N, wherein $R^{17}$ is hydrogen, halogen, $C_1$-$C_6$alkyl, $C_1$-$C_6$alkoxy or $C_2$-$C_6$alkenyl;

B is $CR^{18}$ or N, wherein $R^{18}$ is hydrogen, halogen, $C_1$-$C_6$alkyl, $C_1$-$C_6$alkoxy or $C_2$-$C_6$alkenyl;

D is $CR^{19}$ or N, wherein $R^{19}$ is hydrogen, halogen, $C_1$-$C_6$alkyl, $C_1$-$C_6$alkoxy, $C_2$-$C_6$alkenyl or phenyl;

E is $CR^{20}$ or N, wherein $R^{20}$ is hydrogen, halogen, $C_1$-$C_6$alkyl, $C_1$-$C_6$alkoxy or $C_2$-$C_6$alkenyl; or E is $CR^{20}$ and -A-B-D- is —N—O—, —$NR^{21}$—N—, —S—N—, —S—CH— or —CH—S—, wherein $R^{21}$ is hydrogen, halogen, $C_1$-$C_6$alkyl, $C_1$-$C_6$alkoxy or $C_2$-$C_6$alkenyl; or E is N and -A-B-D- is —N—O—, —S—N—, —S—CH—, —CH—CH— or —CH—S—; or E is S and -A-B-D- is —CH—CH—; and n is 1, 2 or 3;

which process comprises reacting an acid derivative, a compound of formula II

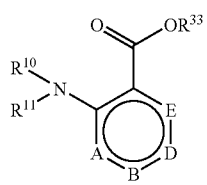

(II)

wherein $R^{33}$ is hydrogen, Li, Na, K or $C_1$-$C_6$alkyl; and $R^{10}$, $R^{11}$, A, B, D and E have the above meanings;

with a secondary amine derivative, a compound of formula III

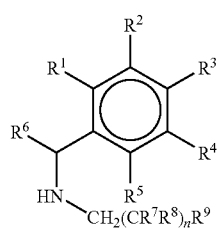

(III)

wherein $R^1$, $R^2$, $R^3$, $R^4$, $R^5$, $R^6$, $R^7$, $R^8$, $R^9$ and n have the above meanings.

If compounds of formula II are used in this process wherein $R^{33}$ is hydrogen or Li, Na or K (acids), standard peptide coupling reagents can be applied to activate the acid prior to the coupling reaction. Typically, the acid derivative of formula II ($R^{33}$ is hydrogen, Li, Na, K) is mixed with a coupling reagent such as EDC or EDC.HCl, DCC, HBTU or TBTU in an inert solvent such as N,N-dimethylformamide, dimethylacetamide (DMA) or dichloromethane (DCM) together with the appropriate secondary amine derivative III. Optionally a base (e.g. N,N-diisopropylethyl amine, triethylamine, N-methyl morpholine) and/or 1-hydroxybenzotriazole (HOBT) can be added. The reaction mixture is stirred for 1 to 24 h at a temperature of about –30° C. to about 70° C. (e.g. ambient temperature).

Alternatively, esters of formula II ($R^{33}$ is $C_1$-$C_6$alkyl, e.g. $CH_3$ or $C_2H_5$) may be used in the coupling process. In that case, the amine derivative III is treated with trimethylaluminum in an inert solvent such as DCM or toluene at ambient temperature prior to the addition of the ester derivative II.

In another embodiment the present invention provides a process for the production of a compound of formula I wherein $R^1$, $R^2$, $R^4$ and $R^5$ are independently hydrogen, $C_1$-$C_6$alkyl, $C_1$-$C_6$alkoxy or halogen;

$R^3$ is $C_1$-$C_6$alkyl, halogen-$C_1$-$C_6$alkyl, $C_3$-$C_6$cycloalkyl, $Si(C_1$-$C_6$alkyl$)_3$, —$OR^{12}$, wherein $R^{12}$ is $C_1$-$C_6$alkyl, halogen-$C_1$-$C_6$alkyl, $C_3$-$C_6$cycloalkyl, phenyl, benzyl or $S(O)_2$—$C_1$-$C_6$alkyl, or pentafluorosulphuranyl; or $R^2$ and $R^3$ taken together with the carbon atoms they are attached to form a 5- or 6-membered carbocyclic ring or a 5- or 6-membered heterocyclic ring containing one or two heteroatoms selected from N, O or S;

$R^6$ is hydrogen or $C_1$-$C_6$alkyl;

$R^7$ and $R^8$ are independently hydrogen, $C_1$-$C_6$alkyl, hydroxy or halogen;

$R^9$ is hydrogen, $C_1$-$C_6$alkyl, $C_2$-$C_6$alkenyl, halogen-$C_1$-$C_6$alkyl, heterocyclyl, heteroaryl, phenyl, naphthyl, —$OR^{13}$, wherein $R^{13}$ is $C_1$-$C_6$alkyl or phenyl, —$NR^{14}R^{15}$, wherein $R^{14}$ and $R^{15}$ independently are hydrogen, $C_1$-$C_6$alkyl or phenyl, or —C(O)—$OR^{16}$, wherein $R^{16}$ is hydrogen or $C_1$-$C_6$alkyl;

$R^{10}$ is hydrogen, halogen, $C_1$-$C_6$alkyl, COR wherein R is $C_1$-$C_6$alkyl, $C_1$-$C_6$alkoxy or $C_3$-$C_6$cycloalkyl, $S(O)_2$—$C_1$-$C_6$alkyl, $C_3$-$C_6$cycloalkyl, or phenyl;

$R^{11}$ is hydrogen;

A is $CR^{17}$ or N, wherein $R^{17}$ is hydrogen, halogen, $C_1$-$C_6$alkyl, $C_1$-$C_6$alkoxy or $C_2$-$C_6$alkenyl;

B is $CR^{18}$ or N, wherein $R^{18}$ is hydrogen, halogen, $C_1$-$C_6$alkyl, $C_1$-$C_6$alkoxy or $C_2$-$C_6$alkenyl;

D is $CR^{19}$ or N, wherein $R^{19}$ is hydrogen, halogen, $C_1$-$C_6$alkyl, $C_1$-$C_6$alkoxy, $C_2$-$C_6$alkenyl or phenyl;

E is $CR^{20}$ or N, wherein $R^{20}$ is hydrogen, halogen, $C_1$-$C_6$alkyl, $C_1$-$C_6$alkoxy or $C_2$-$C_6$alkenyl; or E is $CR^{20}$ and -A-B-D- is —N—O—, —$NR^{21}$—N—, —S—N—, —S—CH— or —CH—S—, wherein $R^{21}$ is hydrogen, halogen, $C_1$-$C_6$alkyl, $C_1$-$C_6$alkoxy or $C_2$-$C_6$alkenyl; or E is N and -A-B-D- is —N—O—, —S—N—, —S—CH—, —CH—CH— or —CH—S—; or E is S and -A-B-D- is —CH—CH—; and n is 1, 2 or 3;

which process comprises reacting a compound of formula IV

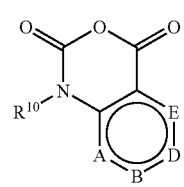

(IV)

wherein $R^{10}$, A, B, D and E have the above meanings;

with a secondary amine derivative, a compound of formula III wherein $R^1$, $R^2$, $R^3$, $R^4$, $R^5$, $R^6$, $R^7$, $R^8$, $R^9$ and n have the above meanings.

A compound of formula IV and a formula III compound are mixed together in an inert solvent such as DMF or toluene and the reaction mixture is heated (e.g. to reflux) for 1 to 24 h. Formula IV compounds are commercially available or can be synthesized according to literature procedures or as described in the example section.

In another embodiment the present invention also provides a process for the production of a compound of formula I wherein $R^1$, $R^2$, $R^4$ and $R^5$ are independently hydrogen, $C_1$-$C_6$alkyl, $C_1$-$C_6$alkoxy or halogen;

$R^3$ is $C_1$-$C_6$alkyl, halogen-$C_1$-$C_6$alkyl, $C_3$-$C_6$cycloalkyl, $Si(C_1$-$C_6alkyl)_3$, —$OR^{12}$, wherein $R^{12}$ is $C_1$-$C_6$alkyl, halogen-$C_1$-$C_6$alkyl, $C_3$-$C_6$cycloalkyl, phenyl, benzyl or $S(O)_2$—$C_1$-$C_6$alkyl, or pentafluorosulphuranyl; or $R^2$ and $R^3$ taken together with the carbon atoms they are attached to form a 5- or 6-membered carbocyclic ring or a 5- or 6-membered heterocyclic ring containing one or two heteroatoms selected from N, O or S;

$R^6$ is hydrogen or $C_1$-$C_6$alkyl;

$R^7$ and $R^8$ are independently hydrogen, $C_1$-$C_6$alkyl, hydroxy or halogen;

$R^9$ is hydrogen, $C_1$-$C_6$alkyl, $C_2$-$C_6$alkenyl, halogen-$C_1$-$C_6$alkyl, heterocyclyl, heteroaryl, phenyl, naphthyl, —$OR^{13}$, wherein $R^{13}$ is $C_1$-$C_6$alkyl or phenyl, —$NR^{14}R^{15}$, wherein $R^{14}$ and $R^{15}$ independently are hydrogen, $C_1$-$C_6$alkyl or phenyl, or —C(O)—$OR^{16}$, wherein $R^{16}$ is hydrogen or $C_1$-$C_6$alkyl;

$R^{10}$ and $R^{11}$ are independently hydrogen, halogen, $C_1$-$C_6$alkyl, COR wherein R is $C_1$-$C_6$alkyl, $C_1$-$C_6$alkoxy or $C_3$-$C_6$cycloalkyl, $S(O)_2$—$C_1$-$C_6$alkyl, $C_3$-$C_6$cycloalkyl, or phenyl; or together are $C_1$-$C_6$alkylene;

E is $CR^{20}$ and -A-B-D- is —N—$CR^{18}$—N—;

$R^{18}$ and $R^{20}$ independently are hydrogen, halogen, $C_1$-$C_6$alkyl, $C_1$-$C_6$alkoxy or $C_2$-$C_6$alkenyl; and n is 1, 2 or 3;

which process comprises reacting a compound of formula V

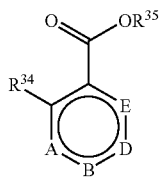

(V)

wherein $R^{34}$ is halogen, e.g. Cl or F;

$R^{35}$ is hydrogen, Li, Na or K;

E is $CR^{20}$ and -A-B-D- is —N—$CR^{18}$—N—; wherein $R^{18}$ and $R^{20}$ independently are hydrogen, halogen, $C_1$-$C_6$alkyl, $C_1$-$C_6$alkoxy or $C_2$-$C_6$alkenyl;

with a compound of formula III wherein $R^1$, $R^2$, $R^3$, $R^4$, $R^5$, $R^6$, $R^7$, $R^8$, $R^9$ and n have the above meanings, and treating the resulting compound of formula VI

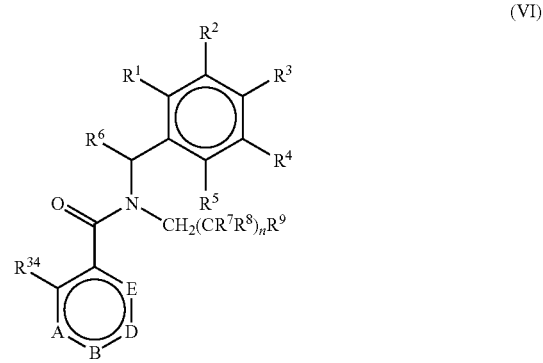

(VI)

with an amine derivative $HNR^{10}R^{11}$.

The reaction may be performed in an inert solvent such as THF, dioxane, water or mixtures thereof at elevated temperatures using conventional or e.g. microwave heating.

Compounds of formula I wherein $R^{10}$ and $R^{11}$ are hydrogen (Ic) can be transformed into compounds of formula I wherein $R^{10}$ is $C_1$-$C_6$alkyl, COR wherein R is $C_1$-$C_6$alkyl, $C_1$-$C_6$alkoxy or $C_3$-$C_6$cycloalkyl, $S(O)_2$—$C_1$-$C_6$alkyl, $C_3$-$C_6$cycloalkyl, or phenyl; and $R^{11}$ is hydrogen, either by reductive alkylation, by acylation or sulfonylation depending on the nature of the substituent $R^{10}$ that is introduced. These alkylation, acylation or sulfonylation reactions can be performed using standard conditions described in the literature.

Conversion of formula I compounds wherein $R^{10}$ is hydrogen and $R^{11}$ is trifluoroacetyl, into derivatives of formula I wherein $R^{10}$ is $C_1$-$C_6$alkyl, can be accomplished in two steps, by reacting a compound of formula I wherein $R^{11}$ is trifluoroacetyl and $R^{10}$ is hydrogen with an alkylating agent $R^{10}$—X (wherein $R^{10}$ is $C_1$-$C_6$alkyl and X is halogen, e.g. Cl, Br, I) in the presence of a base such as sodium hydride in an inert solvent such as DMF or DMA (optionally DMPU can be added) to give compounds of formula I wherein $R^{11}$ is trifluoroacetyl and $R^{10}$ is $C_1$-$C_6$alkyl, followed by cleavage of the trifluoroacetamide group using a base such as sodium hydroxide or potassium hydroxide in a solvent such as methanol or ethanol at temperatures between 0° C. and 100° C.

In another embodiment the present invention provides a process for the production of a compound of formula I wherein $R^1$, $R^2$, $R^4$ and $R^5$ are independently hydrogen, $C_1$-$C_6$alkyl, $C_1$-$C_6$alkoxy or halogen;

$R^3$ is —$OR^{12}$, wherein $R^{12}$ is $C_1$-$C_6$alkyl, $C_3$-$C_6$cycloalkyl, phenyl, benzyl or $S(O)_2$—$C_1$-$C_6$alkyl;

$R^6$ is hydrogen or $C_1$-$C_6$alkyl;

$R^7$ and $R^8$ are independently hydrogen, $C_1$-$C_6$alkyl, hydroxy or halogen;

$R^9$ is hydrogen, $C_1$-$C_6$alkyl, $C_2$-$C_6$alkenyl, halogen-$C_1$-$C_6$alkyl, heterocyclyl, heteroaryl, phenyl, naphthyl, —$OR^{13}$, wherein $R^{13}$ is $C_1$-$C_6$alkyl or phenyl, —$NR^{14}R^{15}$, wherein $R^{14}$ and $R^{15}$ independently are hydrogen, $C_1$-$C_6$alkyl or phenyl, or —C(O)—$OR^{16}$, wherein $R^{16}$ is hydrogen or $C_1$-$C_6$alkyl;

$R^{10}$ is hydrogen, halogen, $C_1$-$C_6$alkyl, COR wherein R is $C_1$-$C_6$alkyl, $C_1$-$C_6$alkoxy or $C_3$-$C_6$cycloalkyl, $S(O)_2$—$C_1$-$C_6$alkyl, $C_3$-$C_6$cycloalkyl, or phenyl;

$R^{11}$ is hydrogen;

A is $CR^{17}$ or N, wherein $R^{17}$ is hydrogen, halogen, $C_1$-$C_6$alkyl, $C_1$-$C_6$alkoxy or $C_2$-$C_6$alkenyl;

B is $CR^{18}$ or N, wherein $R^{18}$ is hydrogen, halogen, $C_1$-$C_6$alkyl, $C_1$-$C_6$alkoxy or $C_2$-$C_6$alkenyl;

D is $CR^{19}$ or N, wherein $R^{19}$ is hydrogen, halogen, $C_1$-$C_6$alkyl, $C_1$-$C_6$alkoxy, $C_2$-$C_6$alkenyl or phenyl;

E is $CR^{20}$ or N, wherein $R^{20}$ is hydrogen, halogen, $C_1$-$C_6$alkyl, $C_1$-$C_6$alkoxy or $C_2$-$C_6$alkenyl; or E is $CR^{20}$ and -A-B-D- is —N—O—, —$NR^{21}$—N—, —S—N—, —S—CH— or —CH—S—, wherein $R^{21}$ is hydrogen, halogen, $C_1$-$C_6$alkyl, $C_1$-$C_6$alkoxy or $C_2$-$C_6$alkenyl; or E is N and -A-B-D- is —N—O—, —S—N—, —S—CH—, —CH—CH— or —CH—S—; or E is S and -A-B-D- is —CH—CH—; and n is 1, 2 or 3;

which process comprises cleavage of the benzylic ether bond in a compound of formula I wherein $R^3$ is benzyloxy (e.g. with $H_2$, Pd/C in ethyl acetate) and reacting the resulting compound with an alkylating agent $R^{12}$—X (with X=Cl, Br, I) in the presence of a base such as potassium carbonate in an inert solvent such as DMF or DMA at a temperature between 0° C. and 100° C.

Acid derivatives of formula II are commercially available or can be prepared as described in the example section.

Secondary amines of the general formula III can be synthesized by standard methods. They may be synthesized as outlined below.

Compounds of formula III

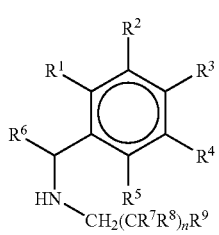

(III)

wherein $R^6$ is hydrogen may be prepared by reductive amination of a benzaldehyde, a compound of formula VIII

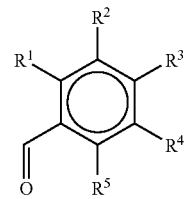

(VIII)

with an amine, a compound of formula IX

(IX)

The above reaction may take place in the presence of a suitable reducing agent, e.g. sodium borohydrate.

Alternatively, compounds of formula III wherein $R^6$ is hydrogen may be prepared by reacting a compound of formula X

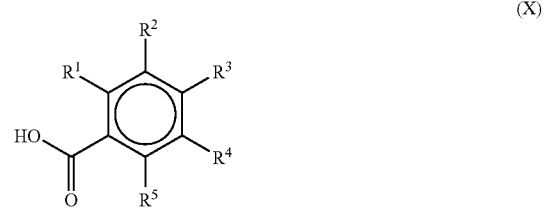

(X)

with a compound of formula IX and reducing the resulting amide, compound of formula XI

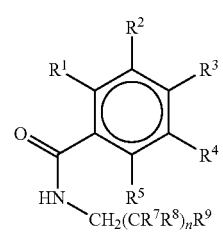

(XI)

Compounds of formula VIII and IX are commercially available or may be synthesized using standard methods as e.g. described in the example section.

Alternatively, compounds of formula III wherein $R^6$ is hydrogen may be prepared by reacting a compound of formula XII

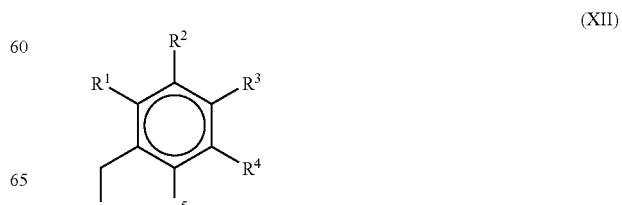

(XII)

with a compound of formula XIII

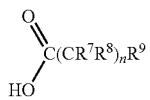

and reducing the resulting amide, a compound of formula XIV

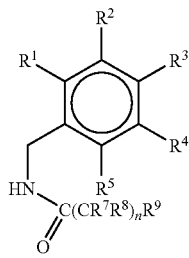

Whereas amide derivatives of formula XI are available by the coupling of benzoic acid derivatives X with amines IX, amides of formula XIV can be synthesized by coupling benzylic amines XII with acids XIII. These amide couplings can be accomplished using standard coupling reagents and conditions (as described above). The necessary starting amines and acids are commercially available or are synthesized using standard conditions as e.g. described in the example section.

Alternatively, compounds of formula III wherein $R^6$ is $C_1$-$C_6$alkyl may be prepared by reacting a compound of formula XV

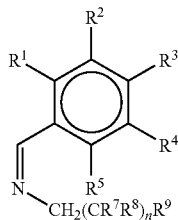

with an alkyllithium reagent R'Li, wherein R' is $C_1$-$C_6$ alkyl, e.g. with methyllithium, in the presence of a Lewis acid such as boron trifluoride ethyl etherate.

Imines XV are accessible from aldehydes VIII and amines IX by standard methods

In the examples the following abbreviations are used: RT: room temperature; DMF: N,N-dimethylformamide; DCM: dichloromethane.

In general, the nomenclature used in this Application is based on AUTONOM™ v.4.0, a Beilstein Institute computerized system for the generation of IUPAC systematic nomenclature.

Preparation of Starting Compounds

Aldehydes (Acids/Nitriles): (Compounds of Formula VIII and X)

EXAMPLE S1-A

Preparation of 4-cyclopropyl benzaldehyde

To a solution of 1-bromo-4-cyclopropylbenzene [synthesized in analogy to a procedure described in J. Org. Chem. 1976, 41, 2262-2266] (1.58 g, 8.04 mmol) in THF at −78° C. was added n-BuLi (5.08 ml, 1.6M solution in hexane, 8.11 mmol) and the reaction mixture was stirred at −78° C. for 10 min. DMF (1.25 ml, 16.08 mmol) was then added and the reaction mixture was stirred at −78° C. for 15 min. The reaction mixture was then warmed to 0° C. slowly (over 2 h) and stirred at 0° C. for 1 h. The reaction was quenched with sat. $NH_4Cl_{(aq)}$ solution and the aqueous phase was extracted with ether. The organic layer was washed with brine, dried ($MgSO_4$), filtered and concentrated in vacuo to give a residue which was purified by flash column chromatography (1:9 diethylether/pentane) to give 4-cyclopropyl benzaldehyde (1.10 g, 94%) as a colourless oil. $^{1H}$NMR ($CDCl_3$, 300 MHz): δ 9.94 (s, 1H), 7.76 (d, J=8.5 Hz, 2H), 7.19 (d, J=8.5 Hz, 2H), 1.97 (m, 1H), 1.13-1.06 (m, 2H), 0.84-0.78 (m, 2H).

EXAMPLE S2-A

Preparation of 4-cyclobutyl benzaldehyde a) Preparation of 1-(4-bromophenyl)-cyclobutanol To a solution of 1,4-dibromobenzene (1.00 g, 4.24 mmol) at −78° C. in ether (20 ml) was added n-BuLi (2.65 ml, 1.6 M solution in hexane, 4.24 mmol) and the reaction mixture was stirred at −78° C. for 30 min. Cyclobutanone (348 µl, 4.66 mmol) was then added and the reaction mixture was stirred at −78° C. for 15 min. The reaction mixture was then slowly (over 2 h) warmed to 0° C. and stirred for a further 1 h. Water was added followed by sat. $NH_4Cl$ and the reaction mixture was extracted with ether. The organic layer was washed with brine, dried ($MgSO_4$), filtered and concentrated in vacuo to give a residue which was purified by flash column chromatography (1:4 ether/pentane) to give 1-(4-bromophenyl)-cyclobutanol (330 mg, 34%) as a colourless oil. $^{1H}$ NMR ($CDCl_3$, 300 MHz): δ 7.50 (d, J=8.5 Hz, 2H), 7.38 (d, J=8.5 Hz, 2H), 2.57-2.48 (m, 2H), 2.41-2.31 (m, 2H), 2.02 (m, 1H), 1.69 (m, 1H).

b) Preparation of bromo-4-cyclobutyl-benzene

To a solution of 1.37 g of 1-(4-bromophenyl)-cyclobutanol (6 mmol) in 15 ml DCM were added 1.15 ml of triethylsilane (7.2 mmol) and the mixture was cooled to −78° C. Then 1.15 ml of boron trifluoride diethyl etherate complex were added and the reaction mixture was warmed to −40° C. and stirred for 8 h. The reaction was then quenched by addition of 10% aqueous $KHCO_3$ and the mixture was extracted three times with DCM. The combined extracts were washed with brine, dried with magnesium sulfate and concentrated. The remaining residue was purified by column chromatography (silica gel; cyclohexane) to give 0.84 g (66%) of 1-bromo-4-cyclobutyl-benzene as a colorless liquid. $^{1H}$ NMR ($CDCl_3$, 300 MHz): δ 1.85 (m, 1H), 1.92-2.18 (m, 3H), 2.33 (m, 2H), 3.49 (quint, J=8.5 Hz, 1H), 7.08 (d, J=8.5 Hz, 2H), 7.40 (d, J=8.5 Hz, 2H).

c) Preparation of 4-cyclobutyl-benzaldehyde

The title compound was synthesized in analogy to 4-cyclopropyl benzaldehyde (described in example S1-A) using 830 mg of 1-bromo-4-cyclobutyl-benzene (3.93 mmol), 2.7 ml of a 1.6 molar solution of n-BuLi in hexane (4.32 mmol) and 605 µl of DMF (7.86 mmol). The isolated residue was purified by flash column chromatography (5:95 EtOAc/cyclohexane) to give 422 mg of 4-cyclobutyl-benzaldehyde (67%) as a colourless liquid. $^{1H}$ NMR (CDCl$_3$, 300 MHz): δ 1.89 (m, 1H), 1.97-2.26 (m, 3H), 2.40 (m, 2H), 3.63 (quint, J=8.5 Hz, 1H), 7.36 (d, J=8.0 Hz, 2H), 7.81 (d, J=8.0 Hz, 2H), 9.97 (s, 1H).

EXAMPLE S3-A

Preparation of 4-cyclopentyl benzaldehyde a) Preparation of 1-(4-bromo-phenyl)-cyclopentanol

The title compound was synthesized in analogy to 1-(4-bromo-phenyl)-cyclobutanol (described in example S2-A) using 3 g of 1,4-dibromobenzene (12.7 mmol), 7.95 ml of a 1.6 molar solution of n-BuLi in hexane (12.7 mmol) and 1.24 ml of cyclopentanone (14.0 mmol). The isolated residue was purified by flash column chromatography (1:4 diethyl ether/pentane) to give 1.2 g of 1-(4-bromo-phenyl)-cyclopentanol (39%) as a colourless liquid.

b) Preparation of 1-bromo-4-cyclopent-1-enyl-benzene

To a solution of 2.62 g of 1-(4-bromo-phenyl)-cyclopentanol (10.9 mmol) in 50 ml toluene were added 124 mg of toluene-4-sulfonic acid (1 mmol) and the mixture was heated to reflux for 4 h. After the reaction mixture was allowed to cool to RT it was washed with sat. NaHCO$_3$-solution and brine, dried (MgSO$_4$), filtered and concentrated in vacuo to give 2.12 g of 1-bromo-4-cyclopent-1-enyl-benzene (88%) as an off-white solid.

c) Preparation of 1-bromo-4-cyclopentyl-benzene

A mixture of 1.04 g of 1-bromo-4-cyclopent-1-enyl-benzene (4.7 mmol) and 100 mg of PtO$_2$ in 25 ml toluene was stirred under an atmosphere of hydrogen at RT for 6 h. The reaction mixture was then filtered and the filtrate was evaporated to dryness to give 1.0 g of 1-bromo-4-cyclopentyl-benzene (95%) as a yellow liquid.

d) Preparation of 4-cyclopentyl-benzaldehyde

The title compound was synthesized in analogy to 4-cyclopropyl benzaldehyde (described in example S1-A) using 2.07 g of 1-bromo-4-cyclopentyl-benzene (9.2 mmol), 6.32 ml of a 1.6 molar solution of n-BuLi in hexane (10.11 mmol) and 1.422 ml of DMF (18.4 mmol). 4-Cyclopentyl-benzaldehyde was isolated by flash column chromatography (5:95 EtOAc/c-hexane) as a colorless liquid (1146 mg, 72%). $^{1H}$ NMR (CDCl$_3$, 300 MHz): δ 1.53-1.91 (m, 6H), 2.11 (m, 2H), 3.07 (quint, J=8.5 Hz, 1H), 7.40 (d, J=8 Hz, 2H), 7.80 (d, J=8 Hz, 2H), 9.97 (s, 1H).

EXAMPLE S4-A

Preparation of 4-(1-methoxy-cyclobutyl)-benzaldehyde a) Preparation of 1-bromo-4-(1-methoxycyclobutyl)-benzene

To a suspension of NaH (24 mg, ~55% dispersion in oil, 0.53 mmol) in DMF (2 ml) at 0° C. was added a solution of 1-(4-bromophenyl)-cyclobutanol (100 mg, 0.44 mmol, described in example S2-A) in DMF (2 ml). The mixture was stirred at 0° C. for 30 min and then methyl iodide (41 µl, 0.66 mmol) was added. The reaction mixture was then warmed up to RT and stirring was continued overnight. The mixture was quenched with water and extracted with ether. The organic phase was washed with water and brine, dried (MgSO$_4$), filtered, and concentrated in vacuo to give a residue which was purified by flash column chromatography (1:9 ether/pentane) to give 1-bromo-4-(1-methoxycyclobutyl)-benzene (79 mg, 75%) as a colourless oil. $^{1H}$NMR (CDCl$_3$, 300 MHz): δ 7.50 (d, J=8.5 Hz, 2H), 7.30 (d, J=8.5 Hz, 2H), 2.92 (s, 3H), 2.38-2.33 (m, 4H), 1.94 (m, 1H), 1.67 (m, 1H).

b) Preparation of 4-(1-methoxycyclobutyl)-benzaldehyde

The title compound was synthesized in analogy to 4-cyclopropyl benzaldehyde (described in example S1-A) using 1-bromo-4-(1-methoxycyclobutyl)-benzene (140 mg, 0.58 mmol), n-BuLi (363 µl, 1.6M solution in hexane, 0.58 mmol) and DMF (90 µl, 1.16 mmol). The isolated residue was purified by flash column chromatography (1:9 ether/pentane) to give 4-(1-methoxycyclobutyl)-benzaldehyde (76 mg, 69%) as a colourless oil. $^{1H}$ NMR (CDCl$_3$, 300 MHz): δ 10.03 (s, 1H), 7.91 (d, J=8.5 Hz, 2H), 7.61 (d, J=8.5 Hz, 2H), 2.96 (s, 3H), 2.45-2.39 (m, 4H), 1.99 (m, 1H), 1.73 (m, 1H).

EXAMPLE S5-A

Preparation of 4-(1-fluoro-cyclobutyl)-benzaldehyde a) Preparation of 1-bromo-4-(1-fluoro-cyclobutyl)-benzene

To a solution of 5.66 g of 1-(4-bromophenyl)-cyclobutanol (24.92 mmol, described in example S2-A) in 70 ml DCM were added 4.23 g of (diethylamino)sulfur trifluoride (95%, 24.92 mmol) at 0° C. The reaction mixture was stirred at 0° C. for 35 min, then sat. NaHCO$_3$-solution was added and the resulting mixture was extracted with DCM. The combined organic extracts were washed with brine, dried (MgSO$_4$), filtered, and concentrated in vacuo to give a residue which was purified by flash column chromatography (100% pentane) to give 1-bromo-4-(1-fluoro-cyclobutyl)-benzene (3.66 g, 64%) as a colourless liquid.

b) Preparation of 4-(1-fluoro-cyclobutyl)-benzaldehyde

The title compound was synthesized in analogy to 4-cyclopropyl benzaldehyde (described in example S1-A) using 1.64 g of 1-bromo-4-(1-fluoro-cyclobutyl)-benzene (7.16 mmol), 4.92 ml of a 1.6 molar solution of n-BuLi in hexane (7.87 mmol) and 1.1 ml of DMF (14.32 mmol). 4-(1-Fluoro-cyclobutyl)-benzaldehyde was isolated crude as a light yellow liquid (1.23 g, 96%). $^{1H}$NMR (CDCl$_3$, 300 MHz): δ 1.84 (m, 1H), 2.15 (m, 1H), 2.49-2.81 (m, 5H), 7.63 (d, J=8 Hz, 2H), 7.92 (d, J=8 Hz, 2H), 10.03 (s, 1H).

EXAMPLE S6-A

Preparation of 4-(1-methoxycyclopropyl)-benzaldehyde

Preparation of 1-bromo-4-(1-methoxycyclopropyl)-benzene

Trimethyl orthoformate (2.75 ml, 25.12 mmol) was added to 4-bromoacetophenone (5.00 g, 25.12 mmol) followed by p-toluenesulfonic acid (239 mg, 1.26 mmol). The reaction mixture was stirred at RT for 30 h. The methyl formate and methanol formed in the reaction were distilled off slowly for at least 4 h at 85° C. until no further methanol was being formed. The reaction mixture was cooled to RT and a few drops of triethylamine were added. The crude residue was then purified by flash column chromatography (5% EtOAc, 1% Et$_3$N in cyclohexane) to give a mixture of 1-bromo-4-(1-methoxyvinyl)-benzene and 1-bromo-4-(1,1-dimethoxyethyl)-benzene in a 1:1 mixture. The products were not separated and reacted in the next step as a mixture.

To a solution of 2,4,6-trichlorophenol (1.90 g, 9.64 mmol) in methylene chloride (70 ml) at −40° C. was added diethyl zinc (9.64 ml, 1M solution in hexane, 9.64 mmol). The mixture was stirred at −40° C. for 20 min and then CH$_2$I$_2$ (778 μl, 9.64 mmol) was added. After stirring for an additional 20 min, 1-bromo-4-(1-methoxyvinyl)-benzene (1.37 g, 6.43 mmol) was added. The reaction mixture was slowly warmed to RT and stirring was continued for 16 h. Pentane was added and the mixture was washed with 1M HCl, sat. NaHCO$_3$, sat. Na$_2$SO$_3$ and brine. The organic layer was dried (MgSO$_4$), filtered, concentrated in vacuo to give a crude residue which was purified by flash column chromatography (2% ethyl acetate in cyclohexane-10% ethyl acetate in cyclohexane) to give 1-bromo-4-(1-methoxycyclopropyl)-benzene (880 mg, 60%) as a yellow oil. $^{1H}$NMR (CDCl$_3$, 300 MHz): δ 7.46 (d, J=8.5 Hz, 2H), 7.18 (d, J=8.5 Hz, 2H), 3.21 (s, 3H), 1.21-1.17 (m, 2H), 0.95-0.91 (m, 2H).

b) Preparation of 4-(1-methoxycyclopropyl)-benzaldehyde

The title compound was synthesized in analogy to 4-cyclopropyl benzaldehyde (described in example S1-A) using 1-bromo-4-(1-methoxycyclopropyl)-benzene (250 mg, 1.10 mmol), n-BuLi (722 μl, 1.6M solution in hexane, 1.16 mmol) and DMF (171 μl, 2.20 mmol). The isolated residue was purified by flash column chromatography (1:9 ether/pentane) to give 4-(1-methoxycyclopropyl)-benzaldehyde (90 mg, 58%) as a colourless oil. $^{1H}$NMR (CDCl$_3$, 300 MHz): δ 10.0 (s, 1H), 7.79 (d, J=8.5 Hz, 2H), 7.37 (d, J=8.5 Hz, 2H), 3.29 (s, 3H), 1.35-1.30 (m, 2H), 1.09-1.05 (m, 2H).

EXAMPLE S7-A

Preparation of 4-(1,2,2,2-tetrafluoro-1-trifluoromethyl-ethyl)-benzaldehyde

A solution of 3.5 g of 4-(heptafluoroisopropyl)-toluene (13.4 mmol) in 100 ml tetrachloromethane was heated to reflux. Then 2.63 g of N-bromosuccinimide (14.8 mmol) and 326 mg of dibenzoyl peroxide (1.34 mmol) were added in small portions. After 5 h the mixture was cooled to 0° C., filtered and the solvent was evaporated. The remaining residue was dissolved in 15 ml ethanol and was added to a suspension that had been prepared by addition of 2-nitropropane (1.4 ml, 15.5 mmol) to a solution of 340 mg sodium (14.8 mmol) in ethanol. This mixture was stirred for 3 days. Then it was filtered, the solvent was removed and the remaining residue was dissolved in EtOAc and washed with 1 N sodium hydroxide solution, 1 N HCl solution, saturated NaHCO$_3$ solution and with brine. The EtOAc layer was then dried with magnesium sulfate, filtered and concentrated. Purification of the residue (silica gel; c-hexane/EtOAc 10:1) gave 1.1 g (30%) of 4-(1,2,2,2-tetrafluoro-1-trifluoromethyl-ethyl)-benzaldehyde as a light yellow oil. $^{1H}$-NMR (CDCl$_3$, 300 MHz): δ 7.82 (d, J=8 Hz, 2H), 8.03 (d, J=8 Hz, 2H), 10.11 (s, 1H).

EXAMPLE S8-A

Preparation of 2-chloro-4-cyclopropyl-benzaldehyde a) Preparation of 4-bromo-2-chloro-benzoic acid methyl ester 3.0 g of 4-bromo-2-chloro-benzoic acid (12.74 mmol) were dissolved in 60 ml methanol and treated with 0.6 ml of concentrated HCl. After 17 h at reflux the reaction mixture was concentrated in vacuo, diluted with DCM and washed with a saturated aqueous NaHCO$_3$ solution and brine, dried with magnesium sulfate, filtered and concentrated in vacuo leading to 2.7 g (85%) of 4-bromo-2-chloro-benzoic acid methyl ester as a light yellow oil. MS (+cEI): 250.0 (M).

b) Preparation of 2-chloro-4-cyclopropyl-benzoic acid methyl ester 2.1 g of crude 4-bromo-2-chloro-benzoic acid methyl ester (8.42 mmol) were dissolved in 38 ml toluene and treated with 0.94 g of cyclopropylboronic acid (10.94 mmol), 6.25 g of potassium phosphate (29.46 mmol), 236 mg of triphenylphosphine (0.84 mmol), 94 mg of palladium acetate (0.42 mmol) and 1.9 ml water. The reaction mixture was stirred 17 h at 100° C. under Argon. After cooling down to RT, the reaction mixture was treated with 80 ml water, extracted with 2×80 ml EtOAc, washed with brine, dried over magnesium sulfate, filtered and concentrated in vacuo. The remaining residue was purified by silicagel chromatography (100 g silicagel, heptane/AcOEt 95:5) leading to 1.17 g of 2-chloro-4-cyclopropyl-benzoic acid methyl ester (66%) as a yellow oil. MS (+cEI): 210.1 (M).

c) Preparation of 2-chloro-4-cyclopropyl-benzaldehyde

To a solution of 7.01 ml Red-Al 13.5 M (24.54 mmol) in toluene was added at 0° C. a solution of 3.0 ml 1-methylpiperazine (26.89 mmol) in 16 ml toluene over 30 min. The resulting solution was then added dropwise over 40 min to 1.1 g of 2-chloro-4-cyclopropyl-benzoic acid methyl ester (5.2 mmol) in 32 ml toluene between −5° C. and 0° C. After stirring for 30 min at this temperature, the reaction mixture was cooled to −10° C. and treated dropwise with 30 ml water. The mixture was then filtered, diluted with ethylacetate, washed with 1N—HCl, brine, dried over magnesium sulfate, filtered again and concentrated in vacuo, leading to 0.98 g of 2-chloro-4-cyclopropyl-benzaldehyde as a brown oil (100%). MS (+cEI): 180.1 (M).

EXAMPLE S9-A

Preparation of 4-pentafluoroethyl-benzonitrile

A mixture of 4-iodobenzonitrile (10.0 g, 43.7 mmol), sodium pentafluoroproprionate (15.4 g, 82.9 mmol), and copper(I) iodide (16.6 g, 87.3 mmol), DMF (160 mL), and toluene (60 mL) was heated at 160° C. for 16 h, allowing most of the toluene to distil off. After cooling, ethyl acetate (200 mL) was added, and the mixture was filtered through diatomaceous earth, and the filtrate was partitioned between ethyl acetate/heptane and water. The organic layer was washed with brine, dried (MgSO$_4$), and evaporated. Chromatography (SiO$_2$, heptane-ethyl acetate gradient) afforded the title compound (5.05 g 52%). Yellow oil, MS (EI) 221.1 (M$^+$).

EXAMPLE S10-A

Preparation of 4-pentafluoroethyl-benzoic acid

A mixture of 4-pentafluoroethyl-benzonitrile (2.98 g, 13.5 mmol) and potassium hydroxide (3.03 g, 54.0 mmol) in water (40 mL) and ethanol (20 mL) was heated at reflux for 16 h. After cooling, the solution was partitioned between 1 M aq. hydrochloric acid solution and ethyl acetate. The organic layer was washed with brine, dried (MgSO$_4$), and evaporated. Chromatography (SiO$_2$, heptane-ethyl acetate gradient) produced the title compound (2.76 g, 85%). White solid, MS (ISP) 238.9 (M−H)$^−$.

EXAMPLE S11-A

Preparation of 4-(1-fluoro-cyclopropyl)benzoic acid a) Preparation of 1-(2,2-dichloro-1-fluoro-cyclopropyl)-4-methyl-benzene

50% aq. sodium hydroxide solution (4.4 mL, 54 mmol) was added dropwise at 0° C. to a solution of 1-(1-fluoro-vinyl)-4-methyl-benzene (J. Med. Chem. 2004, 47, 5860; 1.84 g, 13.5 mmol) and benzyltriethylammonium chloride (123 mg, 0.54 mmol) in chloroform (20 mL), then after 30 min the ice bath was removed and stirring continued over 16 h. Ice water was added, the organic layer was subsequently washed with 0.1 M aq. hydrochloric acid solution, 5% aq. sodium hydrogencarbonate solution and brine, dried (MgSO$_4$), and evaporated. Chromatography (SiO$_2$, heptane) afforded the title compound (2.54 g, 86%). Light yellow liquid, MS (EI) 218.0 (M$^+$).

b) Preparation of 1-(1-fluoro-cyclopropyl)-4-methyl-benzene

A solution of 1-(2,2-dichloro-1-fluoro-cyclopropyl)-4-methyl-benzene (1.18 g, 5.39 mmol) in THF (10 mL) was added at 0° C. to a suspension of lithium aluminum hydride (1.64 g, 43.1 mmol) in THF. The reaction mixture was stirred for 16 h at RT, then another portion of lithium aluminum hydride (613 mg, 16.1 mmol) was added, then after 3 h, 1 M aq. potassium sodium tartrate solution, methanol and ethyl acetate were added. The organic layer was washed with brine, dried (MgSO$_4$), and evaporated. Chromatography (SiO$_2$, heptane) afforded the title compound (702 mg, 87%). Colourless liquid, MS (EI) 150.1 (M$^+$).

c) Preparation of 4-(1-fluoro-cyclopropyl)benzoic acid

Oxygen was slowly bubbled at 100° C. through a solution of 1-(1-fluoro-cyclopropyl)-4-methyl-benzene (470 mg, 3.13 mmol), cobalt(II)acetate tetrahydrate (117 mg, 0.46 mmol), and acetaldehyde (0.18 mL, 3.1 mmol) in acetic acid (30 mL) over 16 h. After cooling, the reaction mixture was evaporated and the residue triturated in water. The precipitate was collected by filtration to produce the title compound (257 mg, 46%). Light green solid, MS (EI) 180.1 (M$^+$).

EXAMPLE S12-A

Preparation 4-cyclopropyl-3-fluoro-benzaldehyde

The title compound was prepared in analogy to 2-chloro-4-cyclopropyl-benzaldehyde described in example S8-A. MS (ISP): 165.2 (M+H)$^+$

EXAMPLE S13-A

Preparation 4-cyclopropyl-2-fluoro-benzaldehyde

The title compound was prepared in analogy to 2-chloro-4-cyclopropyl-benzaldehyde described in example S8-A. MS (ISP): 165.2 (M+H)$^+$

EXAMPLE S14-A

Preparation of 4-trimethylsilanyl-benzaldehyde

Bromo-4-(trimethylsilyl)benzene (1.15 g, 5 mmol) was dissolved in THF (30 ml) and cooled to −78° C. Under argon a 1.6 M solution of n-butyl lithium in hexane (3.13 ml, 5 mmol) was added dropwise keeping the temperature below −70° C. The clear colorless solution was stirred at −78° C. for 15 min and DMF (1.156 ml, 15 mmol) was added quickly. The reaction temperature increased to −68° C. The reaction was stirred for additional 15 min at −78° C., quenched with 1N aqueous hydrogen chloride solution and extracted twice with diethyl ether. The combined organic layers were washed twice with water and once with saturated aqueous sodium chloride solution, dried over sodium sulfate, filtered and the solvent was evaporated to afford the product as a colorless oil (920 mg, 100%). The product was pure enough to be used directly in the next step. MS (ISP) 179.2 (M+H⁺). ¹ʰNMR (CDCl₃, 300 MHz): δ 10.02 (s, 1H) 7.84 (d, 2H), 7.69 (d, 2H), 0.31 (s, 9H).

Primary Amines: (Compounds of Formula IX)

EXAMPLE S1-B

Preparation of 2-(3-fluoro-4-trifluoromethyl-phenyl)-ethylamine hydrochloride 3 g of (3-fluoro-4-trifluoromethyl-phenyl)-acetonitrile (14.5 mmol) were dissolved in 23 ml THF and cooled down to 0° C. under nitrogen. 77 ml of a 1M borane-THF complex solution in THF were then added dropwise over 35 min by keeping the temperature between 0-2° C. After addition the reaction mixture was stirred at RT for additional 45 min, and then refluxed for 21 h. The reaction mixture was then cooled down to 0° C. and treated between 2 and 5° C. with 17 ml methanol over a period of 30 min. After 1 h refluxing the reaction mixture was concentrated, the remaining residue was dissolved in DCM and the mixture was extracted twice with 1N aqueous HCl. The combined aqueous phases were then treated with concentrated NaOH to adjust the pH to 12, and then extracted twice with DCM. The combined organic phases were then washed with water, dried over magnesium sulfate, filtered and concentrated in vacuo leading to 2.1 g yellow oily residue. This was dissolved in 50 ml diethylether, treated with 5 ml 2.6N HCl in diethylether, stirred at RT for additional 15 min, evaporated to dryness and dried under vacuo, leading to 2.34 g of the title compound as a white solid (66%). MS (ISP) 208.2 (M+H)⁺.

EXAMPLE S2-B

Preparation of 2-(4-chloro-3-trifluoromethyl-phenyl)-ethylamine hydrochloride a) Preparation of (4-chloro-3-trifluoromethyl-phenyl)-acetonitrile 3.94 g of 4-bromomethyl-1-chloro-2-trifluoromethyl-benzene (14.4 mmol) and 1.06 g sodium cyanide (21.6 mmol) were suspended in 12 ml DMSO under argon and stirring and heated to 50° C. for 1 h. The reaction mixture was then poured on water/ice and extracted four times with DCM. The combined organic phases were washed with water, dried with magnesium sulfate, filtered and concentrated in vacuo, leading to 3.188 g of (4-chloro-3-trifluoromethyl-phenyl)-acetonitrile as a dark red oil, which was directly used in the next step.

b) Preparation of 2-(4-chloro-3-trifluoromethyl-phenyl)-ethylamine hydrochloride The title compound was synthesized in analogy to 2-(3-fluoro-4-trifluoromethyl-phenyl)-ethylamine hydrochloride (described in example S1-B) from 3.188 g of crude (4-chloro-3-trifluoromethyl-phenyl)-acetonitrile (14.5 mmol) and 76 ml of a 1M borane-THF complex solution in THF (76 mmol). The product was obtained as a white solid (1.52 g, 40%). MS (ISP) 224.1 (M+H)⁺.

EXAMPLE S3-B

Preparation of (R)-2-(4-chloro-phenyl)-2-hydroxy-ethylamine hydrochloride 1.9 g of (R (4-chloro-phenyl)-hydroxy-acetonitrile (11 mmol) were dissolved in 18 ml THF under a nitrogen atmosphere and the solution was cooled to 0° C. 58 ml of a 1M borane-THF complex solution in THF were then added dropwise, keeping the temperature between 0-2° C. After completion of the addition the reaction mixture was stirred at RT for additional 45 min and then refluxed for 16 h. The reaction mixture was then cooled down to 0° C. and 13 ml of methanol were added over a period of 35 min keeping the temperature of the mixture between 2 and 5° C. After refluxing the reaction mixture for 1 h it was concentrated, the remaining residue was dissolved in DCM and the mixture was extracted twice with 1N aqueous HCl. The combined aqueous phases are then treated with concentrated NaOH to adjust the pH to 12, and then extracted twice with DCM. The combined organic phases were then washed with water, dried with magnesium sulfate, filtered and concentrated in vacuo leading to a colorless solid which was dissolved in 100 ml diethylether, treated with 4 ml 2.6N HCl in diethyl ether. After 1 h at RT the precipitate was filtered off and dried under high vacuum, leading to 1.24 g white solid (54%). MS (ISP) 172.1 (M+H)⁺.

EXAMPLE S4-B

Preparation of 2-(4-chloro-3-fluoro-phenyl)-ethylamine (S4-B1)

a) Preparation of 1-chloro-2-fluoro-4-(2-nitro-vinyl)-benzene

4-Chloro-3-fluorobenzaldehyde (13 g, 82 mmol) and ammonium acetate (14.6 g, 189 mmol) were dissolved in acetic acid (150 ml) and nitromethane (12.6 ml, 234 mmol) was added. The solution was heated to reflux for 1.5 h. After cooling to RT water (120 ml) was added. A solid precipitated. The reaction was extracted three times with methylene chloride. The combined organic layers were washed with water and sat. aq. NaCl solution, dried over magnesium sulfate, filtered and the solvent was removed in vacuo. The residue was purified by flash column chromatography (Ethyl acetate/cyclohexane:1/4). The crude product was suspended in heptane, filtered and dried to yield 1-chloro-2-fluoro-4-(2-nitro-vinyl)-benzene (10.9 g, 66%) as a light yellow solid. ¹ʰ NMR (CDCl₃, 300 MHz): δ 7.29 (d, J=7.8 Hz, 1H), 7.33 (d, J=9.3 Hz, 1H), 7.50 (t, J=7.5H, 1H), 7.54 (d, J=13.6 Hz, 1H), 7.92 (d, J=13.6 Hz, 1H).

b) Preparation of 2-(4-chloro-3-fluoro-phenyl)-ethylamine

Lithium borohydride (2.16 g, 99 mmol) was suspended in THF (50 ml). Trimethylchlorosilane (21.6 g, 198 mmol) was added dropwise. A solution of 1-chloro-2-fluoro-4-(2-nitro-vinyl)-benzene (5.0 g, 24.8 mmol) in THF (20 ml) was added dropwise. Strong gas evolution and foam formation was observed. The white suspension was stirred at RT for 3 days.

Carefully MeOH (80 ml) was added. The solvents were removed in vacuo and the residue was purified by flash column chromatography ($CH_2Cl_2$/MeOH+5% aq. $NH_4OH$ 4:1) to yield 2-(4-chloro-3-fluoro-phenyl)-ethylamine (3.1 g, 73%) as a white solid. MS (ISP) 174.1 (M+H)$^+$. $^1H$NMR (DMSO-d$_6$, 300 MHz): δ2.92 (t, J=4.8 Hz, 2H), 3.02 (t, J=6.3 Hz, 2H), 7.15 (dd, J=6.0 and 1.2 Hz, 1H), 7.38 (dd, J=1.2 and 7.8 Hz), 7.53 (t, J=6.3 Hz, 1H), 7.93 (br, 2H).

| Example | Name | * | MS (ISP) (M + M)$^+$ |
|---|---|---|---|
| S4-B2 | 2-(3-Difluoromethoxy-phenyl)-ethylamine hydrochloride | S1-B | 188.3 |
| S4-B3 | 2-(3-Chloro-4-fluoro-phenyl)-ethylamine hydrochloride | S1-B | 174.1 |
| S4-B4 | 2-(3-Trifluoromethoxy-phenyl)-ethylamine hydrochloride | S1-B | 206.2 |
| S4-B5 | 2-(2-Fluoro-3-trifluoromethyl-phenyl)-ethylamine hydrochloride | S1-B | 208.1 |
| S4-B6 | 2-(3-Chloro-2-fluoro-phenyl)-ethylamine hydrochloride | S1-B | 174.2 |

*: Prepared in analogy to example

Secondary Amines: (Compounds of Formula III)

EXAMPLE S1-C

Preparation of (4-tert-butyl-benzyl)-[2-(3,4-dichloro-phenyl)-ethyl]-amine 0.38 ml of 4-tert-butylbenzaldehyde (2.25 mmol) and 0.227 ml 2-(3,4-dichloro-phenyl)-ethylamine (1.5 mmol) were dissolved in 4.5 ml methanol at RT, and after stirring for 30 min at RT, were refluxed for 2 h. After cooling down to RT, 85 mg (2.25 mmol) sodium borohydride were added and after stirring for 5 min at RT, the reaction mixture was then refluxed for 2 h. After cooling down to RT, the reaction mixture was treated with 4 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:2) to give 515 mg colorless viscous oil (97%). MS (ISP) 336.2 (M+H)$^+$.

EXAMPLE S2-C

Preparation of (4-tert-butyl-benzyl)-[2-(4-fluoro-3-trifluoromethyl-phenyl)-ethyl]-amine 0.62 ml of 4-tert-butylbenzaldehyde (3.69 mmol), 600 mg of 2-(4-fluoro-3-trifluoromethyl-phenyl)-ethylamine hydrochloride (2.46 mmol) and 340 mg of potassium carbonate (2.46 mmol) were suspended in 7 ml methanol at RT, and after stirring for 30 min at RT, were refluxed for 2 h. After cooling down to RT, 140 mg (3.69 mmol) of sodium borohydride were added and after stirring for 5 min at RT, the reaction mixture was then refluxed for 3 h. After cooling down to RT, the reaction mixture was treated with 0.5 ml 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:4 then 1:2) to give 784 mg light yellow oil (90%). MS (ISP) 354.3 (M+H)$^+$.

EXAMPLE S3-C

Preparation of [2-(4-chlorophenyl)-ethyl]-(4-cyclopropylbenzyl)-amine

A mixture of 4-cyclopropyl benzaldehyde (204 mg, 1.40 mmol), 2-(4-chlorophenyl)-ethyl-amine (217 mg, 1.40 mmol) and molecular sieves (500 mg, 4 Å) in diethyl ether (4 ml) was stirred at RT overnight. The mixture was filtered through celite® and concentrated in vacuo to give the corresponding imine which was dissolved in methanol. Sodium borohydride (79 mg, 2.09 mmol) was added and the reaction mixture was stirred at RT for 4 h. The reaction mixture was then quenched with 0.1N NaOH$_{(aq)}$ and the mixture was diluted with EtOAc and washed with brine. The organic phase was dried (MgSO$_4$), filtered and concentrated in vacuo to give the desired [2-(4-chlorophenyl)-ethyl]-(4-cyclopropylbenzyl)-amine (317 mg, 79%) without further purification as a colourless oil. MS (ISP) 285.9 (M+H)$^+$.

EXAMPLE S4-C

Preparation of (4-tert-butyl-benzyl)-[2-(2-chloro-pyridin-4-yl)-ethyl]-amine a) Preparation of 2-chloro-4-trimethylsilanylethynyl-pyridine A mixture of 2.5 g of 4-bromo-2-chloropyridine (12.6 mmol), 2.2 ml of (trimethylsilyl)acetylene (15.1 mmol), 153 mg of copper(I)iodide (0.79 mmol) and 287 mg of bis(triphenylphosphine)palladium(II)chloride (0.41 mmol) in triethylamine (15 ml) was stirred at RT for 1 h. The triethylamine was then removed in vacuo, water was added and the mixture was extracted with diethylether. The combined organic extracts were then washed with water and brine, dried (Na$_2$SO$_4$), filtered and concentrated in vacuo to give a residue which was purified by column chromatography (heptane/EtOAc 100:0 to 98:2) to give 2-chloro-4-trimethylsilanylethynyl-pyridine (2.394 g, 91%) as a light yellow liquid. MS (ISP) 210.1 (M+H)$^+$.

b) Preparation of 2-chloro-4-ethynyl-pyridine

To a solution of 2.389 g of 2-chloro-4-trimethylsilanylethynyl-pyridine (11.39 mmol) in THF (90 ml) were added 11.39 ml of a 1M TBAF solution in THF at −78° C. and the reaction mixture was stirred for 45 min at 0° C. Then saturated NH$_4$Cl solution was added and the THF was removed under reduced pressure. The aqueous mixture was extracted with diethylether and the combined organic extracts were washed with water and brine, dried (Na$_2$SO$_4$), filtered and concentrated in vacuo. The remaining residue was purified by column chromatography (pentane/diethylether 100:0 to 4:1) to give 2-chloro-4-ethynyl-pyridine (1.427 g, 91%) as an off-white solid. $^1$H-NMR (CDCl$_3$, 300 MHz): δ 3.36 (s, 1H), 7.27 (dd, J=5 and 1 Hz, 2H), 7.40 (br s, 1H), 8.37 (d, J=8 Hz, 2H).

c) Preparation of (4-tert-butyl-benzyl)-[2-(2-chloro-pyridin-4-yl)-ethyl]-amine

A mixture of 1.386 g of 2-chloro-4-ethynyl-pyridine (10.07 mmol), 2.65 ml of 4-tert-butyl-benzylamine (15.11 mmol), 0.58 ml of acetic acid (10.07 mmol) and 666 mg of sodium cyanoborohydride (95% purity, 10.07 mmol) in ethanol (12 ml) were heated to 105° C. in a sealed tube for 2 d. The reaction mixture was allowed to cool to RT, diluted with 3N NaOH solution and extracted with DCM. The combined organic extracts were washed with saturated NaHCO$_3$ solution and brine, dried (Na$_2$SO$_4$), filtered and concentrated in vacuo. After column chromatography (heptane/EtOAc 100:0 to 0:100) 1.688 g (55%) of the title compound were isolated as a brown liquid. MS (ISP) 303.2 (M+H)$^+$.

EXAMPLE S5-C

Preparation of (4-tert-butyl-benzyl)-(2,2-difluoro-2-phenyl-ethyl)-amine a) Preparation of N-(4-tert-butyl-benzyl)-2,2-difluoro-2-phenyl-acetamide (Diethylamino)sulfur trifluoride (1.71 g, 11.2 mmol) was added at RT to neat ethyl benzoyl-formate (1.00 g, 5.61 mmol), then after 16 h excess reagent was destroyed by addition of ice. The reaction mixture was partitioned between ethyl acetate and water, the organic layer washed with sat. aq. sodium hydrogencarbonate solution, dried (MgSO$_4$), and evaporated. To the residue was added 1 M aq. sodium hydroxide solution (7 mL), the slurry was stirred at RT for 24 h, acidified with 1 M aq. hydrochloric acid solution (10 mL), and extracted with tert-butyl methyl ether. The organic layer was washed with brine, dried (MgSO$_4$), and evaporated. The residue was dissolved in DMF (60 mL), then after addition of 4-tert-butylbenzylamine (957 mg, 6.17 mmol), 4-methylmorpholine (1.62 g, 16.8 mmol) and HBTU (3.03 g, 25.3 mmol) the solution was stirred at RT for 16 h. The reaction mixture was then partitioned between water and ethyl acetate, the organic layer was washed with brine, dried (MgSO$_4$), and evaporated. Chromatography (SiO$_2$, heptane-ethyl acetate gradient) afforded the title compound (1.16 g, 69%). White solid, MS (ISP) 318.1 (M+H)$^+$.

b) Preparation of (4-tert-butyl-benzyl)-(2,2-difluoro-2-phenyl-ethyl)-amine

Borane-tetrahydrofuran complex solution (1 M in THF, 1.89 mL, 1.89 mmol) was added at 0° C. to a solution of N-(4-tert-butyl-benzyl)-2,2-difluoro-2-phenyl-acetamide (200 mg, 0.63 mmol) in THF (3.2 mL), then the ice bath was removed and the solution heated to reflux over 16 h. After cooling, the reaction was quenched by careful addition of 1 M aq. hydrochloric acid solution. The reaction mixture was neutralized with aq. sodium hydroxide solution and extracted with DCM. The organic layer was washed with brine, dried (MgSO$_4$), evaporated, and chromatographed (SiO$_2$, heptane-ethyl acetate gradient). The fractions containing the product were concentrated, the residue dissolved in 5% ethanolic sulfuric acid solution (2 mL). This solution was heated at reflux for 2 h, neutralized with 2 M aq. sodium hydroxide solution, and extracted with ethyl acetate. The organic layer was washed with brine, dried (MgSO$_4$), and evaporated to produce the title compound (74 mg, 39%). Light yellow oil, MS (ISP) 304.3 (M+H)$^+$.

EXAMPLE S6-C

Preparation of [2-(4-chloro-phenyl)-ethyl]-(4-pentafluoroethyl-benzyl)-amine

Diisobutylaluminum hydride solution (1 M in hexane, 5.0 mL, 5.0 mmol) was added at 0° C. to a solution of 4-pentafluoroethyl-benzonitrile (1.00 g, 4.52 mmol) in DCM (5 mL), then after 2 h another portion of diisobutylaluminum hydride solution (5 mL) was added and the reaction stirred at RT for 16 h, then carefully poured onto 50% aq. sulfuric acid solution (4 mL). Water (45 mL) was added, and the mixture is extracted three times with DCM. The organic layer was subsequently washed with brine and 1 M potassium sodium tartrate solution, dried (MgSO$_4$), and evaporated. Chromatography (SiO$_2$, heptane-ethyl acetate gradient) afforded crude 4-pentafluoroethyl-benzaldehyde (390 mg) as a yellow liquid, which was added at RT to a solution of 2-(4-chlorophenyl)ethylamine (269 mg, 1.73 mmol) in methanol (2 mL), then after 18 h sodium borohydride (65 mg, 1.73 mmol) was added at 0° C. After 1 h the reaction mixture was partitioned between ether and water, the organic layer was washed with brine, dried (MgSO$_4$), and evaporated. Chromatography (SiO$_2$, heptane-ethyl acetate gradient) afforded the title compound (431 mg, 26%). Light yellow oil, MS (ISP) 364.1 (M+H)$^+$.

EXAMPLE S7-C

Preparation of (4-pentafluoroethyl-benzyl)-[2-(3-trifluoromethyl-phenyl)-ethyl]-amine a) Preparation of 4-pentafluoroethyl-benzylamine A solution of 4-pentafluoroethyl-benzonitrile (1.00 g, 4.52 mmol) in diethyl ether (6.5 mL) was added at RT to a suspension of lithium aluminum hydride (172 mg, 4.52 mmol), then after 30 min the reaction was terminated by careful addition of 1 M aq. potassium sodium tartrate solution. The reaction mixture was extracted three times with tert-butyl methyl ether, the organic layer was extracted with 1 M aq. hydrochloric acid solution, the water layer was basified with 50% aq. sodium hydroxide solution and extracted with tert-butyl methyl ether. The organic layer was washed with brine, dried (MgSO$_4$), and evaporated. Chromatography (SiO$_2$, DCM/methanol/NH$_4$OH 95:5:0.1) afforded the title compound (489 mg, 48%). Yellow-liquid, MS (ISP) 226.1 (M+H)$^+$.

b) Preparation of N-(4-pentafluoroethyl-benzyl)-2-(3-trifluoromethyl-phenyl)-acetamide A solution of 4-pentafluoroethyl-benzylamine (485 mg, 2.16 mmol), 3-(trifluoromethyl)-phenylacetic acid (484 mg, 2.37 mmol), 4-methylmorpholine (654 mg, 6.46 mmol), and HBTU (1.23 g, 3.23 mmol) in DMF (30 mL) was stirred at RT for 16 h, then the reaction mixture was partitioned between water and ethyl acetate. The organic layer was washed with brine, dried (MgSO$_4$), and evaporated. Chromatography (SiO$_2$, heptane-ethyl acetate gradient) afforded the title compound (692 mg, 78%). Light yellow solid, MS (ISP) 412.2 (M+H)$^+$.

c) Preparation of (4-pentafluoroethyl-benzyl)-[2-(3-trifluoromethyl-phenyl)-ethyl]-amine Borane-tetrahydrofuran complex solution (1 M in THF, 2.43 mL, 2.43 mmol) was added at 0° C. to a solution of N-(4-pentafluoroethyl-benzyl)-2-(3-trifluoromethyl-phenyl)-acetamide (200 mg, 0.486 mmol) in THF (3.2 mL), and the homogeneous solution was heated at reflux over 90 min. After cooling, excess reagent was destroyed by careful addition of methanol at 0° C. Volatile material was removed by distillation, then the residue was dissolved in 5% ethanolic sulfuric acid solution (2 mL). The solution was refluxed for 2 h, then partitioned between 2 M aq. sodium hydroxide solution and ethyl acetate. The organic layer was washed with brine, dried (MgSO$_4$), and evaporated. Chromatography (SiO$_2$, heptane-ethyl acetate gradient) afforded the title compound (161 mg, 83%). Colourless oil, MS (ISP) 398.2 (M+H)$^+$.

EXAMPLE S8-C

Preparation of [2-(3-methoxy-phenyl)-ethyl]-(4-pentafluoroethyl-benzyl)-amine

Preparation of N-[2-(3-methoxy-phenyl)-ethyl]-4-pentafluoroethyl-benzamide

A solution of 4-pentafluoroethyl-benzoic acid (500 mg, 2.08 mmol), 2-(3-methoxyphenyl)-ethylamine (361 mg, 2.29 mmol), 4-methylmorpholine (632 mg, 6.24 mmol), and HBTU (1.19 g, 3.12 mmol) in DMF (38 mL) was stirred at RT for 16 h, then the reaction mixture was partitioned between water and ethyl acetate. The organic layer was washed with brine, dried (MgSO$_4$), and evaporated. Chromatography (SiO$_2$, heptane-ethyl acetate gradient) afforded the title compound (746 mg, 96%). Light yellow solid, MS (ISP) 374.2 (M+H)$^+$.

b) Preparation of [2-(3-methoxy-phenyl)-ethyl]-(4-pentafluoroethyl-benzyl)-amine Borane-tetrahydrofuran complex solution (1 M in THF, 9.9 mL, 9.9 mmol) was added at 0° C. to a solution of N-[2-(3-methoxy-phenyl)-ethyl]-4-pentafluoroethyl-benzamide (740 mg, 1.98 mmol) in THF (12 mL), and the homogeneous solution was heated at reflux over 3 h. After cooling, excess reagent was destroyed by careful addition of methanol at 0° C. Volatile material was removed by distillation, then the residue was dissolved in 5% ethanolic sulfuric acid solution (8 mL). The solution was refluxed for 2 h, then partitioned between 2 M aq. sodium hydroxide solution and ethyl acetate. The organic layer was washed with brine, dried (MgSO$_4$), and evaporated. Chromatography (SiO$_2$, DCM/methanol/ NH$_4$OH 95:5:0.1) afforded the title compound (600 mg, 84%). Colourless oil, MS (ISP) 360.1 (M+H)$^+$.

EXAMPLE S9-C

Preparation of (4-tert-butylbenzyl)-[2-(4-chloro-5-methyl-3-trifluoromethyl-pyrazol-1-yl)-ethyl]-amine and (4-tert-butylbenzyl)-[2-(4-chloro-3-methyl-5-trifluoromethyl-pyrazol-1-yl)-ethyl]-amine (S9-C1)

a) Preparation of 2-(4-tert-butylbenzylamino)-ethanol

The title compound was synthesized in analogy to example S3-C using 4-tert-butylbenzaldehyde (1000 mg, 6.17 mmol), ethanolamine (371 µl, 6.17 mmol) and sodium borohydride (350 mg, 9.25 mmol). The desired product (1190 mg, 93%) was isolated without further purification as a colourless oil. MS (ISP) 208.3 (M+H)$^+$.

b) Preparation of 3-(4-tert-butylbenzyl)-[1,2,3]oxathiazolidine 2,2-dioxide

To a solution of 2-(4-tert-butylbenzylamino)-ethanol (1190 mg, 5.74 mmol) and triethylamine (3200 µl, 22.96 mmol) in DCM (15 ml) at −15° C. was added a solution of thionylchloride (544 µl, 7.46 mmol) in DCM (4 ml) over 10 min. The reaction mixture was stirred at −10° C. for 30 min, filtered and the filtrate was concentrated in vacuo. The residue was purified by flash column chromatography to give the desired compound (790 mg, 54%) as a white solid. To a mixture of 3-(4-tert-butylbenzyl)-[1,2,3]oxathiazolidine 2-oxide (790 mg, 3.12 mmol) in DCM (20 ml), acetonitrile (8 ml) and water (8 ml), at 0° C. was added NaIO4 (867 mg, 4.05 mmol) followed by RuO$_2$ (2 mg). The reaction mixture was stirred at 0° C. for 2 h. Water was added and the phases were separated and the aqueous phase was extracted with ethyl acetate. The organic layers were combined washed with brine, dried (MgSO$_4$), and concentrated in vacuo. The residue was then purified by flash column chromatography to give the desired product (640 mg, 76%) as an off white solid. MS (ISP) 287.0 (M+NH$_4$)$^+$.

c) Preparation of (4-tert-butylbenzyl)-[2-(4-chloro-5-methyl-3-trifluoromethyl-pyrazol-1-yl)-ethyl]-amine and (4-tert-butylbenzyl)-[2-(4-chloro-3-methyl-5-trifluoromethyl-pyrazol-1-yl)-ethyl]-amine To a suspension of NaH (58 mg, 1.11 mmol) in THF (10 ml) at 0° C. was added a solution of 4-chloro-5-methyl-3-trifluoromethyl-1H-pyrazole (206 mg, 1.11 mmol) in THF (5 ml) drop wise. The reaction mixture was stirred at 0° C. for 30 min and then 3-(4-tert-butylbenzyl)-[1,2,3]oxathiazolidine 2,2-dioxide (300 mg, 1.11 mmol) was added portion wise. The reaction mixture was warmed to RT and stirred for a further 3 hr after which the reaction mixture was quenched with 5 ml 20% (v/v) H$_2$SO$_4$. The reaction mixture was warmed to 60° C. overnight and then cooled to RT and poured into water. The aqueous phase was made basic with 1N NaOH and then extracted with ethyl acetate. The organic layers were combined, washed with brine, dried over MgSO$_4$, filtered and concentrated in vacuo to give a 7:3 mixture of regioisomers (4-tert-butylbenzyl)-[2-(4-chloro-5-methyl-3-trifluoromethyl-pyrazol-1-yl)-ethyl]-amine (223 mg, 54%) MS (ISP)

374.3 (M+H)⁺ and (4-tert-butylbenzyl)-[2-(4-chloro-3-methyl-5-trifluoromethyl-pyrazol-1-yl)-ethyl]-amine (110 mg, 26%) MS (ISP) 374.3 (M+H)⁺ respectively which were separated by flash column chromatography.

| Example | Name | * | MS (ISP) (M + H)⁺ |
|---|---|---|---|
| S9-C2 | (4-tert-Butyl-benzyl)-[2-(3-trifluoromethyl-phenyl)-ethyl]-amine | S1-C | 336.3 |
| S9-C3 | (4-tert-Butyl-benzyl)-phenethyl-amine | S1-C | 268.3 |
| S9-C4 | (4-tert-Butyl-benzyl)-[2-(3-fluoro-4-trifluoromethyl-phenyl)-ethyl]-amine | S2-C | 354.3 |
| S9-C5 | (4-tert-Butyl-benzyl)-[2-(3-trifluoromethoxy-phenyl)-ethyl]-amine | S2-C | 352.3 |
| S9-C6 | (4-Cyclopropyl-benzyl)-[2-(3-trifluoromethoxy-phenyl)-ethyl]-amine | S2-C | 336.5 |
| S9-C7 | (4-tert-Butyl-benzyl)-[2-(4-chloro-3-trifluoromethyl-phenyl)-ethyl]-amine | S2-C | 370.2 |
| S9-C8 | (4-Cyclopropylbenzyl)-[2-(3-trifluoromethoxyphenyl)-ethyl]-amine | S3-C | 320.2 |
| S9-C9 | (4-tert-Butyl-benzyl)-[2-(3-difluoromethoxy-phenyl)-ethyl]-amine | S2-C | 334.3 |
| S9-C10 | Butyl-(4-tert-butyl-benzyl)-amine | S1-C | 220.4 |
| S9-C11 | (4-tert-Butyl-benzyl)-[2-(3-chloro-4-fluoro-phenyl)-ethyl]-amine | S2-C | 320.3 |
| S9-C12 | (4-tert-Butyl-benzyl)-[2-(2-fluoro-3-trifluoromethyl-phenyl)-ethyl]-amine | S2-C | 354.3 |
| S9-C13 | (4-tert-butyl-benzyl)-[2-(3-chloro-2-fluoro-phenyl)-ethyl]-amine | S2-C | 320.3 |
| S9-C14 | N'-(4-tert-Butyl-benzyl)-N-(4-chloro-phenyl)-N-methyl-ethane-1,2-diamine | S1-C | 368.2 |
| S9-C15 | [4-(1-Methoxycyclopropyl)-benzyl]-[2-(3-trifluoromethylphenyl)-ethyl]-amine | S3-C | 350.4 |
| S9-C16 | (4-Pentafluoro-sulphuranyl-benzyl)-[2-(3,4-dichloro-phenyl)-ethyl]-amine | S1-C | 406.1 |
| S9-C17 | [2-(3,4-Dichloro-phenyl)-ethyl]-[4-(1,2,2,2-tetrafluoro-1-trifluoromethyl-ethyl)-benzyl]-amine | S1-C | 448.0 |
| S9-C18 | [4-(1,2,2,2-Tetrafluoro-1-trifluoromethyl-ethyl)-benzyl]-[2-(3-trifluoromethyl-phenyl)-ethyl]-amine | S1-C | 448.1 |
| S9-C19 | [2-(4-Fluoro-phenyl)-ethyl]-[4-(1,2,2,2-tetrafluoro-1-trifluoromethyl-ethyl)-benzyl]-amine | S1-C | 398.1 |
| S9-C20 | [2-(4-Chloro-phenyl)-ethyl]-[4-(1,2,2,2-tetrafluoro-1-trifluoromethyl-ethyl)-benzyl]-amine | S1-C | 414.3 |
| S9-C21 | (2-Chloro-4-cyclopropyl-benzyl)-[2-(3-trifluoromethyl-phenyl)-ethyl]-amine | S1-C | 354 |
| S9-C22 | (4-Cyclopropyl-2-fluoro-benzyl)-[2-(3-trifluoromethyl-phenyl)-ethyl]-amine | S1-C | 337.9 |
| S9-C23 | (4-Cyclopropyl-3-fluoro-benzyl)-[2-(3-trifluoromethyl-phenyl)-ethyl]-amine | S1-C | 338.0 |
| S9-C24 | (4-Cyclobutyl-benzyl)-[2-(3,4-dichloro-phenyl)-ethyl]-amine | S1-C | 334.4 |
| S9-C25 | (4-Cyclobutyl-benzyl)-[2-(3-trifluoromethyl-phenyl)-ethyl]-amine | S1-C | 334.4 |
| S9-C26 | (4-Cyclobutyl-benzyl)-[2-(4-fluoro-phenyl)-ethyl]-amine | S1-C | 284.4 |
| S9-C27 | [2-(4-Chloro-phenyl)-ethyl]-(4-cyclobutyl-benzyl)-amine | S1-C | 300.4 |
| S9-C28 | (4-Cyclopentyl-benzyl)-[2-(3,4-dichloro-phenyl)-ethyl]-amine | S1-C | 348.4 |
| S9-C29 | (4-Cyclopentyl-benzyl)-[2-(3-trifluoromethyl-phenyl)-ethyl]-amine | S1-C | 348.4 |
| S9-C30 | (4-Cyclopentyl-benzyl)-[2-(4-fluoro-3-trifluoromethyl-phenyl)-ethyl]-amine | S1-C | 366.2 |
| S9-C31 | (4-Cyclobutyl-benzyl)-[2-(4-fluoro-3-trifluoromethyl-phenyl)-ethyl]-amine | S1-C | 352.2 |
| S9-C32 | (4-tert-Butyl-benzyl)-[2-(4-fluoro-phenyl)-ethyl]-amine | S1-C | 286.2 |
| S9-C33 | (4-tert-Butyl-benzyl)-[2-(4-chloro-phenyl)-ethyl]-amine | S1-C | 302.3 |
| S9-C34 | (4-tert-Butyl-benzyl)-[2-(3-chloro-phenyl)-ethyl]-amine | S1-C | 302.3 |
| S9-C35 | (4-Trifluoromethoxy-benzyl)-[2-(3-trifluoromethyl-phenyl)-ethyl]-amine | S1-C | 364 |
| S9-C36 | (4-tert-Butyl-benzyl)-[2-(2-chloro-phenyl)-ethyl]-amine | S1-C | 302.3 |
| S9-C37 | [4-(1-Fluoro-cyclobutyl)-benzyl]-[2-(3-trifluoromethyl-phenyl)-ethyl]-amine | S1-C | 352.4 |
| S9-C38 | [2-(3,4-Dichloro-phenyl)-ethyl]-[4-(1-fluoro-cyclobutyl)-benzyl]-amine | S1-C | 352.3 |
| S9-C39 | [2-(3,4-Dichloro-phenyl)-ethyl]-[4-(1-methoxy-cyclobutyl)-benzyl]-amine | S1-C | 364.3 |
| S9-C40 | [(R)-2-(4-Chloro-phenyl)-2-hydroxy-ethyl]-(4-cyclopropyl-benzyl)-amine | S2-C | 302.2 |

-continued

| Example | Name | * | MS (ISP) (M + H)+ |
|---|---|---|---|
| S9-C41 | (4-tert-Butyl-benzyl)-[2-(5-chloro-pyridin-2-yl)-ethyl]-amine | S4-C | 303.2 |
| S9-C42 | (4-tert-Butyl-benzyl)-[2-(5-trifluoromethyl-pyridin-2-yl)-ethyl]-amine | S4-C | 337.3 |
| S9-C43 | (4-tert-Butyl-benzyl)-[2-(6-trifluoromethyl-pyridin-2-yl)-ethyl]-amine | S4-C | 337.3 |
| S9-C44 | (4-tert-Butyl-benzyl)-[2-(4-trifluoromethyl-pyridin-2-yl)-ethyl]-amine | S4-C | 337.3 |
| S9-C45 | (4-Methyl-benzyl)-[2-(3-trifluoromethyl-phenyl)-ethyl]-amine | S1-C | 294.3 |
| S9-C46 | (4-Ethyl-benzyl)-[2-(3-trifluoromethyl-phenyl)-ethyl]-amine | S1-C | 308.3 |
| S9-C47 | (4-Isopropyl-benzyl)-[2-(3-trifluoromethyl-phenyl)-ethyl]-amine | S1-C | 322.3 |
| S9-C48 | [2-(3,4-Dichloro-phenyl)-ethyl]-(4-isopropyl-benzyl)-amine | S1-C | 322.3 |
| S9-C49 | [2-(4-Chloro-phenyl)-ethyl]-(4-isopropyl-benzyl)-amine | S1-C | 288.1 |
| S9-C50 | (4-Isopropyl-benzyl)-[2-(3-trifluoromethoxy-phenyl)-ethyl]-amine | S2-C | 338.2 |
| S9-C51 | (4-tert-Butyl-benzyl)-(2-naphthalen-2-yl-ethyl)-amine | S1-C | 318.2 |
| S9-C52 | (4-tert-Butyl-benzyl)-(2-phenoxy-ethyl)-amine | S1-C | 284.3 |
| S9-C53 | N-(4-tert-Butyl-benzyl)-N'-(4-chloro-phenyl)-ethane 1,2-diamine | S1-C | 317.2 |
| S9-C54 | [2-(4-Chloro-phenyl)-ethyl]-[4-(1-methoxy-cyclopropyl)-benzyl]-amine | S1-C | 316.0 |
| S9-C55 | [4-(1-Methoxy-cyclopropyl)-benzyl]-[2-(3-trifluoromethoxy-phenyl)-ethyl]-amine | S2-C | 366.0 |
| S9-C56 | (4-Cyclopropyl-benzyl)-[2-(4-fluoro-phenyl)-ethyl]-amine | S1-C | 270.1 |
| S9-C57 | [2-(4-Fluoro-phenyl)-ethyl]-(4-trifluoromethoxy-benzyl)-amine | S1-C | 314.0 |
| S9-C58 | [2-(4-Chloro-phenyl)-ethyl]-(4-trifluoromethoxy-benzyl)-amine | S1-C | 330.2 |
| S9-C59 | (4-tert-Butoxy-benzyl)-[2-(4-chloro-phenyl)-ethyl]-amine | S1-C | 318.0 |
| S9-C60 | (4-tert-Butoxy-benzyl)-[2-(4-fluoro-phenyl)-ethyl]-amine | S1-C | 302.3 |
| S9-C61 | (4-tert-Butoxy-benzyl)-[2-(3-trifluoromethyl-phenyl)-ethyl]-amine | S1-C | 352.2 |
| S9-C62 | (4-tert-Butoxy-benzyl)-[2-(3-trifluoromethoxy-phenyl)-ethyl]-amine | S2-C | 368.3 |
| S9-C63 | [2-(4-Chloro-phenyl)-ethyl]-(4-phenoxy-benzyl)-amine | S1-C | 337.9 |
| S9-C64 | [2-(4-Chloro-phenyl)-ethyl]-(4-trifluoromethyl-benzyl)-amine | S1-C | 313.9 |
| S9-C65 | (4-Benzyloxy-benzyl)-[2-(3-trifluoromethyl-phenyl)-ethyl]-amine | S1-C | 386.3 |
| S9-C66 | [2-(4-Chloro-phenyl)-ethyl]-[4-(1,1,2,2-tetrafluoro-ethoxy)-benzyl]-amine | S1-C | 362.0 |
| S9-C67 | (3-Chloro-4-trifluoromethoxy-benzyl)-[2-(4-fluoro-phenyl)-ethyl]-amine | S1-C | 348.4 |
| S9-C68 | [2-(3-Trifluoromethyl-phenyl)-ethyl]-(4-trimethylsilanyl-benzyl)-amine | S1-C | 352.4 |
| S9-C69 | [2-(4-Chloro-phenyl)-ethyl]-(4-trimethylsilanyl-benzyl)-amine | S1-C | 318.1 |
| S9-C70 | [2-(4-Fluoro-phenyl)-ethyl]-(4-trimethylsilanyl-benzyl)-amine | S1-C | 302.2 |
| S9-C71 | [2-(3,4-Dichloro-phenyl)-ethyl]-(4-trimethylsilanyl-benzyl)-amine | S1-C | 352.2 |
| S9-C72 | [2-(4-Fluoro-phenyl)-ethyl]-(4-pentafluoroethyl-benzyl)-amine | S8-C | 348.2 |
| S9-C73 | (4-Pentafluoroethyl-benzyl)-[2-(3-trifluoromethoxy-phenyl)-ethyl]-amine | S8-C | 414.3 |
| S9-C74 | (4-Pentafluoroethyl-benzyl)-(2-p-tolyl-ethyl)-amine | S8-C | 344.1 |
| S9-C75 | [4-(1-Fluoro-cyclopropyl)-benzyl]-[2-(3-trifluoromethyl-phenyl)-ethyl]-amine | S8-C | 338.2 |
| S9-C76 | [2-(4-Chloro-phenyl)-ethyl]-[4-(1-fluoro-cyclopropyl)-benzyl]-amine | S8-C | 304.1 |
| S9-C77 | (4-tert-butylbenzyl)-[2-(3-trifluoromethyl-pyrazol-1-yl)-ethyl]-amine | S9-C | 326.4 |
| S9-C78 | (4-tert-butylbenzyl)-[2-(5-trifluoromethyl-pyrazol-1-yl)-ethyl]-amine | S9-C | 326.4 |
| S9-C79 | (4-tert-butylbenzyl)-[2-(4-trifluoromethylimidazol-1-yl)-ethyl]-amine | S9-C | 326.3 |
| S9-C80 | (4-tert-butylbenzyl)-[2-(3-phenylpyrazol-1-yl)-ethyl]-amine | S9-C | 334.3 |

-continued

| Example | Name | * | MS (ISP) (M + H)+ |
|---|---|---|---|
| S9-C81 | (4-tert-butylbenzyl)-[2-(4-chloro-3-trifluoromethylpyrazol-1-yl)-ethyl]-amine | S9-C | 360.1 |
| S9-C82 | (4-tert-butylbenzyl)-[2-(5-methyl-3-trifluoromethylpyrazol-1-yl)-ethyl]-amine | S9-C | 340.2 |
| S9-C83 | (4-tert-Butyl-benzyl)-[2-(4-chloro-3-fluoro-phenyl)-ethyl]-amine | S1-C | 320.3 |

*: Prepared in analogy to example

Acids, Esters, Benzo[d][1,3]oxazine-2,4-diones: (Compounds of formula II and IV)

EXAMPLE S1-D

Preparation of 6-chloro-1-methyl-1H-benzo[d][1,3]oxazine-2,4-dione

To a solution of 1 g of 6-chloro-1H-benzo[d][1,3]oxazine-2,4-dione (5.06 mmol) in DMF (20 ml) were carefully added 265 mg of sodium hydride (55% dispersion in oil, 6.07 mmol) at 0° C. and the mixture was stirred at RT for 30 min. Then 0.47 ml of methyl iodide (7.60 mmol) were added and stirring at RT was continued over night. Water was added and the resulting mixture was extracted with ethyl acetate. The combined organic extracts were washed with brine, dried (MgSO$_4$), filtered and concentrated and the remaining residue was purified by crystallization from heptane. This yielded 513 mg of 6-chloro-1-methyl-1H-benzo[d][1,3]oxazine-2,4-dione (48%) as an off-white solid. $^{1H}$NMR (DMSO-d$_6$, 300 MHz): δ 3.45 (s, 3H), 7.47 (d, J=8.9 Hz, 1H), 7.89 (dd, J=8.9 and 2.7 Hz, 1H), 7.95 (d, J=2.7 Hz, 1H).

EXAMPLE S2-D

Preparation of 5-chloro-2-methylamino-benzoic acid

A suspension of 3.955 g of 6-chloro-1-methyl-1H-benzo[d][1,3]oxazine-2,4-dione (18.69 mmol) in 37 ml of 2N KOH was heated to 100° C. for 4 h. The clear solution was then allowed to cool to RT and the pH was adjusted to 6-7 by addition of 3N HCl. The precipitate formed was filtered off and dried to give 3.31 g (95%) of the title compound as a yellow solid. MS (ISP) 183.9 (M–H)$^-$.

EXAMPLE S3-D

Preparation of 6-chloro-1-ethyl-1H-benzo[d][1,3]oxazine-2,4-dione

The title compound was prepared in analogy to of 6-chloro-1-methyl-1H-benzo[d][1,3]-oxazine-2,4-dione described in example S1-D. $^{1H}$NMR (DMSO-d$_6$, 300 MHz): δ 1.21 (t, J=7.1 Hz, 3H), 4.05 (q, J=7.1 Hz, 2H), 7.54 (d, J=9.0 Hz, 1H), 7.88 (dd, J=9.0 and 2.6 Hz, 1H), 7.96 (d, J=2.6 Hz, 1H).

EXAMPLE S4-D

Preparation of 5-chloro-2-ethylamino-benzoic acid

The title compound was prepared in analogy to 5-chloro-2-methylamino-benzoic acid described in example S2-D.

$^{1H}$NMR (DMSO-d$_6$, 300 MHz): δ 1.13 (t, J=7.2 Hz, 3H), 3.13 (d, J=7.2 Hz, 2H), 6.69 (d, J=8.9 Hz, 1H), 7.32 (dd, J=8.9 and 2.7 Hz, 1H), 7.64 (d, J=2.7 Hz, 1H).

EXAMPLE S5-D

Preparation of 5-chloro-2-isopropylamino-benzoic acid a) Preparation of 2-amino-5-chlorobenzoic acid methyl ester To a suspension of 6-chloro-1H-benzo[d][1,3]oxazine-2,4-dione (10 g, 50.61 mmol) in methanol (200 ml) was added DMAP (615 mg, 5.03 mmol) and the reaction mixture was heated to reflux for 3 h. The reaction mixture was cooled to RT and concentrated in vacuo. The residue was dissolved in EtOAc and washed with 0.1M HCl solution (3×), brine, dried over MgSO$_4$, filtered and concentrated in vacuo to give the desired product (9.25 g, 97%) as a white solid which did not require further purification. $^{1H}$ NMR (DMSO-d$_6$, 300 MHz): δ 7.64 (d, J=2.5 Hz, 1H), 7.30 (dd, J=2.5 and 9.0 Hz, 1H), 6.82 (d, J=9.0 Hz, 1H), 6.78 (br s, 2H), 3.79 (s, 3H).

b) Preparation of 5-chloro-2-isopropylamino-benzoic acid methyl ester

To a solution of 500 mg of 2-amino-5-chlorobenzoic acid methyl ester (2.69 mmol) were added slowly 380 µl of 2-methoxypropene (4.04 mmol), 154 µl of acetic acid (2.69 mmol) and 951 mg of sodium triacetoxyborohydride (4.04 mmol). The reaction mixture was stirred at RT for 3.5 d, then 1N NaOH solution was added and the mixture was extracted with DCM. The combined organic extracts were washed with brine, dried (MgSO$_4$), filtered and concentrated in vacuo. The remaining residue was purified by column chromatography (silica gel; heptane 100% to heptane/EtOAc 9:1) to give 488 mg (80%) of a yellow liquid. MS (ISP) 228.1 (M+H)$^+$.

c) Preparation of 5-chloro-2-isopropylamino-benzoic acid

To a solution of 480 mg of 5-chloro-2-isopropylamino-benzoic acid methyl ester in methanol (5 ml) were added 3.16 ml of a 1N NaOH solution and the mixture was stirred for 4 d at RT. Then the reaction mixture was concentrated in vacuo and the remaining residue dissolved in water. The resulting solution was washed with ethyl acetate and then the pH was adjusted to 1 with 1N HCl solution and the mixture was extracted with ethyl acetate. The combined organic extracts were dried (MgSO$_4$), filtered and concentrated to give the title compound as an off-white solid (429 mg, 95%). NMR (CDCl$_3$, 300 MHz): δ 1.27 (d, J=6.3 Hz, 6H), 3.70 (sept, J=6.3 Hz, 1H), 6.65 (d, J=9.1 Hz, 1H), 7.31 (dd, J=9.1 and 2.7 Hz, 1H), 7.92 (d, J=2.7 Hz, 1H).

EXAMPLE S6-D

Preparation of 5-chloro-2-methylamino-nicotinic acid

A mixture of 2,5-dichloronicotinic acid (1.76 g, 9.17 mmol), 41% aq. methylamine solution (7 mL), and 1,4-dioxane (6 mL) was heated at 160° C. under microwave irradiation for 20 min. After cooling, volatile material was distilled off, and the residue was dissolved in water (30 mL) and acidified to pH 3 by addition of 37% aq. hydrochloric acid solution. The precipitate was collected by filtration and triturated in DCM to produce the title compound (1.60 g, 92%). Off-white solid, MS (ISP): 187.1 (M+H)$^+$.

EXAMPLE S7-D

Preparation of 6-chloro-3-methylamino-pyridine-2-carboxylic acid

A mixture of 2-chloro-5-fluoropyridine-6-carboxylic acid (2.00 g, 11.4 mmol), 41% aq. methylamine solution (8 mL) and 1,4-dioxane (8 mL) was heated at 125° C. under microwave irradiation for 60 min. After cooling, volatile material was distilled off, and the residue was dissolved in water (20 mL) and acidified to pH 3 by addition of 37% aq. hydrochloric acid solution. The precipitate was collected by filtration to produce the title compound (1.85 g, 87%). Light yellow solid, MS (ISP): 185.1 (M−H)$^-$.

EXAMPLE S8-D

Preparation of 6-chloro-3-methylamino-pyridazine-4-carboxylic acid

41% aq. methylaminine solution (2 mL) was added at RT to a solution of 3,6-dichloro-pyridazinecarboxylic acid (500 mg, 2.59 mmol) in 1,4-dioxane (2 mL). The reaction mixture was stirred at RT for 5 h, then evaporated to dryness. The residue was dissolved in water (5 mL) and acidified to pH 3 by addition of 37% aq. hydrochloric acid solution. The precipitate was collected by filtration to produce the title compound (321 mg, 66%). White solid, MS (EI): 187.1 (M$^+$).

EXAMPLE S9-D

Preparation of 3-methylamino-pyridazine-4-carboxylic acid

A mixture of 6-chloro-3-methylamino-pyridazine-4-carboxylic acid (60 mg, 0.32 mmol), sodium hydroxide (50 mg, 1.3 mmol), palladium (10% on activated charcoal, 12 mg), and ethanol (3 mL) was hydrogenated at atmospheric pressure for 48 h, then acidified to pH 7 by addition of 37% aq. hydrochloric acid solution. After removal of insoluble material by filtration, the filtrate was evaporated and dried to give a white solid (76 mg), which contained the title compound and sodium chloride. MS (ISP): 154.1 (M+H)$^+$.

EXAMPLE S10-D

Preparation of 6-methoxy-3-methylamino-pyridazine-4-carboxylic acid

A solution of 6-chloro-3-methylamino-pyridazine-4-carboxylic acid (80 mg, 0.43 mmol), sodium methoxide solution (5.4 M in methanol, 1.0 mL, 5.4 mmol) in methanol (1 mL) was heated at 170° C. for 20 min. After cooling, the solution was evaporated, the residue dissolved in water (2 mL) and acidified to pH 3 by addition of 37% aq. hydrochloric acid solution. The precipitate was collected by filtration to afford the title compound (17 mg, 22%). White solid, MS (ISP): 182.1 (M−H)$^-$.

EXAMPLE S11-D

Preparation of 2-chloro-5-methylamino-isonicotinic acid a) Preparation of 5-(tert-butoxycarbonyl-methyl-amino)-2-chloro-isonicotinic acid n-Butyllithium solution (1.6 M in hexane, 6.78 mL, 10.8 mmol) was added at −78° C. to a solution of (6-chloro-4-iodo-pyridin-3-yl)-methyl-carbamic acid tert-butyl ester (synthesized according to WO 2005002577; 2.00 g, 5.43 mmol) in THF (40 mL). After 15 min the solution was purged with carbon dioxide gas for 15 min, then allowed to reach RT. The reaction mixture partitioned between hexane and water and the organic layer was extracted with 1% aq. ammonia solution. The combined aqueous layer was washed with hexane/ethyl acetate 1:1, and the pH was set to 4 by addition of 1 M aq. hydrochloric acid solution. The precipitate was collected by filtration and washed with water, to afford 5-(tert-butoxycarbonyl-methyl-amino)-2-chloro-isonicotinic acid (1.28 g, 83%). Yellow solid, MS (ISP): 287.1 (M+H)$^+$.

b) Preparation of 2-chloro-5-methylamino-isonicotinic acid 5-(tert-Butoxycarbonyl-methyl-amino)-2-chloro-isonicotinic acid (1.04 g, 3.63 mmol) was converted into 2-chloro-5-methylamino-isonicotinic acid (625 mg, 92%) by heating at 240° C. in a Kugelrohr apparatus for 10 min. Yellow solid, MS (ISP): 187.1 (M+H)$^+$.

EXAMPLE S12-D

Preparation of 6-chloro-3-methylamino-pyrazine-2-carboxylic acid

A solution of 3,6-dichloro-pyrazine-2-carboxylic acid methyl ester (synthesized according to GB1082060; 210 mg, 1.01 mmol) in methanol (1.1 mL) was treated at 0° C. with 1 M sodium hydroxide solution (1.1 mL, 1.1 mmol) and stirred for 1 h at 0° C., then partitioned between ethyl acetate and 1 M hydrochloric acid solution. The organic layer was washed with brine, dried (MgSO$_4$), and evaporated. The residue was dissolved in 1,4-dioxane (0.78 mL), treated with 41% aq. methylamine solution, and the mixture was heated at 50° C. for 16 h, then partitioned between ethyl acetate and 0.5 M citric acid solution. The organic layer was washed with brine, dried (MgSO$_4$), and evaporated. The residue was triturated in water to produce the title compound (111 mg, 58%). Yellow solid, MS (ISP): 186.0 (M−H)⁻.

EXAMPLE S13-D

Preparation of 5-bromo-2-methylamino-nicotinic acid ethyl ester

A suspension of 5-bromo-2-methylamino-nicotinic acid (1.00 g, 4.33 mmol) in 15% ethanolic sulfuric acid solution (15 mL) was heated at reflux for 16 h, then poured onto ice, basified to pH 10 with 1 M aq. sodium carbonate solution and extracted with ethyl acetate. The organic layer was washed with brine, dried (MgSO$_4$), and evaporated. Chromatography (SiO$_2$, heptane-ethyl acetate gradient) afforded the title compound (929 mg, 83%). Light brown solid, MS (ISP): 259.2 (M+H)⁺.

EXAMPLE S14-D

Preparation of 2-methylamino-5-vinyl-nicotinic acid ethyl ester

A solution of 5-bromo-2-methylamino-nicotinic acid ethyl ester (100 mg, 0.39 mmol), lithium chloride (98 mg, 2.32 mmol), copper(I)chloride (191 mg, 1.93 mmol), vinyl tributyl tin (151 mg, 0.46 mmol), and tetrakis(triphenylphosphine)palladium(0) (45 mg, 39 μmol) in methyl sulfoxide (3.1 mL) was stirred at 65° C., then after 4 h another portion of vinyl tributyl tin (141 mg, 0.46 mmol) was added, and stirring was continued for 18 h. After cooling, the reaction mixture was partitioned between sat. aq. ammonium chloride solution and diethyl ether, the organic layer was washed with water, dried (MgSO$_4$), and evaporated. Chromatography (SiO$_2$, heptane-ethyl acetate gradient) afforded the title compound (72 mg, 91%). Yellow liquid, MS (ISP): 207.1 (M+H)⁺.

EXAMPLE S15-D

Preparation of 2-methylamino-5-phenyl-nicotinic acid ethyl ester

A mixture of 5-bromo-2-methylamino-nicotinic acid ethyl ester (100 mg, 0.39 mmol), potassium carbonate (160 mg, 1.16 mmol), dichloro[1,1'-bis(diphenylphosphine)ferrocene]palladium(II); (28 mg, 39 μmol) and phenylboronic acid (146 mg, 1.16 mmol), 1,4-dioxane (0.9 mL), and water (0.11 mL) was heated at reflux for 3 h, then partitioned between ethyl acetate and sat. aq. ammonium chloride solution. The organic layer was washed with brine, dried (MgSO$_4$), and evaporated. Chromatography (SiO$_2$, heptane-ethyl acetate gradient) afforded the title compound (44 mg, 44%). Yellow liquid, MS (EI): 256.2 (M⁺).

EXAMPLE S16-D

Preparation of 5-ethyl-2-methylamino-nicotinic acid ethyl ester

A solution of 5-bromo-2-methylamino-nicotinic acid ethyl ester (400 mg, 1.54 mmol), diethylzinc solution (1 M in hexane, 3.1 mL, 3.1 mmol), and dichloro[1,1'-bis(diphe-nylphosphine)ferrocene]palladium(II) (34 mg, 46 μmol) in 1,4-dioxane was heated at reflux for 2 h, then partitioned between ethyl acetate and sat. aq. ammonium chloride solution. The organic layer was washed with brine, dried (MgSO$_4$), and evaporated. Chromatography (SiO$_2$, heptane-ethyl acetate gradient) afforded the title compound (48 mg, 15%). Colourless liquid, MS (ISP): 209.3 (M+H)⁺.

EXAMPLE S17-D

Preparation of 2-cyclopropylamino-5-trifluoromethyl-benzoic acid 1 g of 2-fluoro-5-trifluoromethyl-benzoic acid (4.81 mmol) was dissolved in DCM (10 ml) and 1.03 ml of oxalyl-chloride (12.01 mmol) and a drop of DMF were added at RT. The mixture was stirred for 1 h before all volatile materials were removed in vacuo. The remaining residue was again dissolved in DCM (10 ml) and 1.4 ml of ethanol was added. After 1 h the reaction mixture was diluted with DCM and then washed with 10% aqueous KHCO$_3$ solution, water and brine, dried (MgSO$_4$), filtered and concentrated. The remaining material was dissolved in DMSO (6 ml), 5.57 ml of cyclopropylamine (79.4 mmol) were added and the mixture was heated to 110° C. over night in a sealed tube. The reaction mixture was then cooled to RT, diluted with ethyl acetate, washed with diluted HCl, 10% aqueous KHCO$_3$ solution, water and brine, dried (MgSO$_4$), filtered and concentrated. Then THF (20 ml), methanol (10 ml) and 8 ml of a 1N LiOH solution were added and the resulting solution was stirred over night at RT. The organic solvents were then removed in vacuo and the solution was acidified with 1N HCl and extracted with ethyl acetate. The combined organic extracts were dried (MgSO$_4$), filtered and concentrated. The remaining solid was triturated with a small amount of chloroform. Filtration gave 391 mg (33%) of the title compound as light brown crystals. $^1H$NMR (DMSO-d$_6$, 300 MHz): δ 0.53 (m, 2H), 0.85 (m, 2H), 2.56 (m, 1H), 7.24 (d, J=8.9 Hz, 1H), 7.71 (dd, J=8.9 and 2.1 Hz, 1H), 8.02 (s, 1H), 8.30 (br s, 1H), 13.21 (br s, 1H).

EXAMPLE S18-D

Preparation of 5-chloro-2-cyclopropylamino-benzoic acid

To a solution of 500 mg of 2-amino-5-chloro-benzoic acid (2.91 mmol) in methanol were added 3 Å molecular sieves, 2.34 ml of [(1-ethoxycyclopropyl)oxy]trimethylsilane (11.66 mmol) and 1.67 ml of acetic acid and the mixture was stirred for 30 min at RT. Then 916 mg of sodium cyanoborohydride (14.57 mmol) were added and the reaction mixture was heated to reflux for 16 h. The reaction mixture was allowed to cool to RT, filtered and the filtrate was concentrated in vacuo. The remaining solid was dissolved in ethyl acetate and the solution was washed with 1N HCl and brine, dried (MgSO$_4$), filtered and concentrated to give 312 mg of the crude title compound that was used in the following step without further purification. $^1H$NMR (DMSO-d$_6$, 300 MHz): δ 0.46 (m, 2H), 0.79 (m, 2H), 3.44 (m, 1H), 7.10 (d, J=8.9 Hz, 1H), 7.44 (d, J=8.9 Hz, 1H), 7.70 (s, 1H), 7.89 (br s, 1H), 13.09 (br s, 1H).

EXAMPLE S19-D

Preparation of potassium;
3-methylamino-thiophene-2-carboxylate a) Preparation of 3-(2,2,2-trifluoro-acetylamino)-thiophene-2-carboxylic acid methyl ester To a solution of 2 g of methyl 3-amino-thiophene-2-carboxylic acid methyl ester (12.6 mmol) in DCM (20 ml) were slowly added 2.68 ml of trifluoroacetic acid anhydride (18.9 mmol) and 3.04 ml of pyridine (37.8 mmol) at −10° C. The reaction mixture was stirred for 1 h at RT, poured into a mixture of ice and 1N HCl and then extracted with DCM. The combined organic extracts were washed with brine, dried ($Na_2SO_4$), filtered and concentrated in vacuo. The remaining residue was purified by column chromatography (silica gel; heptane 100% to heptane/EtOAc 9:1) to give 3.019 g (95%) of 3-(2,2,2-trifluoro-acetylamino)-thiophene-2-carboxylic acid methyl ester a white solid. MS (ISP) 252.1 (M−H)⁻.

b) Preparation of 3-[methyl-(2,2,2-trifluoro-acetyl)-amino]-thiophene-2-carboxylic acid methyl ester A mixture of 2 g of 3-(2,2,2-trifluoro-acetylamino)-thiophene-2-carboxylic acid methyl ester (7.9 mmol), 1.31 g of potassium carbonate (9.48 mmol) and 596 µl of methyl iodide (9.48 mmol) in DMF (7.5 ml) was stirred for 2 d. The reaction mixture was then poured into water and extracted with DCM. The combined organic extracts were washed with water and brine, dried ($Na_2SO_4$), filtered and concentrated in vacuo to give 2.055 g (97%) of 3-[methyl-(2,2,2-trifluoro-acetyl)-amino]-thiophene-2-carboxylic acid methyl ester as a white solid. MS (ISP) 268.1 (M+H)⁺.

c) Preparation of 3-methylamino-thiophene-2-carboxylic acid methyl ester

A solution of 2.05 g of 3-[methyl-(2,2,2-trifluoro-acetyl)-amino]-thiophene-2-carboxylic acid methyl ester (7.67 mmol) in a mixture of methanol (100 ml) and 1N NaOH (15.4 ml) was stirred at RT over night. The methanol was then removed in vacuo and the remaining mixture was diluted with water and extracted with ethyl acetate. The combined organic layers were washed with brine, dried ($Na_2SO_4$), filtered and concentrated in vacuo to give 1.236 g (94%) of 3-methylamino-thiophene-2-carboxylic acid methyl ester as a light brown solid. MS (ISP) 172.2 (M+H)⁺.

d) Preparation of potassium; 3-methylamino-thiophene-2-carboxylate

To a solution of 230 mg of 3-methylamino-thiophene-2-carboxylic acid methyl ester (1.34 mmol) in methanol (4 ml) was added a solution of 262 mg of potassium hydroxide in 322 µl of water and the mixture was heated to reflux for 1.5 d. The reaction mixture was then concentrated in vacuo and the remaining residue was dried. This gave 399 mg of a light brown solid containing the crude title compound (contaminated with excess of potassium hydroxide) that was used in the following step without further purification. MS (ISP) 156.0 (M−H)⁻.

EXAMPLE S20-D

Preparation of lithium 5-cyclopropylamino-thiazole-4-carboxylate a) Preparation of 5-cyclopropylamino-thiazole-4-carboxylic acid ethyl ester

To a vigorously stirred solution of 311 mg of potassium tert-butylate (2.77 mmol) in THF (5 ml) were slowly added 5 ml of a THF-solution of 300 mg of ethyl isocyanoacetate (2.52 mmol) and 250 mg of cyclopropyl isothiocyanate (2.52 mmol) at −20° C. The mixture was stirred for 15 min at −20° C. and was then allowed to warm to 0° C. in 1.5 h before 0.3 ml of acetic acid were added. The reaction mixture was concentrated in vacuo to give a residue which was purified by flash column chromatography (heptane/ethyl acetate 95:5 to 75:25) to give 5-cyclopropylamino-thiazole-4-carboxylic acid ethyl ester (198 mg, 37%) as a yellow oil. MS (ISP) 213.1 (M+H)⁺.

b) Preparation of lithium 5-cyclopropylamino-thiazole-4-carboxylate 198 mg of 5-cyclopropylamino-thiazole-4-carboxylic acid ethyl ester (0.93 mmol) were dissolved in a 3:1 mixture of THF/methanol (2 ml) and 1.4 ml of a 1N LiOH-solution were added. The reaction mixture was stirred at RT for 3 days, then concentrated in vacuo and the remaining residue was dried. This gave 191 mg of a yellow solid containing the crude title compound (contaminated with excess of lithium hydroxide) that was used in the following step without further purification. MS (ISP) 182.9 (M−H)⁻.

EXAMPLE S21-D

Preparation of 5-cyclopropylamino-3-methyl-isothiazole-4-carboxylic acid ethyl ester a) Preparation of 3-amino-2-cyclopropylthiocarbamoyl-but-2-enoic acid ethyl ester A mixture of 2.03 ml of ethyl 3-aminocrotonate (16 mmol) and 1.59 g of cyclopropyl iso-thiocyanate (16 mmol) was heated to 100° C. for 5 h. The reaction mixture was then cooled to 0° C. and diethyl ether (5 ml) and a small amount of heptane were added. An oily precipitate formed and after 5 min the solvents were decanted off. The remaining residue was triturated with a small amount of diethyl ether at 0° C. The precipitate was then filtered off and dried to give 1.64 g (45%) of 3-amino-2-cyclopropylthiocarbamoyl-but-2-enoic acid ethyl ester as a yellow solid. $^1H$NMR (DMSO-$d_6$, 300 MHz): δ 0.60 (m, 2H), 0.76 (m, 2H), 1.11 (t, J=7.1 Hz, 3H), 1.90 (s, 3H), 3.28 (m, 1H), 3.97 (q, J=7.1 Hz, 2H), 7.24 (br s, 1H), 8.21 (br s, 1H), 9.79 (d, J=5.5 Hz, 1H).

b) Preparation of 5-cyclopropylamino-3-methyl-isothiazole-4-carboxylic acid ethyl ester To a vigorously stirred solution of 1 g of 3-amino-2-cyclopropylthiocarbamoyl-but-2-enoic acid ethyl ester (4.4 mmol) in chloroform (16 ml) was added dropwise a solution of 1.4 g of bromine in chloroform (8 ml) at 0° C. After completion of the addition the reaction mixture was stirred at 0° C. for additional 5 min. Then diethyl ether and sat. $NaHCO_3$-solution were added and the mixture was extracted with diethyl ether. The combined extracts were washed with brine, dried ($Na_2SO_4$), filtered and concentrated in vacuo to give a residue which was purified by flash column chromatography (100% DCM) to give 5-cyclopropylamino-3-methyl-isothiazole-4-carboxylic acid ethyl ester (410 mg, 40%) as a brown liquid. $^{1H}$NMR ($CDCl_3$, 300 MHz): δ 0.73 (m, 2H), 0.81 (m, 2H), 1.36 (t, J=7.2 Hz, 3H), 2.50 (s, 3H), 2.63 (m, 1H), 4.29 (q, J=7.2 Hz, 2H), 7.80 (br s, 1H).

EXAMPLE S22-D

Preparation of potassium; 3-ethylamino-5-methyl-isoxazole-4-carboxylate

To a solution of 46 mg of 3-ethylamino-5-methyl-isoxazole-4-carboxylic acid ethyl ester (0.23 mmol) [synthesized as described in Synthesis 1988, 203] were added 0.46 ml of a 1N KOH-solution and the mixture was heated to 80° C. for 2 h and then to 60° C. over night. Then all volatile materials were removed in vacuo to give 54 mg of a white solid containing the crude title compound (contaminated with excess of potassium hydroxide) that was used in the following step without further purification. $^{1H}$NMR (DMSO-$d_6$, 300 MHz): δ 1.12 (t, J=7.1 Hz, 3H), 2.37 (s, 3H), 3.07 (m, 2H), 6.83 (t, J=5.5 Hz, 1H).

EXAMPLE S23-D

Preparation of potassium; 1,3-dimethyl-5-methylamino-1H-pyrazole-4-carboxylate a) Preparation of 3-methyl-5-methylamino-1H-pyrazole-4-carboxylic acid ethyl ester A mixture of 1 g of 4-methylthiosemicarbazide (9.51 mmol) and 1.565 g of ethyl-2-chloro-acetoacetate (9.51 mmol) in THF (20 ml) was stirred for 30 min at RT and then heated to reflux for 1 h. The yellow solid that precipitated was filtered off, washed with acetone and then dissolved in hot (95° C.) water. The precipitating sulfur was filtered off, the aqueous solution was cooled to 0° C., vigorously stirred and 5 ml of an aqueous ammonium hydroxide solution (25%) were added. A white precipitate formed and the suspension was stirred for an additional hour at RT. The precipitate was then filtered off and dried to give 1.04 g (60%) of 3-methyl-5-methylamino-1H-pyrazole-4-carboxylic acid ethyl ester as a white solid. MS (ISP) 184.1 (M+H)$^+$.

b) Preparation of 1,3-dimethyl-5-methylamino-1H-pyrazole-4-carboxylic acid ethyl ester To a solution of 100 mg of 3-methyl-5-methylamino-1H-pyrazole-4-carboxylic acid ethyl ester (0.55 mmol) in methanol (5 ml) were added 52 mg of sodium hydroxide (1.3 mmol) and 77 mg of iodomethane (0.54 mmol) and the mixture was stirred at RT over night. The reaction mixture was then concentrated in vacuo at low temperature and 33 mg (31%) of 1,3-dimethyl-5-methylamino-1H-pyrazole-4-carboxylic acid ethyl ester were isolated from the remaining solid by HPLC (reversed phase, MeCN/water 20:80 to 50:50). MS (ISP) 198.2 (M+H)$^+$.

c) Preparation of potassium; 1,3-dimethyl-5-methylamino-1H-pyrazole-4-carboxylate To a solution of 33 mg (0.17 mmol) 1,3-dimethyl-5-methylamino-1H-pyrazole-4-carboxylic acid ethyl ester in THF (0.5 ml) were added 330 μl of 1N potassium hydroxide solution. The mixture was heated to 50° C. for 3 h and then to reflux for 3 h. Then all volatile materials were removed in vacuo to give a solid containing the crude title compound (contaminated with excess of potassium hydroxide) that was used in the following step without further purification. MS (ISP) 168.1 (M−H)$^-$.

EXAMPLE S24-D

Preparation of 2-amino-5-chloro-3-iodo-benzoic acid a) Preparation of 2-amino-5-chloro-3-iodo-benzoic acid methyl ester To a solution of 2-amino-5-chlorobenzoic acid methyl ester (1.10 g, 5.93 mmol) in acetic acid (20 ml) was added N-iodosuccinimide (1.47 g, 6.52 mmol) in small portions and the reaction mixture was stirred overnight at RT. The reaction mixture was diluted with ethylacetate and washed with 1N NaOH solution, $Na_2S_2O_3$ solution, and brine, dried ($MgSO_4$), filtered and concentrated in vacuo to give a residue which was purified by flash column chromatography (EtOAc/cyclohexane 1:9-1:4) to give the desired iodide (1.64 g, 89%) as a cream coloured solid. $^{1H}$NMR (DMSO-d6, 300 MHz): δ 7.93 (d, J=2.5 Hz, 1H), 7.76 (d, J=2.5 Hz, 1H), 6.73 (br s, 2H), 3.83 (s, 3H).

b) Preparation of 2-amino-5-chloro-3-iodo-benzoic acid

The title compound was prepared in analogy to 5-chloro-2-isopropylamino-benzoic acid described in example S5-D. $^{1H}$-NMR ($CDCl_3$, 300 MHz): δ 7.94 (d, J=2.5 Hz, 1H), 7.83 (d, J=2.5 Hz, 1H), 6.40 (br s, 2H).

EXAMPLE S25-D

Preparation of 5-chloro-3-fluoro-2-methylaminobenzoic acid a) Preparation of 3-fluoro-2-methylaminobenzoic acid ethyl ester To a solution of 8-fluoro-1H-benzo[d][1,3]oxazine-2,4-dione (200 mg, 1.10 mmol) in DMF (2 ml) was added $Na_2CO_3$ (129 mg, 1.22 mmol), followed by methyl iodide (104 μl, 1.66 mmol) and the reaction mixture was stirred at RT for 18 h. The reaction mixture was diluted with ethyl acetate and the mixture was washed with water and brine. The organic phase was dried ($MgSO_4$), filtered and concentrated in vacuo to give 8-fluoro-1-methyl-1H-benzo[d][1,3]oxazine-2,4-dione (190 mg, 88%) which was not purified due to its poor solubility but directly used in the following step without further purification. To a suspension of the residue (190 mg, 0.97 mmol) in ethanol (4 ml) was added DMAP (12 mg, 0.09 mmol) and the reaction mixture was heated to reflux for 3 h. The reaction mixture was cooled to RT and then concentrated in vacuo to give a residue which was partitioned between ethyl acetate and 0.1M HCl solution. The organic phase was washed with brine, dried over MgSO$_4$, filtered and concentrated in vacuo. The residue was purified by flash column chromatography to give the desired product (132 mg, 69%) as a light yellow oil. $^1$H NMR (CDCl$_3$, 300 MHz): 7.69 (aptd, J=8.0 Hz, 1H), 7.50 (brds, 1H), 7.08 (ddd, J=14.0, 8.0, 1.5 Hz, 1H), 6.51 (aptdt, J=8.0, 4.5 Hz, 1H), 4.31 (q, J=7.0 Hz, 2H), 3.12 (m, 3H), 1.37 (t, J=7.0 Hz, 3H).

b) Preparation of 5-chloro-3-fluoro-2-methylaminobenzoic acid ethyl ester

To a solution of 3-fluoro-2-methylaminobenzoic acid ethyl ester (124 mg, 0.63 mmol) in acetic acid (4 ml) was added 1,3-dichloro-5,5-dimethylhydantoin (93 mg, 0.47 mmol). The reaction mixture was stirred at RT for 3 h. The mixture was diluted with ethyl acetate and then washed with sat. NaHCO$_3$. The organic phase was then washed with brine, dried (MgSO$_4$), filtered, and concentrated in vacuo to give a residue which was purified by flash column chromatography to give 5-chloro-3-fluoro-2-methylaminobenzoic acid ethyl ester (135 mg, 93%) as a yellow oil. $^1$H NMR (CDCl$_3$, 300 MHz): 7.67 (dd, J=2.5, 1.5 Hz, 1H), 7.52 (brds, 1H), 7.09 (dd, J=13.5, 2.5 Hz, 1H), 4.31 (q, J=7.0 Hz, 2H), 3.11 (m, 3H), 1.38 (t, J=7.0 Hz, 3H).

c) Preparation of 5-chloro-3-fluoro-2-methylaminobenzoic acid

To a solution of 5-chloro-3-fluoro-2-methylaminobenzoic acid ethyl ester (135 mg, 0.58 mmol) in MeOH was added 1N NaOH (1165 µl, 1.17 mmol) and the reaction mixture was refluxed for 2 h. The reaction mixture was diluted with ethyl acetate and water and then extracted. The aqueous layer was acidified to pH3 using 1N HCl and the aqueous layer was extracted with EtOAc (2×). The organic layer was dried (MgSO$_4$), filtered and concentrated in vacuo to give the desired product (110 mg, 93%) which did not require further purification. MS (ISP) 202.1 (M−H)$^-$.

EXAMPLE S26-D

Preparation of 2-acetylamino-5-chloro-3-fluoro-benzoic acid a) Preparation of 5-chloro-2-diacetylamino-3-fluorobenzoic acid ethyl ester Acetic anhydride was added to 2-amino-5-chloro-3-fluoro-benzoic acid ethyl ester (synthesized in analogy to a procedure described in example S25-D (230 mg, 1.06 mmol) followed by pyridine (213 µl, 2.64 mmol) and DMAP (65 mg, 0.53 mmol). The reaction mixture was heated to 65° C. for 4 h. The reaction mixture was quenched with 1N HCl and then extracted with ethyl acetate. The organic layers were combined, washed with sat. NaHCO$_3$ and brine, dried (MgSO$_4$), filtered and concentrated in vacuo to give a residue which was purified by flash column chromatography to the desired product (185 mg, 58%) as a colourless liquid. $^1$H NMR (CDCl$_3$, 300 MHz): 7.89 (aptt, J=2.0 Hz, 1H), 7.43 (dd, J=8.5, 2.5 Hz, 1H), 4.33 (q, J=7.0 Hz, 2H), 2.30 (s, 6H), 1.35 (t, J=7.0 Hz, 3H).

b) Preparation of 2-acetylamino-5-chloro-3-fluoro-benzoic acid

To a solution of 5-chloro-2-diacetylamino-3-fluorobenzoic acid ethyl ester (185 mg, 0.61 mmol) in MeOH (4 ml) was added 1N NaOH (1288 µl, 1.29 mmol) and the reaction mixture was refluxed for 2 h. The reaction mixture was cooled to RT and then diluted with ethyl acetate and water. The organic phase was separated and the aqueous phase was made acidic with 1N HCl to pH3 and then extracted with ethyl acetate (2×). The organic layer was dried (MgSO$_4$), filtered and concentrated in vacuo to give the desired product (130 mg, 92%) as a white solid which did not require further purification. MS (ISP) 230.1 (M−H)$^-$.

EXAMPLE S27-D

Preparation of 5-chloro-6-fluoro-1-methyl-1H-benzo[d][1,3]oxazine-2,4-dione

To a suspension of NaH (49 mg, 1.11 mmol) in DMF (2 ml) at RT was added a solution of 5-chloro-6-fluoro-1H-benzo[d][1,3]oxazine-2,4-dione (synthesized in analogy to a procedure described in EP 59391) (200 mg, 0.93 mmol) in DMF (2 ml). The mixture was stirred at RT for 1 h and then methyl iodide (87 µl, 1.39 mmol) was added. The reaction mixture was then warmed up to RT and stirring was continued overnight. The mixture was quenched with water and extracted with ether. The organic phase was washed with water and brine, dried (MgSO$_4$), filtered and concentrated in vacuo to give a residue which was purified by flash column chromatography (1:1 ethyl acetate:cyclohexane) to give the desired compound (83 mg, 39%) as a light yellow solid. $^1$H NMR (CDCl$_3$, 300 MHz): 7.56 (dd, J=9.5, 8.0 Hz, 1H), 7.10 (dd, J=9.5, 4.0 Hz, 1H), 3.59 (s, 3H).

EXAMPLE S28-D

Preparation of 6-amino-3-chloro-2-fluoro-benzoic acid and 2-amino-3-chloro-6-fluoro-benzoic acid A solution of 1 g (6.45 mmol) of 2-amino-6-fluoro-benzoic acid and 0.95 g (7.09 mmol) of N-chlorosuccinimide in 10 ml acetic acid was stirred at RT for 17 hours. The resulting suspension was then concentrated in vacuo, suspended in water and the pH was adjusted to 3 using a saturated NaHCO$_3$ aqueous solution. The suspension was extracted twice with ethyl acetate, and the combined organic phases were washed with brine, dried over magnesium sulfate, filtered and concentrated in vacuo. The residue was purified by silicagel chromatography (eluent: ethyl acetate) leading to 0.95 g of a mixture of 6-amino-3-chloro-2-fluoro-benzoic acid and 2-amino-3-chloro-6-fluoro-benzoic acid. MS (ISP) 187.9 (M−H)⁻.

EXAMPLE S29-D

Preparation of 2-amino-3,5-dichloro-6-fluoro-benzoic acid

A solution of 1.2 g (6.33 mmol) of 2-amino-6-fluoro-benzoic acid and 1.9 g (14.23 mmol) of N-chlorosuccinimide in 10 ml acetic acid was stirred at RT for 17 hours. 0.55 g of 1,3-dichloro-5,5-dimethylhydantoin (1.9 mmol) were added. After two hours stirring the suspension was concentrated in vacuo, suspended in water, stirred for 30 min and filtered leading after drying under high vacuo to 0.8 g (54%) of 2-amino-3,5-dichloro-6-fluoro-benzoic acid as a light yellow powder. MS 225 (M).

EXAMPLE S30-D

Preparation of 6-chloro-1-cyclopropylmethyl-1H-benzo[d][1,3]oxazine-2,4-dione

The title compound was prepared in analogy to of 6-chloro-1-methyl-1H-benzo[d][1,3]-oxazine-2,4-dione described in example S1-D. $^{1H}$NMR (DMSO-$d_6$, 300 MHz): δ 0.42-0.54 (m, 4H), 1.17 (m, 1H), 3.96 (d, J=6.9 Hz, 2H), 7.63 (d, J=9.0 Hz, 1H), 7.88 (dd, J=9.0 and 2.5 Hz, 1H), 7.97 (d, J=2.5 Hz, 1H).

EXAMPLE S31-D

Preparation of 3-chloro-2-fluoro-6-methylamino-benzoic acid (S31-D1)

a) Preparation of (4-chloro-3-fluoro-phenyl)-methyl-amine

Formic acid (1.76 ml) was added to acetic acid anhydride (0.91 ml) at 0° C. The solution was stirred for 10 min at this temperature. The reaction was heated under nitrogen to 55° C. for 2 h. The reaction mixture was cooled to 0° C. 4-Chloro-3-fluoroaniline (1.07 g) dissolved in THF (2 ml) was added and the reaction was stirred over night at RT. The solvent was evaporated in vacuo. The residue was dissolved in THF (4 ml). The solution was cooled to 0° C. and borane tetrahydrofuran complex 1M in THF (16.2 ml) was added slowly. Strong gas evolution was observed. The reaction was heated to reflux for 3 h, then cooled to 0° C. and MeOH (4 ml) was added dropwise. The reaction was stirred for 1 h and 1M aq HCl solution (6 ml) was added. The reaction was stirred over night at RT. The solvent was removed in vacuo and the pH of the aqueous layer was adjusted to 9 with 2N aq NaOH solution. The reaction mixture was extracted twice with diethyl ether and the combined organic layers were dried over sodium sulfate, filtered and the solvent was removed in vacuo to yield (4-chloro-3-fluoro-phenyl)-methyl-amine (1150 mg, 98%) as a light brown oil. $^{1H}$NMR (DMSO-$d_6$, 300 MHz): δ 2.65 (d, J=5.1 Hz, 3H), 6.15 (d, J=5.1 Hz, 1H), 6.20 (dd, J=3.0 and J=8.4 Hz, 1H), 6.45 (dd, J=2.4 and 12.3 Hz, 1H), 7.18 (t, J=8.7 Hz, 1H).

b) Preparation of 3-chloro-2-fluoro-6-methylamino-benzoic acid n-Butyllithium solution (1.6 M in hexane, 4.95 mL, 8.0 mmol) was added at −78° C. to THF (10 ml) under nitrogen. A solution of (4-chloro-3-fluoro-phenyl)-methyl-amine (575 mg, 4.0 mmol) in THF (3 mL) was added dropwise keeping the temperature below −70° C. The solution was stirred for 5 min at −75° C. Potassium tert-butylate (889 mg, 8 mmol) dissolved in THF (2 ml) was added within 15 min. The reaction was stirred at −75° C. for 2 h and treated with a large excess of dry ice. Within 30 min the reaction was warmed to RT. Water was added and the reaction was extracted twice with diethyl ether. The aqueous layer was acidified to pH1 with 1N aq. HCl solution and extracted twice with diethyl ether. The combined organic layers were washed with sat. aq. NaCl solution, dried over sodium sulfate, filtered and the solvent was removed in vacuo to yield 3-chloro-2-fluoro-6-methylamino-benzoic acid (83 mg, 11%). Light brown solid, $^{1H}$NMR (DMSO-$d_6$, 300 MHz): δ 81 (s, 3H), 6.52 (d, J=9.2 Hz, 1H), 7.45 (t, J=9.1 Hz, 1H).

| Ex. | Name | * | MS (ISP) |
|---|---|---|---|
| S31-D2 | 5-Chloro-2-ethylamino-nicotinic acid | S6-D | 199.0 (M − H)⁻ |
| S31-D3 | 5-Chloro-2-cyclopropylamino-nicotinic acid | S6-D | 211.0 (M − H)⁻ |
| S31-D4 | 5-Bromo-2-methylamino-nicotinic acid | S6-D | 228.9 (M − H)⁻ |
| S31-D5 | 5-Bromo-2-ethylamino-nicotinic acid | S6-D | 243.1 (M − H)⁻ |
| S31-D6 | 5-Fluoro-2-methylamino-nicotinic acid | S6-D | 169.1 (M − H)⁻ |
| S31-D7 | 2-Ethylamino-5-fluoro-nicotinic acid | S6-D | 183.1 (M − H)⁻ |
| S31-D8 | 5-Methyl-2-methylamino-nicotinic acid | S6-D | 167.2 (M + H)⁺ |
| S31-D9 | 2-Ethylamino-5-methyl-nicotinic acid | S6-D | 181.1 (M + H)⁺ |
| S31-D10 | 6-Chloro-3-ethylamino-pyridine-2-carboxylic acid | S7-D | 199.1 (M − H)⁻ |
| S31-D11 | 6-Chloro-3-cyclopropylamino-pyridine-2-carboxylic acid | S7-D | 211.0 (M − H)⁻ |
| S31-D12 | Potassium; 4-methylamino-thiophene-3-carboxylate | S19-D | 156.0 (M − H)⁻ |
| S31-D13 | Potassium; 2-methylamino-thiophene-3-carboxylate | S19-D | 156.0 (M − H)⁻ |
| S31-D14 | 3-Methyl-5-methylamino-isothiazole-4-carboxylic acid ethyl ester | S21-D | 201.2 (M + H)⁺ |
| S31-D15 | 5-Ethylamino-3-methyl-isothiazole-4-carboxylic acid ethyl ester | S21-D | 215.2 (M + H)⁺⁻⁽?⁾ |

-continued

| Ex. | Name | * | MS (ISP) |
|---|---|---|---|
| S31-D16 | 5-Isopropylamino-3-methyl-isothiazole-4-carboxylic acid ethyl ester | S21-D | 229.3 (M + H)+ |

*: Prepared in analogy to example

Amides: (Compound of Formula VI)

EXAMPLE S1-E

Preparation of N-(4-tert-butyl-benzyl)-2,5-dichloro-N-[2-(3,4-dichloro-phenyl)-ethyl]-nicotinamide (S1-E1)

A solution of 2,5-dichloronicotinic acid (300 mg, 1.56 mmol), (4-tert-butyl-benzyl)-[2-(3,4-dichloro-phenyl)-ethyl]-amine (578 mg, 1.72 mmol), 4-methylmorpholine (474 mg, 7.81 mmol), and HBTU (889 mg, 2.34 mmol) in DMF (9 mL) was stirred at RT for 16 h, then partitioned between heptane, ethyl acetate and water. The organic layer was washed with brine, dried (MgSO$_4$), and evaporated. Chromatography (SiO$_2$, heptane-ethyl acetate gradient) afforded the title compound (761 mg, 95%). White foam, MS (ISP) 509.0 (M+H)+.

| Ex. | Name | * | MS (ISP) |
|---|---|---|---|
| S1-E2 | N-(4-tert-Butyl-benzyl)-N-[2-(3,4-dichloro-phenyl)-ethyl]-2-fluoro-nicotinamide | S1-E | 459.3 (M + H)+ |
| S1-E3 | N-(4-tert-Butyl-benzyl)-4-chloro-N-[2-(3,4-dichloro-phenyl)-ethyl]-nicotinamide | S1-E | 475.2 (M + H)+ |
| S1-E4 | N-(4-tert-Butyl-benzyl)-4-chloro-N-[2-(3-trifluoromethyl-phenyl)-ethyl]-nicotinamide | S1-E | 475.3 (M + H)+ |
| S1-E5 | 5-Bromo-N-(4-tert-butyl-benzyl)-2-chloro-N-[2-(3,4-dichloro-phenyl)-ethyl]-nicotinamide | S1-E | 553.0 (M + H)+ |
| S1-E6 | N-(4-tert-Butyl-benzyl)-2-chloro-N-[2-(3,4-dichloro-phenyl)-ethyl]-5-fluoro-nicotinamide | S1-E | 493.3 (M + H)+ |

*: Prepared in analogy to example

Final Compounds: (Compounds of Formula I)

EXAMPLE 1

Preparation of 5-chloro-N-(4-cyclopentyl-benzyl)-2-isopropylamino-N-[2-(3-trifluoromethyl-phenyl)-ethyl]-benzamide To a solution of 50 mg of 5-chloro-2-isopropylamino-benzoic acid (0.23 mmol) and 81 mg (0.23 mmol) of (4-cyclopentyl-benzyl)-[2-(3-trifluoromethyl-phenyl)-ethyl]-amine in 4 ml of DMF were added 75 mg of TBTU (0.23 mmol) and 0.2 ml (1.17 mmol) of N,N-di-isopropylethyl amine. After stirring the reaction mixture over night at RT it was diluted with 50 ml water and extracted with ethyl acetate. The combined organic phases were washed with 10%-aqueous KHCO$_3$ solution, 0.1M HCl solution and brine, dried with magnesium sulfate, filtered and concentrated in vacuo. The remaining oil was purified by column chromatography (silica gel; heptane 100% to heptane/EtOAc 4:1) to give 90 mg (71%) of a colorless oil. MS (ISP) 543.5 (M+H)+.

EXAMPLE 2

Preparation of N-(4-tert-butyl-benzyl)-N-2-(3,4-dichloro-phenyl)-ethyl-2-methylamino-nicotinamide A mixture of N-(4-tert-butyl-benzyl)-N-[2-(3,4-dichloro-phenyl)-ethyl]-2-fluoro-nicotinamide (100 mg, 0.22 mmol), 41% aq. methylamine solution (1 mL) and THF (1 mL) was heated under microwave irradiation for 1 h at 100° C., then partitioned between ethyl acetate and water. The organic layer was washed with brine, dried (MgSO$_4$), and evaporated to produce the title compound (102 mg, 95%). Colourless gum, MS (ISP) 470.4 (M+H)+.

EXAMPLE 3

Preparation of 6-methyl-3-methylamino-pyridine-2-carboxylic acid [2-(4-chloro-phenyl)-ethyl]-(4-cyclobutyl-benzyl)-amide A mixture of 3-amino-6-methyl-pyridine-2-carboxylic acid [2-(4-chloro-phenyl)-ethyl]-(4-cyclobutyl-benzyl)-amide (151 mg, 0.348 mmol), 37% aq. formaldehyde solution (0.16 mL, 2.09 mmol) and ethanol (2 mL) was stirred at 50° C. for 3 h, then after removal of volatile material by distillation, sodium borohydride (55 mg, 1.39 mmol) was added, and stirring at 50° C. was continued over 3 h. After cooling, the reaction mixture was partitioned between ethyl acetate and water, the organic layer was washed with brine, dried (MgSO$_4$), and evaporated. Chromatography (SiO$_2$, heptane-ethyl acetate gradient) produced the title compound (126 mg, 81%). Colourless gum, MS (ISP) 448.3 (M+H)+.

EXAMPLE 4

Preparation of N-(4-tert-butyl-benzyl)-N-[2-(3,4-dichloro-phenyl)-ethyl]-5-ethyl-2-methylamino-nicotinamide A mixture of 5-ethyl-2-methylamino-nicotinic acid ethyl ester (40 mg, 0.19 mmol), 2 M aq. potassium hydroxide solution (0.19 mL, 0.38 mmol) and THF was heated at 60° C. for 16 h, then evaporated to dryness. The residue was taken up in DMF (3.2 mL) and treated with (4-tert-butyl-benzyl)-[2-(3,4-dichloro-phenyl)-ethyl]-amine (71 mg, 0.21 mmol), HBTU (109 mg, 0.29 mmol), and 4-methylmorpholine (58 mg, 0.57 mmol). The homogeneous solution was stirred at RT for 16 h, then partitioned between water and ethyl acetate. The organic layer was washed with brine, dried (MgSO$_4$), and evaporated. Chromatography (SiO$_2$, heptane-ethyl acetate gradient) produced the title compound (77 mg, 80%). Light yellow oil, MS (ISP) 498.4 (M+H)+.

EXAMPLE 5

N-(4-tert-butylbenzyl)-2-chloro-N-[2-(3,4-dichlorophenyl)-ethyl]-3-fluoro-6-methylaminobenzamide A mixture of 5-chloro-6-fluoro-1-methyl-1H-benzo[d][1,3]oxazine-2,4-dione (83 mg, 0.36 mmol) and (4-tert-butyl-benzyl)-[2-(3,4-dichloro-phenyl)-ethyl]-amine (122 mg, 0.36 mmol) in DMF (2 ml) was heated to 140° C. for 2 h and then at 110° C. overnight. The reaction mixture was then cooled to RT and the mixture was diluted with ethyl acetate and washed with water and brine. The organic layer was dried (MgSO$_4$), filtered and concentrated in vacuo to give a residue which was purified by flash column chromatography to give the desired product (51 mg, 27%) as a white solid. MS (ISP) 521.9 (M+H)+.

EXAMPLE 6

2-Acetylamino-N-(4-tert-butyl-benzyl)-5-chloro-N-[2-(3-trifluoromethyl-phenyl)-ethyl]-benzamide 2-Amino-N-(4-tert-butyl-benzyl)-5-chloro-N-[2-(3-trifluoromethyl-phenyl)-ethyl]-benzamide (140 mg, 0.286 mmol) was dissolved in methylene chloride (2 ml). Acetic acid anhydride (32 mg, 0.315 mmol) and ethyl-diisopropylamine (41 mg, 0.315 mmol) were added and the reaction was stirred over night at RT. Further acetic acid anhydride (30 µl) was added and the reaction was stirred for another night at RT. The reaction was extracted with ethyl acetate, the combined organic layers were concentrated in vacuo and the residue was purified by flash column chromatography (heptane/ethyl acetate:7/3) to yield the desired product (110 mg, 72%) as an off-white solid. MS (ISP) 529.2 (M−H)−.

EXAMPLE 7

5-Chloro-N-(4-cyclopropyl-benzyl)-2-methylamino-N-[2-(3-trifluoromethoxy-phenyl)-ethyl]-benzamide To a solution of 53 mg of 2-amino-5-chloro-benzoic acid (0.33 mmol) and 105 mg (0.33 mmol) of (4-cyclopropyl-benzyl)-[2-(3-trifluoromethyl-phenyl)-ethyl]-amine in 4.5 ml of DMF were added 171 mg of HBTU (0.45 mmol) and 0.1 ml (0.9 mmol) of 4-methyl-morpholine. After stirring the reaction mixture over night at RT it was diluted with 50 ml water and extracted with ethyl acetate. The combined organic phases were washed with 10% aqueous KHCO$_3$ solution, 0.1M HCl solution and brine, dried with magnesium sulfate, filtered and concentrated in vacuo. The remaining oil was purified by column chromatography (silica gel; heptane/EtOAc 6:1) to give 127 mg (88%) of 2-amino-5-chloro-N-(4-cyclopropyl-benzyl)-N-[2-(3-trifluoromethyl-phenyl)-ethyl]-benzamide as a yellow oil. MS (ISP) 473 (M+H)+.

The complete amount (127 mg, 0.27 mmol) was dissolved in 2.5 ml DCM under argon and cooled down to −10° C. Then 0.057 ml of trifluoroacetic acid anhydride (0.4 mmol) and 0.065 ml pyridine (0.8 mmol) were added and the reaction mixture was stirred for 2 h at RT. The reaction mixture was poured on 1.5 ml 1 N aqueous HCl and the organic phase was separated and washed with brine. The aqueous phases were reextracted with DCM, and the combined organic phases were dried over magnesium sulfate, filtered and concentrated in vacuo to give 151 mg (98%) of 5-chloro-N-(4-cyclopropyl-benzyl)-2-(2,2,2-trifluoro-acetylamino)-N-[2-(3-trifluoromethyl-phenyl)-ethyl]-benzamide as a light yellow solid. MS (ISP) 569.2 (M+H)+.

50 mg of 5-chloro-N-(4-cyclopropyl-benzyl)-2-(2,2,2-trifluoro-acetylamino)-N-[2-(3-trifluoromethyl-phenyl)-ethyl]-benzamide (0.09 mmol) were dissolved in 1 ml DMF and 0.1 ml DMPU (1,3-dimethyl-3,4,5,6-tetrahydro-2-pyridinon) under argon and cooled down to 0° C. 6 mg of sodium hydride (55% dispersion in oil, 0.135 mmol) were then added and after 15 min stirring at RT the reaction mixture was again cooled down to 0° C. 0.008 ml of methyl iodide (0.135 mmol) were added and after 4 h stirring at RT a second portion of the same amount was added. After 20 hours stirring at RT the reaction mixture was diluted with ethyl acetate and washed with water and brine. The aqueous phases were reextracted with ethyl acetate, and the combined organic phases were dried over magnesium sulfate, filtered off and concentrated in vacuo. The residue was purified by column chromatography (silica gel; heptane/EtOAc 9:1) to give 36 mg (70%) 5-chloro-N-(4-cyclopropyl-benzyl)-2-[methyl-(2,2,2-trifluoro-acetyl)-amino]-N-[2-(3-trifluoromethyl-phenyl)-ethyl]-benzamide as a colorless viscous oil. MS (ISP) 583.2 (M+H)+.

35 mg of 5-chloro-N-(4-cyclopropyl-benzyl)-2-[methyl-(2,2,2-trifluoro-acetyl)-amino]-N-[2-(3-trifluoromethyl-phenyl)-ethyl]-benzamide were dissolved in 1 ml methanol and 0.06 ml 1N aqueous NaOH and heated to 55° C. for 5 hours. The mixture was then concentrated in vacuo, diluted with ethyl acetate and washed with water and brine. The organic phase was dried over magnesium sulfate, filtered off and concentrated in vacuo, to give 28 mg (96%) 5-chloro-N-(4-cyclopropyl-benzyl)-2-methylamino-N-[2-(3-trifluoromethyl-phenyl)-ethyl]-benzamide as a light yellow viscous oil. (ISP) 503.1 (M+H)+.

EXAMPLE 8

(2-{(4-tert-Butyl-benzyl)-[2-(3-trifluoromethoxy-phenyl)-ethyl]-carbamoyl}-4-chloro-phenylamino)-acetic acid A solution of 33 mg of (2-{(4-tert-Butyl-benzyl)-[2-(3-trifluoromethoxy-phenyl)-ethyl]-carbamoyl}-4-chloro-phenylamino)-acetic acid ethyl ester (0.06 mmol) in 0.5 ml methanol and 0.11 ml 1N aqueous NaOH was heated for 2 hours to 50° C. After cooling down to RT the mixture was neutralized with 0.11 ml 1N aqueous HCl, treated with a small amount of water, and extracted twice with ethylacetate.

The combined organic phases were washed with brine, dried over magnesium sulfate, filtered and concentrated in vacuo to give 26 mg (79%) of the title compound as an off-white solid. MS (ISP) 563.4 (M+H)+.

EXAMPLE 9

5-Chloro-2-methylamino-N-[4-(3,3,3-trifluoro-2-hydroxy-propoxy)-benzyl]-N-[2-(3-trifluoromethyl-phenyl)-ethyl]-benzamide A solution of 930 mg (1.68 mmol) of N-(4-benzyloxy-benzyl)-5-chloro-2-methylamino-N-[2-(3-trifluoromethyl-phenyl)-ethyl]-benzamide (2 mmol) in 30 ml ethylacetate was hydrogenated over 300 mg of 5% Pd—C for 4 hours at RT. After completion of the reaction, the suspension was filtered, the catalyst washed with additional ethyl acetate and the filtrate was concentrated in vacuo. The residue was purified by column chromatography (silica gel; heptane/-EtOAc 3:1) to give 339 mg 5-chloro-N-(4-hydroxy-benzyl)-2-methylamino-N-[2-(3-trifluoromethyl-phenyl)-ethyl]-benzamide (75%) as a white foam. MS (ISP) 463 (M+H)+.

A suspension of 80 mg (0.17 mmol) of 5-chloro-N-(4-hydroxy-benzyl)-2-methylamino-N-[2-(3-trifluoromethyl-phenyl)-ethyl]-benzamide, 40 mg (0.21 mmol) 3-bromo-1,1,1-trifluoro-2-propanol and 57 mg (0.41 mmol) of potassium carbonate in 3 ml DMF was stirred at RT for 65 hours. The reaction mixture was then diluted with 15 ml water and 15 ml brine, and extracted twice with ethylacetate. The combined organic layers were washed with brine, dried over magnesium sulfate, filtered and concentrated in vacuo. The residue was purified by column chromatography (silica gel; DCM/EtOAc 97:3) to give 58 mg of 5-chloro-2-methylamino-N-[4-(3,3,3-trifluoro-2-hydroxy-propoxy)-benzyl]-N-[2-(3-trifluoromethyl-phenyl)-ethyl]-benzamide (55%) as a light yellow viscous oil. MS (ISP) 575.3 (M+H)+.

EXAMPLE 10

N-(4-tert-Butyl-benzyl)-5-chloro-2-(3-hydroxy-propylamino)-N-[2-(3-trifluoromethyl-phenyl)-ethyl]-benzamide and 3-(2-{(4-tert-butyl-benzyl)-[2-(3-trifluoromethyl-phenyl)-ethyl]-carbamoyl}-4-chloro-phenylamino)-propionic acid A solution of 150 mg (0.31 mmol) of 2-amino-N-(4-tert-butyl-benzyl)-5-chloro-N-[2-(3-trifluoromethyl-phenyl)-ethyl]-benzamide and 76 mg (0.46 mmol) of formylpropionic acid ethylester (prepared by stirring 3,3-diethoxypropionic acid ethylester at RT with 1N—HCl followed by extraction with diethylether and concentration in vacuo) in 3 ml EtOH was refluxed for two hours. The reaction mixture was cooled down to RT and reacted with 17 mg (0.46 mmol) of sodium borohydride. After 5 min at RT and 30 min under reflux additional 9 mg (0.29 mmol) of sodium borohydride were added followed by 5 min at RT and 30 min under reflux. The reaction mixture was then concentrated, treated with diethylether and 2 drops 1N—HCl, and extracted twice with ethylacetate. The combined organic layers were washed with brine, dried over magnesium sulfate, filtered and concentrated in vacuo. The residue was purified by column chromatography (silica gel; heptane/EtOAc 90:10 to 50:50) to give 53 mg (28%) of 3-(2-{(4-tert-butyl-benzyl)-[2-(3-trifluoromethyl-phenyl)-ethyl]-carbamoyl}-4-chloro-phenylamino)-propionic acid ethyl ester as a light yellow viscous oil [MS (ISP) 489.4 (M+H)+] and 12 mg (7%) of N-(4-tert-butyl-benzyl)-5-chloro-2-(3-hydroxy-propylamino)-N-[2-(3-trifluoromethyl-phenyl)-ethyl]-benzamide as light yellow amorphous solid [MS (ISP) 547.4 (M+H)+]. A solution of 42 mg (0.07 mmol) of 3-(2-{(4-tert-butyl-benzyl)-[2-(3-trifluoromethyl-phenyl)-ethyl]-carbamoyl}-4-chloro-phenylamino)-propionic acid ethyl ester in 1 ml EtOH and 0.14 ml 1N-NaOH was stirred at 50° C. for 17 hours. The reaction mixture was concentrated in vacuo, treated with water and the pH was adjusted to 3 with 1N—HCl. The mixture was extracted twice with diethylether, washed with brine, dried over magnesium sulfate, filtered and concentrated in vacuo to give 39 mg (93%) of 3-(2-{(4-tert-butyl-benzyl)-[2-(3-trifluoromethyl-phenyl)-ethyl]-carbamoyl}-4-chloro-phenylamino)-propionic acid as an off-white foam. MS (ISP) 561.5 (M+H)+.

EXAMPLE 11

2-Amino-3-bromo-N-(4-tert-butyl-benzyl)-5-methyl-N-[2-(3-trifluoromethyl-phenyl)-ethyl]-benzamide 2-Amino-N-(4-tert-butyl-benzyl)-5-methyl-N-[2-(3-trifluoromethyl-phenyl)-ethyl]-benzamide (60 mg, 0.128 mmol) was dissolved in acetonitrile (2 ml) and N-bromosuccinimide (23 mg, 0.128 mmol) was added. The reaction was heated to 75° C. for 4 h. The reaction mixture was cooled to RT and partitionated between water and methylene chloride. The aqueous layer was extracted with methylene chloride and the combined organic phase was dried (MgSO$_4$), filtered and concentrated in vacuo to give the desired product (50 mg, 71%) as a light brown oil. MS (ISP) 547.3 (M+H)+.

EXAMPLE 12

2-Amino-N-(4-tert-butyl-benzyl)-3-chloro-5-methyl-N-[2-(3-trifluoromethyl-phenyl)-ethyl]-benzamide 2-Amino-N-(4-tert-butyl-benzyl)-5-methyl-N-[2-(3-trifluoromethyl-phenyl)-ethyl]-benzamide (60 mg, 0.128 mmol) was dissolved in acetonitrile (2 ml) and N-chlorosuccinimide (23 mg, 0.128 mmol) was added. The reaction was heated to 95° C. for 4 h. The reaction mixture was cooled to RT and partitionated between water and methylene chloride. The aqueous layer was extracted with methylene chloride and the combined organic phase was dried (MgSO$_4$), filtered and concentrated in vacuo to give a residue which was purified by flash column chromatography (heptane/ethyl acetate 7:3) to yield the desired product (18 mg, 28%) as a brown gum. MS (ISP) 503.3 (M+H)+.

EXAMPLE 13

N-(4-tert-Butyl-benzyl)-5-chloro-2-(cyanomethyl-amino)-N-[2-(3-trifluoromethyl-phenyl)-ethyl]-benzamide (13.1)

2-Amino-N-(4-tert-butyl-benzyl)-5-chloro-N-[2-(3-trifluoromethyl-phenyl)-ethyl]-benzamide (80 mg, 0.164 mmol), bromo-acetonitrile (21 mg, 0.172 mmol) and sodium hydrogen catbonat (17 mg, 01.96 mmol) were suspended in ethanol (21 ml) and heated to 100° C. for 3 days. The reaction mixture was cooled to RT, filtered and the precipitate was washed with ethanol. The solvent of the filtrate was concentrated in vacuo to give a residue which was purified by flash column chromatography (heptane/ethyl acetate 7:3) to yield the desired product (26 mg, 30%) as a yellow solid. MS (ISP) 526.2 (M−H)−.

| Ex. | Name | * | MS (ISP) |
|---|---|---|---|
| 13.2 | 6-Chloro-3-methylamino-pyridine-2-carboxylic acid (4-tert-butyl-benzyl)-[2-(2-chloro-pyridin-4-yl)-ethyl]-amide | 1 | 471.2 (M + H)+ |
| 13.3 | N-(4-tert-Butyl-benzyl)-5-chloro-N-[2-(2-chloro-pyridin-4-yl)-ethyl]-2-methylamino-nicotinamide | 1 | 471.2 (M + H)+ |
| 13.4 | N-(4-tert-Butyl-benzyl)-5-chloro-N-[2-(2-chloro-pyridin-4-yl)-ethyl]-2-methylamino-benzamide | 1 | 470.4 (M + H)+ |
| 13.5 | 5-Chloro-N-[2-(4-fluoro-phenyl)-ethyl]-2-isopropyl-amino-N-(4-pentafluoroethyl-benzyl)-benzamide | 1 | 543.2 (M + H)+ |
| 13.6 | 5-Chloro-2-isopropylamino-N-[4-(1,2,2,2-tetrafluoro-1-trifluoromethyl-ethyl)-benzyl]-N-[2-(3-trifluoromethyl-phenyl)-ethyl]-benzamide | 1 | 643.0 (M + H)+ |
| 13.7 | 5-Chloro-N-[2-(4-fluoro-phenyl)-ethyl]-2-isopropyl-amino-N-[4-(1,2,2,2-tetrafluoro-1-trifluoromethyl-ethyl)-benzyl]-benzamide | 1 | 593.3 (M + H)+ |
| 13.8 | 5-Chloro-N-[2-(3,4-dichloro-phenyl)-ethyl]-2-isopropylamino-N-[4-(1,2,2,2-tetrafluoro-1-trifluoromethyl-ethyl)-benzyl]-benzamide | 1 | 643.2 (M + H)+ |
| 13.9 | 5-Chloro-2-isopropylamino-N-(4-pentafluoroethyl-benzyl)-N-[2-(3-trifluoromethoxy-phenyl)-ethyl]-benzamide | 1 | 609.3 (M + H)+ |
| 13.10 | N-(4-tert-Butyl-benzyl)-5-chloro-2-methylamino-N-[2-(4-trifluoromethyl-pyridin-2-yl)-ethyl]-nicotinamide | 1 | 505.3 (M + H)+ |
| 13.11 | N-(4-tert-Butyl-benzyl)-5-chloro-2-methylamino-N-[2-(4-trifluoromethyl-pyridin-2-yl)-ethyl]-benzamide | 1 | 504.3 (M + H)+ |
| 13.12 | 6-Chloro-3-methylamino-pyridine-2-carboxylic acid (4-tert-butyl-benzyl)-[2-(5-trifluoromethyl-pyridin-2-yl)-ethyl]-amide | 1 | 505.1 (M + H)+ |
| 13.13 | N-(4-tert-Butyl-benzyl)-5-chloro-2-methylamino-N-[2-(5-trifluoromethyl-pyridin-2-yl)-ethyl]-benzamide | 1 | 504.1 (M + H)+ |
| 13.14 | 6-Chloro-3-methylamino-pyridine-2-carboxylic acid (4-tert-butyl-benzyl)-[2-(6-trifluoromethyl-pyridin-2-yl)-ethyl]-amide | 1 | 505.3 (M + H)+ |
| 13.15 | N-(4-tert-Butyl-benzyl)-5-chloro-2-methylamino-N-[2-(6-trifluoromethyl-pyridin-2-yl)-ethyl]-nicotinamide | 1 | 505.4 (M + H)+ |
| 13.16 | N-(4-tert-Butyl-benzyl)-5-chloro-2-methylamino-N-[2-(6-trifluoromethyl-pyridin-2-yl)-ethyl]-benzamide | 1 | 504.3 (M + H)+ |
| 13.17 | 5-Chloro-N-(4-cyclobutyl-benzyl)-N-[2-(3,4-dichloro-phenyl)-ethyl]-2-isopropylamino-benzamide | 1 | 529.3 (M + H)+ |
| 13.18 | 5-Chloro-N-(4-cyclobutyl-benzyl)-2-isopropylamino-N-[2-(3-trifluoromethyl-phenyl)-ethyl]-benzamide | 1 | 529.4 (M + H)+ |
| 13.19 | N-(4-tert-Butyl-benzyl)-5-chloro-N-[2-(5-chloro-pyridin-2-yl)-ethyl]-2-methylamino-benzamide | 1 | 470.4 (M + H)+ |
| 13.20 | 5-Chloro-N-[4-(1-fluoro-cyclobutyl)-benzyl]-2-methyl-amino-N-[2-(3-trifluoromethyl-phenyl)-ethyl]-benzamide | 1 | 519.4 (M + H)+ |
| 13.21 | 5-Chloro-N-[2-(3,4-dichloro-phenyl)-ethyl]-N-[4-(1-fluoro-cyclobutyl)-benzyl]-2-methylamino-benzamide | 1 | 519.2 (M + H)+ |
| 13.22 | 5-Chloro-N-[2-(3,4-dichloro-phenyl)-ethyl]-N-[4-(1-methoxy-cyclobutyl)-benzyl]-2-methylamino-nicotinamide | 1 | 532.1 (M + H)+ |
| 13.23 | N-(4-tert-Butyl-benzyl)-5-chloro-2-cyclopropylamino-N-[2-(3,4-dichloro-phenyl)-ethyl]-benzamide | 1 | 529.3 (M + H)+ |
| 13.24 | N-(4-tert-Butyl-benzyl)-5-chloro-2-cyclopropylamino-N-[2-(3-trifluoromethyl-phenyl)-ethyl]-benzamide | 1 | 529.3 (M + H)+ |
| 13.25 | N-(4-Cyclobutyl-benzyl)-2-cyclopropylamino-5-trifluoromethyl-N-[2-(3-trifluoromethyl-phenyl)-ethyl]-benzamide | 1 | 561.3 (M + H)+ |
| 13.26 | 5-Chloro-N-(4-cyclobutyl-benzyl)-N-[2-(3,4-dichloro-phenyl)-ethyl]-2-ethylamino-benzamide | 1 | 515.3 (M + H)+ |
| 13.27 | 5-Chloro-N-(4-cyclobutyl-benzyl)-2-ethylamino-N-[2-(3-trifluoromethyl-phenyl)-ethyl]-benzamide | 1 | 515.1 (M + H)+ |
| 13.28 | 5-Chloro-N-(4-cyclopentyl-benzyl)-2-ethylamino-N-[2-(3-trifluoromethyl-phenyl)-ethyl]-benzamide | 1 | 529.3 (M + H)+ |
| 13.29 | 5-Chloro-N-(4-cyclobutyl-benzyl)-2-ethylamino-N-[2-(4-fluoro-3-trifluoromethyl-phenyl)-ethyl]-benzamide | 1 | 533.2 (M + H)+ |
| 13.30 | 5-Chloro-N-(4-cyclopentyl-benzyl)-N-[2-(3,4-dichloro-phenyl)-ethyl]-2-ethylamino-benzamide | 1 | 529.3 (M + H)+ |
| 13.31 | 5-Chloro-N-(4-cyclopentyl-benzyl)-2-ethylamino-N-[2-(4-fluoro-3-trifluoromethyl-phenyl)-ethyl]-benzamide | 1 | 547.3 (M + H)+ |
| 13.32 | N-(4-tert-Butyl-benzyl)-5-chloro-N-[2-(4-chloro-3-trifluoromethyl-pyrazol-1-yl)-ethyl]-2-methylamino-benzamide | 1 | 527.2 (M + H)+ |
| 13.33 | N-(4-tert-Butyl-benzyl)-5-chloro-2-methylamino-N-[2-(3-phenyl-pyrazol-1-yl)-ethyl]-benzamide | 1 | 501.2 (M + H)+ |
| 13.34 | N-(4-tert-Butyl-benzyl)-5-chloro-N-[2-(4-chloro-5-methyl-3-trifluoromethyl-pyrazol-1-yl)-ethyl]-2-methylamino-nicotinamide | 1 | 542.3 (M + H)+ |

-continued

| Ex. | Name | * | MS (ISP) |
|---|---|---|---|
| 13.35 | N-(4-tert-Butyl-benzyl)-5-chloro-N-[2-(4-chloro-3-methyl-5-trifluoromethyl-pyrazol-1-yl)-ethyl]-2-methylamino-benzamide | 1 | 541.5 (M + H)+ |
| 13.36 | N-(4-tert-Butyl-benzyl)-5-chloro-N-[2-(4-chloro-5-methyl-3-trifluoromethyl-pyrazol-1-yl)-ethyl]-2-methylamino-benzamide | 1 | 541.3 (M + H)+ |
| 13.37 | N-(4-tert-Butyl-benzyl)-5-chloro-2-methylamino-N-[2-(4-trifluoromethyl-imidazol-1-yl)-ethyl]-nicotinamide | 1 | 494.4 (M + H)+ |
| 13.38 | N-(4-tert-Butyl-benzyl)-5-chloro-2-methylamino-N-[2-(4-trifluoromethyl-imidazol-1-yl)-ethyl]-benzamide | 1 | 493.4 (M + H)+ |
| 13.39 | N-(4-tert-Butyl-benzyl)-5-chloro-2-methylamino-N-[2-(5-methyl-3-trifluoromethyl-pyrazol-1-yl)-ethyl]-benzamide | 1 | 507.4 (M + H)+ |
| 13.40 | N-(4-tert-Butyl-benzyl)-5-chloro-2-methylamino-N-[2-(3-trifluoromethyl-pyrazol-1-yl)-ethyl]-benzamide | 1 | 493.1 (M + H)+ |
| 13.41 | N-(4-tert-Butyl-benzyl)-5-chloro-2-methylamino-N-[2-(5-trifluoromethyl-pyrazol-1-yl)-ethyl]-benzamide | 1 | 493.4 (M + H)+ |
| 13.42 | 3-Ethylamino-5-methyl-isoxazole-4-carboxylic acid (4-tert-butyl-benzyl)-[2-(3,4-dichloro-phenyl)-ethyl]-amide | 1 | 488.1 (M + H)+ |
| 13.43 | 1,3-Dimethyl-5-methylamino-1H-pyrazole-4-carboxylic acid (4-tert-butyl-benzyl)-[2-(3,4-dichloro-phenyl)-ethyl]-amide | 1 | 487.3 (M + H)+ |
| 13.44 | 5-Ethylamino-3-methyl-isothiazole-4-carboxylic acid (4-tert-butyl-benzyl)-[2-(3,4-dichloro-phenyl)-ethyl]-amide | 4 | 504.0 (M + H)+ |
| 13.45 | 3-Methyl-5-methylamino-isothiazole-4-carboxylic acid (4-tert-butyl-benzyl)-[2-(3-trifluoromethyl-phenyl)-ethyl]-amide | 4 | 490.3 (M + H)+ |
| 13.46 | 3-Methyl-5-methylamino-isothiazole-4-caboxylic acid (4-tert-butyl-benzyl)-[2-(3,4-dichloro-phenyl)-ethyl]-amide | 4 | 490.3 (M + H)+ |
| 13.47 | 5-Cyclopropylamino-3-methyl-isothiazole-4-carboxylic acid (4-tert-butyl-benzyl)-[2-(3,4-dichloro-phenyl)-ethyl]-amide | 4 | 516.3 (M + H)+ |
| 13.48 | 5-Cyclopropylamino-3-methyl-isothiazole-4-carboxylic acid (4-tert-butyl-benzyl)-[2-(3-trifluoromethyl-phenyl)-ethyl]-amide | 4 | 516.3 (M + H)+ |
| 13.49 | 5-Isopropylamino-3-methyl-isothiazole-4-carboxylic acid (4-tert-butyl-benzyl)-[2-(3-trifluoromethyl-phenyl)-ethyl]-amide | 4 | 518.5 (M + H)+ |
| 13.50 | 5-Isopropylamino-3-methyl-isothiazole-4-carboxylic acid (4-tert-butyl-benzyl)-[2-(3,4-dichloro-phenyl)-ethyl]-amide | 4 | 518.2 (M + H)+ |
| 13.51 | 5-Cyclopropylamino-thiazole-4-carboxylic acid (4-tert-butyl-benzyl)-[2-(3-trifluoromethyl-phenyl)-ethyl]-amide | 1 | 502.3 (M + H)+ |
| 13.52 | 2-Methylamino-thiophene-3-carboxylic acid (4-tert-butyl-benzyl)-[2-(3-trifluoromethyl-phenyl)-ethyl]-amide | 1 | 475.2 (M + H)+ |
| 13.53 | 3-Methylamino-thiophene-2-carboxylic acid (4-tert-butyl-benzyl)-[2-(3-trifluoromethyl-phenyl)-ethyl]-amide | 1 | 475.2 (M + H)+ |
| 13.54 | 3-Methylamino-thiophene-2-carboxylic acid (4-tert-butyl-benzyl)-[2-(3,4-dichloro-phenyl)-ethyl]-amide | 1 | 475.2 (M + H)+ |
| 13.55 | 4-Methylamino-thiophene-3-carboxylic acid (4-tert-butyl-benzyl)-[2-(3-trifluoromethyl-phenyl)-ethyl]-amide | 1 | 475.1 (M + H)+ |
| 13.56 | 4-Methylamino-thiophene-3-carboxylic acid (4-tert-butyl-benzyl)-[2-(3,4-dichloro-phenyl)-ethyl]-amide | 1 | 475.0 (M + H)+ |
| 13.57 | 4-Acetylamino-N-(4-tert-butyl-benzyl)-N-[2-(3,4-dichloro-phenyl)-ethyl]-nicotinamide | 1 | 498.2 (M + H)+ |
| 13.58 | 4-Acetylamino-N-(4-tert-butyl-benzyl)-N-[2-(4-chloro-3-trifluoromethyl-phenyl)-ethyl]-nicotinamide | 1 | 532.1 (M + H)+ |
| 13.59 | 4-Acetylamino-N-(4-tert-butyl-benzyl)-N-[2-(3-trifluoromethyl-phenyl)-ethyl]-nicotinamide | 1 | 498.2 (M + H)+ |
| 13.60 | 3-Amino-pyridine-2-carboxylic acid (4-tert-butyl-benzyl)-[2-(3,4-dichloro-phenyl)-ethyl]-amide | 1 | 456.1 (M + H)+ |
| 13.61 | 3-Acetylamino-pyridine-2-carboxylic acid (4-tert-butyl-benzyl)-[2-(3,4-dichloro-phenyl)-ethyl]-amide | 1 | 498.4 (M + H)+ |
| 13.62 | 2-Amino-N-(4-tert-butyl-benzyl)-N-[2-(4-chloro-3-trifluoromethyl-phenyl)-ethyl]-nicotinamide | 1 | 490.3 (M + H)+ |
| 13.63 | 2-Amino-N-(4-tert-butyl-benzyl)-N-[2-(3-trifluoromethyl-phenyl)-ethyl]-nicotinamide | 1 | 456.5 (M + H)+ |
| 13.64 | 3-Methylamino-pyridine-2-carboxylic acid (4-tert-butyl-benzyl)-[2-(3,4-dichloro-phenyl)-ethyl]-amide | 3 | 470.1 (M + H)+ |
| 13.65 | 3-Amino-pyridine-2-carboxylic acid (4-tert-butyl-benzyl)-[2-(3-trifluoromethyl-phenyl)-ethyl]-amide | 1 | 456.5 (M + H)+ |

-continued

| Ex. | Name | * | MS (ISP) |
|---|---|---|---|
| 13.66 | 3-Methylamino-pyridine-2-carboxylic acid (4-tert-butyl-benzyl)-[2-(3-trifluoromethyl-phenyl)-ethyl]-amide | 3 | 470.5 (M + H)+ |
| 13.67 | 3-Amino-6-methyl-pyridine-2-carboxylic acid (4-tert-butyl-benzyl)-[2-(3,4-dichloro-phenyl)-ethyl]-amide | 1 | 470.4 (M + H)+ |
| 13.68 | 6-Methyl-3-methylamino-pyridine-2-carboxylic acid (4-tert-butyl-benzyl)-[2-(3,4-dichloro-phenyl)-ethyl]-amide | 3 | 484.5 (M + H)+ |
| 13.69 | N-(4-tert-Butyl-benzyl)-N-[2-(3,4-dichloro-phenyl)-ethyl-2-ethylamino-nicotinamide | 2 | 484.5 (M + H)+ |
| 13.70 | N-(4-tert-Butyl-benzyl)-N-[2-(3,4-dichloro-phenyl)-ethyl-2-dimethylamino-nicotinamide | 2 | 484.5 (M + H)+ |
| 13.71 | N-(4-tert-Butyl-benzyl)-N-[2-(3,4-dichloro-phenyl)-ethyl]-4-methylamino-nicotinamide | 2 | 470.1 (M + H)+ |
| 13.72 | N-(4-tert-Butyl-benzyl)-2-cyclopropylamino-N-[2-(3,4-dichloro-phenyl)-ethyl]-nicotinamide | 2 | 496.5 (M + H)+ |
| 13.73 | N-(4-tert-Butyl-benzyl)-N-[2-(3,4-dichloro-phenyl)-ethyl]-4-ethylamino-nicotinamide | 2 | 484.2 (M + H)+ |
| 13.74 | N-(4-tert-Butyl-benzyl)-5-chloro-N-[2-(3,4-dichloro-phenyl)-ethyl]-2-methylamino-nicotinamide | 2 | 504.3 (M + H)+ |
| 13.75 | 5-Bromo-N-(4-tert-butyl-benzyl)-N-[2-(3,4-dichloro-phenyl)-ethyl]-2-methylamino-nicotinamide | 2 | 548.2 (M + H)+ |
| 13.76 | 5-Bromo-N-(4-tert-butyl-benzyl)-N-[2-(3,4-dichloro-phenyl)-ethyl]-2-ethylamino-nicotinamide | 2 | 562.3 (M + H)+ |
| 13.77 | N-(4-tert-Butyl-benzyl)-N-[2-(3,4-dichloro-phenyl)-ethyl]-2-(2-hydroxy-ethylamino)-nicotinamide | 2 | 500.3 (M + H)+ |
| 13.78 | N-(4-tert-Butyl-benzyl)-5-chloro-N-[2-(3,4-dichloro-phenyl)-ethyl]-2-ethylamino-nicotinamide | 2 | 518.3 (M + H)+ |
| 13.79 | N-(4-tert-Butyl-benzyl)-5-chloro-2-cyclopropylamino-N-[2-(3,4-dichloro-phenyl)-ethyl]-nicotinamide | 2 | 530.3 (M + H)+ |
| 13.80 | N-(4-tert-Butyl-benzyl)-N-[2-(3,4-dichloro-phenyl)-ethyl]-5-fluoro-2-methylamino-nicotinamide | 2 | 488.1 (M + H)+ |
| 13.81 | N-(4-tert-Butyl-benzyl)-5-chloro-N-[2-(3,4-dichloro-phenyl)-ethyl]-2-(2-hydroxy-ethylamino)-nicotinamide | 2 | 534.3 (M + H)+ |
| 13.82 | 3-Amino-N-(4-tert-butyl-benzyl)-N-[2-(3,4-dichloro-phenyl)-ethyl]-isonicotinamide | 1 | 456.4 (M + H)+ |
| 13.83 | 3-Amino-pyrazine-2-carboxylic acid (4-tert-butyl-benzyl)-[2-(3,4-dichloro-phenyl)-ethyl]-amide | 1 | 457.4 (M + H)+ |
| 13.84 | N-(4-tert-Butyl-benzyl)-N-[2-(3,4-dichloro-phenyl)-ethyl]-2-((R)-2-hydroxymethyl-pyrrolidin-1-yl)-nicotinamide | 2 | 540.4 (M + H)+ |
| 13.85 | N-(4-tert-Butyl-benzyl)-N-[2-(3,4-dichloro-phenyl)-ethyl]-2-pyrrolidin-1-yl-nicotinamide | 2 | 510.5 (M + H)+ |
| 13.86 | N-(4-tert-Butyl-benzyl)-N-[2-(3,4-dichloro-phenyl)-ethyl]-3-methylamino-isonicotinamide | 3 | 470.4 (M + H)+ |
| 13.87 | 3-Methylamino-pyrazine-2-carboxylic acid (4-tert-butyl-benzyl)-[2-(3,4-dichloro-phenyl)-ethyl]-amide | 3 | 471.2 (M + H)+ |
| 13.88 | N-(4-tert-Butyl-benzyl)-N-[2-(3,4-dichloro-phenyl)-ethyl]-2-ethylamino-5-fluoro-nicotinamide | 2 | 502.2 (M + H)+ |
| 13.89 | N-(4-tert-Butyl-benzyl)-2-cyclopropylamino-N-[2-(3,4-dichloro-phenyl)-ethyl]-5-fluoro-nicotinamide | 2 | 514.4 (M + H)+ |
| 13.90 | 2-Azetidin-1-yl-N-(4-tert-butyl-benzyl)-N-[2-(3,4-dichloro-phenyl)-ethyl]-nicotinamide | 2 | 496.4 (M + H)+ |
| 13.91 | 4-Amino-pyrimidine-5-carboxylic acid (4-tert-butyl-benzyl)-[2-(3,4-dichloro-phenyl)-ethyl]-amide | 1 | 457.4 (M + H)+ |
| 13.92 | 2-Amino-N-(4-tert-butyl-benzyl)-N-[2-(3,4-dichloro-phenyl)-ethyl]-6-methyl-nicotinamide | 1 | 470.4 (M + H)+ |
| 13.93 | 4-Methylamino-pyrimidine-5-carboxylic acid (4-tert-butyl-benzyl)-[2-(3,4-dichloro-phenyl)-ethyl]-amide | 3 | 471.2 (M + H)+ |
| 13.94 | N-(4-tert-Butyl-benzyl)-N-[2-(3,4-dichloro-phenyl)-ethyl]-6-methyl-2-methylamino-nicotinamide | 3 | 484.5 (M + H)+ |
| 13.95 | 6-Chloro-3-methylamino-pyridine-2-carboxylic acid (4-tert-butyl-benzyl)-[2-(3,4-dichloro-phenyl)-ethyl]-amide | 1 | 504.3 (M + H)+ |
| 13.96 | 5-Chloro-N-[2-(3,4-dichloro-phenyl)-ethyl]-2-methylamino-N-[4-(1,2,2,2-tetrafluoro-1-trifluoromethyl-ethyl)-benzyl]-nicotinamide | 1 | 616.3 (M + H)+ |
| 13.97 | 5-Chloro-N-[2-(4-fluoro-phenyl)-ethyl]-2-methylamino-N-[4-(1,2,2,2-tetrafluoro-1-trifluoromethyl-ethyl)-benzyl]-nicotinamide | 1 | 566.3 (M + H)+ |
| 13.98 | 5-Chloro-2-methylamino-N-[4-(1,2,2,2-tetrafluoro-1-trifluoromethyl-ethyl)-benzyl]-N-[2-(3-trifluoromethyl-phenyl)-ethyl]-nicotinamide | 1 | 616.3 (M + H)+ |
| 13.99 | N-(4-tert-Butyl-benzyl)-5-chloro-2-methylamino-N-[2-(3-trifluoromethyl-phenyl)-ethyl]-nicotinamide | 1 | 504.3 (M + H)+ |
| 13.100 | N-Butyl-N-(4-tert-butyl-benzyl)-5-chloro-2-methylamino-nicotinamide | 1 | 388.3 (M + H)+ |
| 13.101 | 5-Chloro-2-cyclopropylamino-N-[2-(3,4-dichloro-phenyl)-ethyl]-N-[4-(1,2,2,2-tetrafluoro-1-trifluoromethyl-ethyl)-benzyl]-nicotinamide | 1 | 642.2 (M + H)+ |

-continued

| Ex. | Name | * | MS (ISP) |
|---|---|---|---|
| 13.102 | 5-Chloro-2-cyclopropylamino-N-[2-(4-fluoro-phenyl)-ethyl]-N-[4-(1,2,2,2-tetrafluoro-1-trifluoromethyl-ethyl)-benzyl]-nicotinamide | 1 | 592.3 (M + H)+ |
| 13.103 | N-(4-tert-Butyl-benzyl)-5-chloro-2-cyclopropylamino-N-[2-(3-trifluoromethyl-phenyl)-ethyl]-nicotinamide | 1 | 530.3 (M + H)+ |
| 13.104 | 5-Chloro-N-(4-cyclobutyl-benzyl)-N-[2-(3,4-dichloro-phenyl)-ethyl]-2-methylamino-nicotinamide | 1 | 502.2 (M + H)+ |
| 13.105 | 5-Chloro-N-(4-cyclopentyl-benzyl)-N-[2-(3,4-dichloro-phenyl)-ethyl]-2-methylamino-nicotinamide | 1 | 516.3 (M + H)+ |
| 13.106 | 5-Chloro-2-cyclopropylamino-N-[4-(1,2,2,2-tetrafluoro-1-trifluoromethyl-ethyl)-benzyl]-N-[2-(3-trifluoromethyl-phenyl)-ethyl]-nicotinamide | 1 | 642.3 (M + H)+ |
| 13.107 | 5-Chloro-N-(4-cyclobutyl-benzyl)-2-cyclopropylamino-N-[2-(3,4-dichloro-phenyl)-ethyl]-nicotinamide | 1 | 528.1 (M + H)+ |
| 13.108 | 5-Amino-pyrimidine-4-carboxylic acid (4-tert-butyl-benzyl)-[2-(3,4-dichloro-phenyl)-ethyl]-amide | 4 | 457.4 (M + H)+ |
| 13.109 | 5-Methylamino-pyrimidine-4-carboxylic acid (4-tert-butyl-benzyl)-[2-(3,4-dichloro-phenyl)-ethyl]-amide | 3 | 471.3 (M + H)+ |
| 13.110 | N-(4-tert-Butyl-benzyl)-N-[2-(3,4-dichloro-phenyl)-ethyl]-2-methylamino-benzamide | 1 | 469.4 (M + H)+ |
| 13.111 | 6-Chloro-3-methylamino-pyridine-2-carboxylic acid [2-(3,4-dichloro-phenyl)-ethyl]-[4-(1,2,2,2-tetrafluoro-1-trifluoromethyl-ethyl)-benzyl]-amide | 1 | 615.9 (M + H)+ |
| 13.112 | 6-Chloro-3-methylamino-pyridine-2-carboxylic acid [2-(4-fluoro-phenyl)-ethyl]-[4-(1,2,2,2-tetrafluoro-1-trifluoromethyl-ethyl)-benzyl]-amide | 1 | 566.0 (M + H)+ |
| 13.113 | 6-Chloro-3-methylamino-pyridine-2-carboxylic acid [4-(1,2,2,2-tetrafluoro-1-trifluoromethyl-ethyl)-benzyl]-[2-(3-trifluoromethyl-phenyl)-ethyl]-amide | 1 | 616.0 (M + H)+ |
| 13.114 | 6-Chloro-3-methylamino-pyridine-2-carboxylic acid (4-tert-butyl-benzyl)-[2-(3-trifluoromethyl-phenyl)-ethyl]-amide | 1 | 504.0 (M + H)+ |
| 13.115 | 6-Chloro-3-methylamino-pyridine-2-carboxylic acid butyl-(4-tert-butyl-benzyl)-amide | 1 | 388.2 (M + H)+ |
| 13.116 | 6-Chloro-3-cyclopropylamino-pyridine-2-carboxylic acid (4-tert-butyl-benzyl)-[2-(3,4-dichloro-phenyl)-ethyl]-amide | 1 | 530.0 (M + H)+ |
| 13.117 | 6-Chloro-3-cyclopropylamino-pyridine-2-carboxylic acid [2-(3,4-dichloro-phenyl)-ethyl]-[4-(1,2,2,2-tetrafluoro-1-trifluoromethyl-ethyl)-benzyl]-amide | 1 | 642.0 (M + H)+ |
| 13.118 | 6-Chloro-3-cyclopropylamino-pyridine-2-carboxylic acid [2-(4-fluoro-phenyl)-ethyl]-[4-(1,2,2,2-tetrafluoro-1-trifluoromethyl-ethyl)-benzyl]-amide | 1 | 592.0 (M + H)+ |
| 13.119 | 6-Chloro-3-cyclopropylamino-pyridine-2-carboxylic acid [4-(1,2,2,2-tetrafluoro-1-trifluoromethyl-ethyl)-benzyl]-[2-(3-trifluoromethyl-phenyl)-ethyl]-amide | 1 | 642.0 (M + H)+ |
| 13.120 | 6-Chloro-3-methylamino-pyridazine-4-carboxylic acid (4-tert-butyl-benzyl)-[2-(3,4-dichloro-phenyl)-ethyl]-amide | 1 | 505.0 (M + H)+ |
| 13.121 | 5-Fluoro-N-[2-(4-fluoro-phenyl)-ethyl]-2-methylamino-N-[4-(1,2,2,2-tetrafluoro-1-trifluoromethyl-ethyl)-benzyl]-nicotinamide | 1 | 550.2 (M + H)+ |
| 13.122 | N-(4-Cyclobutyl-benzyl)-N-[2-(3,4-dichloro-phenyl)-ethyl]-2-ethylamino-5-fluoro-nicotinamide | 1 | 500.1 (M + H)+ |
| 13.123 | 6-Chloro-3-methylamino-pyridazine-4-carboxylic acid [4-(1,2,2,2-tetrafluoro-1-trifluoromethyl-ethyl)-benzyl]-[2-(3-trifluoromethyl-phenyl)-ethyl]-amide | 1 | 617.0 (M + H)+ |
| 13.124 | 6-Chloro-3-methylamino-pyridazine-4-carboxylic acid (4-cyclobutyl-benzyl)-[2-(3-trifluoromethyl-phenyl)-ethyl]-amide | 1 | 503.0 (M + H)+ |
| 13.125 | 5-Bromo-N-[2-(3,4-dichloro-phenyl)-ethyl]-2-methyl-amino-N-[4-(1,2,2,2-tetrafluoro-1-trifluoromethyl-ethyl)-benzyl]-nicotinamide | 1 | 659.8 (M + H)+ |
| 13.126 | 5-Bromo-N-(4-cyclobutyl-benzyl)-N-[2-(3,4-dichloro-phenyl)-ethyl]-2-methylamino-nicotinamide | 1 | 545.9 (M + H)+ |
| 13.127 | 5-Chloro-N-(4-cyclobutyl-benzyl)-2-methylamino-N-[2-(3-trifluoromethyl-phenyl)-ethyl]-nicotinamide | 1 | 502.1 (M + H)+ |
| 13.128 | 6-Methoxy-3-methylamino-pyridazine-4-carboxylic acid (4-tert-butyl-benzyl)-[2-(3,4-dichloro-phenyl)-ethyl]-amide | 1 | 501.1 (M + H)+ |
| 13.129 | 2-Amino-N-(4-tert-butyl-benzyl)-N-[2-(3,4-dichloro-phenyl)-ethyl]-nicotinamide | 1 | 456.0 (M + H)+ |
| 13.130 | 6-Chloro-3-methylamino-pyridazine-4-carboxylic acid [2-(3,4-dichloro-phenyl)-ethyl]-[4-(1,2,2,2-tetrafluoro-1-trifluoromethyl-ethyl)-benzyl]-amide | 1 | 616.9 (M + H)+ |

-continued

| Ex. | Name | * | MS (ISP) |
|---|---|---|---|
| 13.131 | 2-Ethylamino-5-fluoro-N-[2-(4-fluoro-phenyl)-ethyl]-N-[4-(1,2,2,2-tetrafluoro-1-trifluoromethyl-ethyl)-benzyl]-nicotinamide | 1 | 564.4 (M + H)+ |
| 13.132 | 3-Methylamino-pyridazine-4-carboxylic acid (4-tert-butyl-benzyl)-[2-(3,4-dichloro-phenyl)-ethyl]-amide | 1 | 471.2 (M + H)+ |
| 13.133 | N-(4-tert-Butyl-benzyl)-N-[2-(3,4-dichloro-phenyl)-ethyl]-5-methyl-2-methylamino-nicotinamide | 1 | 484.5 (M + H)+ |
| 13.134 | 5-Chloro-N-[2-(4-chloro-phenyl)-ethyl]-2-methylamino-N-[4-(1,2,2,2-tetrafluoro-1-trifluoromethyl-ethyl)-benzyl]-nicotinamide | 1 | 582.1 (M + H)+ |
| 13.135 | 5-Chloro-N-(4-cyclopropyl-benzyl)-2-methylamino-N-[2-(3-trifluoromethyl-phenyl)-ethyl]-nicotinamide | 1 | 488.3 (M + H)+ |
| 13.136 | 5-Chloro-N-[2-(4-chloro-phenyl)-ethyl]-N-(4-cyclopropyl-benzyl)-2-methylamino-nicotinamide | 1 | 454.3 (M + H)+ |
| 13.137 | #!(4-tert-Butyl-benzyl)-N-[2-(3,4-dichloro-phenyl)-ethyl]-2-ethylamino-5-methyl-nicotinamide | 1 | 498.3 (M + H)+ |
| 13.138 | 5-Chloro-N-(4-cyclopropyl-benzyl)-2-ethylamino-N-[2-(3-trifluoromethyl-phenyl)-ethyl]-nicotinamide | 1 | 502.2 (M + H)+ |
| 13.139 | 6-Chloro-3-methylamino-pyridine-2-carboxylic acid [2-(4-chloro-phenyl)-ethyl]-[4-(1,2,2,2-tetrafluoro-1-trifluoromethyl-ethyl)-benzyl]-amide | 1 | 582.1 (M + H)+ |
| 13.140 | 6-Chloro-3-methylamino-pyridine-2-carboxylic acid (4-cyclopropyl-benzyl)-[2-(3-trifluoromethyl-phenyl)-ethyl]-amide | 1 | 488.3 (M + H)+ |
| 13.141 | 6-Chloro-3-methylamino-pyridine-2-carboxylic acid [2-(4-chloro-phenyl)-ethyl]-(4-cyclopropyl-benzyl)-amide | 1 | 454.3 (M + H)+ |
| 13.142 | N-(4-tert-Butyl-benzyl)-N-[2-(3,4-dichloro-phenyl)-ethyl]-2-methylamino-5-phenyl-nicotinamide | 4 | 546.3 (M + H)+ |
| 13.143 | 3-Amino-6-methyl-pyridine-2-carboxylic acid (4-tert-butyl-benzyl)-[2-(3-trifluoromethyl-phenyl)-ethyl]-amide | 1 | 470.4 (M + H)+ |
| 13.144 | 3-Amino-6-methyl-pyrazine-2-carboxylic acid (4-tert-butyl-benzyl)-[2-(3,4-dichloro-phenyl)-ethyl]-amide | 1 | 471.2 (M + H)+ |
| 13.145 | 3-Amino-6-chloro-pyrazine-2-carboxylic acid (4-tert-butyl-benzyl)-[2-(3,4-dichloro-phenyl)-ethyl]-amide | 1 | 491.2 (M + H)+ |
| 13.146 | 6-Chloro-3-methylamino-pyrazine-2-carboxylic acid (4-tert-butyl-benzyl)-[2-(3,4-dichloro-phenyl)-ethyl]-amide | 3 | 505.3 (M + H)+ |
| 13.147 | 6-Methyl-3-methylamino-pyrazine-2-carboxylic acid (4-tert-butyl-benzyl)-[2-(3,4-dichloro-phenyl)-ethyl]-amide | 3 | 485.4 (M + H)+ |
| 13.148 | 6-Chloro-3-ethylamino-pyridine-2-carboxylic acid (4-tert-butyl-benzyl)-[2-(3,4-dichloro-phenyl)-ethyl]-amide | 1 | 518.2 (M + H)+ |
| 13.149 | 6-Chloro-3-ethylamino-pyridine-2-carboxylic acid (4-tert-butyl-benzyl)-[2-(3-trifluoromethyl-phenyl)-ethyl]-amide | 1 | 518.3 (M + H)+ |
| 13.150 | N-(4-tert-Butyl-benzyl)-2-chloro-N-[2-(3,4-dichloro-phenyl)-ethyl]-5-methylamino-isonicotinamide | 1 | 504.0 (M + H)+ |
| 13.151 | N-(4-tert-Butyl-benzyl)-2-chloro-5-methylamino-N-[2-(3-trifluoromethyl-phenyl)-ethyl]-isonicotinamide | 1 | 504.3 (M + H)+ |
| 13.152 | 6-Chloro-3-methylamino-pyridine-2-carboxylic acid (4-tert-butyl-benzyl)-phenethyl-amide | 1 | 436.3 (M + H)+ |
| 13.153 | 6-Chloro-3-methylamino-pyridine-2-carboxylic acid [2-(3,4-dichloro-phenyl)-ethyl]-(4-(pentafluorothio)-benzyl)-amide | 1 | 573.9 (M + H)+ |
| 13.154 | N-(4-tert-Butyl-benzyl)-N-[2-(3,4-dichloro-phenyl)-ethyl]-2-methylamino-5-vinyl-nicotinamide | 4 | 496.4 (M + H)+ |
| 13.155 | 2-Chloro-N-[2-(3,4-dichloro-phenyl)-ethyl]-5-methyl-amino-N-[4-(1,2,2,2-tetrafluoro-1-trifluoromethyl-ethyl)-benzyl]-isonicotinamide | 1 | 616.3 (M + H)+ |
| 13.156 | 5-Amino-2-chloro-pyrimidine-4-carboxylic acid (4-tert-butyl-benzyl)-[2-(3,4-dichloro-phenyl)-ethyl]-amide | 1 | 491.2 (M + H)+ |
| 13.157 | 2-Chloro-5-methylamino-pyrimidine-4-carboxylic acid (4-tert-butyl-benzyl)-[2-(3,4-dichloro-phenyl)-ethyl]-amide | 3 | 505.3 (M + H)+ |
| 13.158 | 5-Chloro-N-[2-(3,4-dichloro-phenyl)-ethyl]-N-(4-iso-propyl-benzyl)-2-methylamino-nicotinamide | 1 | 490.2 (M + H)+ |
| 13.159 | 6-Chloro-3-methylamino-pyridine-2-carboxylic acid (4-cyclobutyl-benzyl)-[2-(3,4-dichloro-phenyl)-ethyl]-amide | 1 | 502.2 (M + H)+ |
| 13.160 | 6-Chloro-3-methylamino-pyridine-2-carboxylic acid (4-cyclobutyl-benzyl)-[2-(3-trifluoromethyl-phenyl)-ethyl]-amide | 1 | 502.3 (M + H)+ |
| 13.161 | 2-Chloro-N-(4-cyclobutyl-benzyl)-N-[2-(3,4-dichloro-phenyl)-ethyl]-5-methylamino-isonicotinamide | 1 | 502.2 (M + H)+ |
| 13.162 | 2-Chloro-N-(4-cyclobutyl-benzyl)-5-methylamino-N-[2-(3-trifluoromethyl-phenyl)-ethyl]-isonicotinamide | 1 | 502.3 (M + H)+ |

-continued

| Ex. | Name | * | MS (ISP) |
|---|---|---|---|
| 13.163 | 2-Chloro-N-[2-(4-chloro-phenyl)-ethyl]-5-methylamino-N-[4-(1,2,2,2-tetrafluoro-1-trifluoromethyl-ethyl)-benzyl]-isonicotinamide | 1 | 582.2 (M + H)+ |
| 13.164 | 2-Chloro-5-methylamino-N-[4-(1,2,2,2-tetrafluoro-1-trifluoromethyl-ethyl)-benzyl]-N-[2-(3-trifluoromethyl-phenyl)-ethyl]-isonicotinamide | 1 | 616.4 (M + H)+ |
| 13.165 | 5-Chloro-N-[4-(1-fluoro-cyclopropyl)-benzyl]-2-methylamino-N-[2-(3-trifluoromethyl-phenyl)-ethyl]-nicotinamide | 1 | 506.2 (M + H)+ |
| 13.166 | 5-Chloro-N-[4-(1-fluoro-cyclopropyl)-benzyl]-2-methylamino-N-[2-(3-trifluoromethyl-phenyl)-ethyl]-benzamide | 1 | 505.3 (M + H)+ |
| 13.167 | 5-Chloro-N-(4-isopropyl-benzyl)-2-methylamino-N-[2-(3-trifluoromethyl-phenyl)-ethyl]-nicotinamide | 1 | 489.4 (M + H)+ |
| 13.168 | 5-Chloro-N-(4-isopropyl-benzyl)-2-methylamino-N-[2-(3-trifluoromethyl-phenyl)-ethyl]-benzamide | 1 | 489.4 (M + H)+ |
| 13.169 | 6-Chloro-3-methylamino-pyrazine-2-carboxylic acid (4-isopropyl-benzyl)-[2-(3-trifluoromethyl-phenyl)-ethyl]-amide | 1 | 491.3 (M + H)+ |
| 13.170 | 6-Chloro-3-methylamino-pyrazine-2-carboxylic acid (4-tert-butyl-benzyl)-[2-(3-trifluoromethyl-phenyl)-ethyl]-amide | 1 | 505.3 (M + H)+ |
| 13.171 | 5-Chloro-2-methylamino-N-(4-methyl-benzyl)-N-[2-(3-trifluoromethyl-phenyl)-ethyl]-benzamide | 1 | 461.3 (M + H)+ |
| 13.172 | 5-Chloro-N-(4-ethyl-benzyl)-2-methylamino-N-[2-(3-trifluoromethyl-phenyl)-ethyl]-benzamide | 1 | 475.3 (M + H)+ |
| 13.173 | 5-Chloro-N-(4-ethyl-benzyl)-2-methylamino-N-[2-(3-trifluoromethyl-phenyl)-ethyl]-nicotinamide | 1 | 476.3 (M + H)+ |
| 13.174 | 6-Chloro-3-methylamino-pyridine-2-carboxylic acid (4-isopropyl-benzyl)-[2-(3-trifluoromethyl-phenyl)-ethyl]-amide | 1 | 490.3 (M + H)+ |
| 13.175 | 2-Chloro-N-(4-isopropyl-benzyl)-5-methylamino-N-[2-(3-trifluoromethyl-phenyl)-ethyl]-isonicotinamide | 1 | 490.5 (M + H)+ |
| 13.176 | 5-Chloro-N-[2-(4-chloro-phenyl)-ethyl]-N-[4-(1-fluoro-cyclopropyl)-benzyl]-2-methylamino-benzamide | 1 | 471.2 (M + H)+ |
| 13.177 | 5-Chloro-N-(4-isopropyl-benzyl)-2-methylamino-N-[2-(3-trifluoromethoxy-phenyl)-ethyl]-nicotinamide | 1 | 506.2 (M + H)+ |
| 13.178 | 5-Chloro-N-(4-isopropyl-benzyl)-2-methylamino-N-[2-(3-trifluoromethoxy-phenyl)-ethyl]-benzamide | 1 | 505.3 (M + H)+ |
| 13.179 | 5-Chloro-N-[2-(4-chloro-phenyl)-ethyl]-N-(4-isopropyl-benzyl)-2-methylamino-nicotinamide | 1 | 456.4 (M + H)+ |
| 13.180 | 5-Chloro-N-[2-(4-chloro-phenyl)-ethyl]-N-(4-isopropyl-benzyl)-2-methylamino-benzamide | 1 | 455.3 (M + H)+ |
| 13.181 | 6-Chloro-3-methylamino-pyridine-2-carboxylic acid (4-tert-butyl-benzyl)-(2,2-difluoro-2-phenyl-ethyl)-amide | 1 | 472.3 (M + H)+ |
| 13.182 | N-(4-tert-Butyl-benzyl)-5-chloro-N-{2-[(4-chloro-phenyl)-methyl-amino]-ethyl}-2-methylamino-nicotinamide | 1 | 499.2 (M + H)+ |
| 13.183 | N-(4-tert-Butyl-benzyl)-5-chloro-N-{2-[(4-chloro-phenyl)-methyl-amino]-ethyl}-2-methylamino-benzamide | 1 | 498.2 (M + H)+ |
| 13.184 | 5-Chloro-2-methylamino-N-(4-pentafluoroethyl-benzyl)-N-[2-(3-trifluoromethyl-phenyl)-ethyl]-benzamide | 1 | 565.3 (M + H)+ |
| 13.185 | 6-Chloro-3-methylamino-pyridine-2-carboxylic acid (4-pentafluoroethyl-benzyl)-[2-(3-trifluoromethyl-phenyl)-ethyl]-amide | 1 | 566.3 (M + H)+ |
| 13.186 | 5-Chloro-2-methylamino-N-(4-pentafluoroethyl-benzyl)-N-[2-(3-trifluoromethoxy-phenyl)-ethyl]-benzamide | 1 | 581.1 (M + H)+ |
| 13.187 | 6-Chloro-3-methylamino-pyridine-2-carboxylic acid (4-pentafluoroethyl-benzyl)-[2-(3-trifluoromethoxy-phenyl)-ethyl]-amide | 1 | 582.0 (M + H)+ |
| 13.188 | 5-Chloro-N-[2-(4-chloro-phenyl)-ethyl]-2-methylamino-N-(4-pentafluoroethyl-benzyl)-benzamide | 1 | 531.2 (M + H)+ |
| 13.189 | 6-Chloro-3-methylamino-pyridine-2-carboxylic acid [2-(4-chloro-phenyl)-ethyl]-(4-pentafluoroethyl-benzyl)-amide | 1 | 532.1 (M + H)+ |
| 13.190 | 5-Chloro-N-[2-(3-methoxy-phenyl)-ethyl]-2-methyl-amino-N-(4-pentafluoroethyl-benzyl)-benzamide | 1 | 527.2 (M + H)+ |
| 13.191 | 6-Chloro-3-methylamino-pyridine-2-carboxylic acid [2-(3-methoxy-phenyl)-ethyl]-(4-pentafluoroethyl-benzyl)-amide | 1 | 528.2 (M + H)+ |
| 13.192 | 5-Chloro-2-methylamino-N-(4-pentafluoroethyl-benzyl)-N-(2-p-tolyl-ethyl)-benzamide | 1 | 511.4 (M + H)+ |
| 13.193 | 6-Chloro-3-methylamino-pyridine-2-carboxylic acid (4-pentafluoroethyl-benzyl)-(2-p-tolyl-ethyl)-amide | 1 | 512.5 (M + H)+ |

-continued

| Ex. | Name | * | MS (ISP) |
|---|---|---|---|
| 13.194 | 5-Chloro-N-[2-(4-fluoro-phenyl)-ethyl]-2-methylamino-N-(4-pentafluoroethyl-benzyl)-benzamide | 1 | 515.4 (M + H)+ |
| 13.195 | 6-Chloro-3-methylamino-pyridine-2-carboxylic acid[2-(4-fluoro-phenyl)-ethyl]-(4-pentafluoroethyl-benzyl)-amide | 1 | 516.3 (M + H)+ |
| 13.196 | 5-Chloro-N-[2-(4-fluoro-phenyl)-ethyl]-2-methylamino-N-(4-pentafluoroethyl-benzyl)-nicotinamide | 1 | 516.2 (M + H)+ |
| 13.197 | 5-Chloro-N-[2-(4-chloro-phenyl)-ethyl]-2-methylamino-N-(4-pentafluoroethyl-benzyl)-nicotinamide | 1 | 532.1 (M + H)+ |
| 13.198 | 5-Chloro-2-methylamino-N-(4-pentafluoroethyl-benzyl)-N-[2-(3-trifluoromethoxy-phenyl)-ethyl]-nicotinamide | 1 | 582.0 (M + H)+ |
| 13.199 | 5-Chloro-N-[2-(3-methoxy-phenyl)-ethyl]-2-methylamino-N-(4-pentafluoroethyl-benzyl)-nicotinamide | 1 | 528.2 (M + H)+ |
| 13.200 | 5-Chloro-2-methylamino-N-(4-pentafluoroethyl-benzyl)-N-(2-p-tolyl-ethyl)-nicotinamide | 1 | 512.4 (M + H)+ |
| 13.201 | N-(4-tert-Butyl-benzyl)-5-chloro-N-[2-(4-chloro-phenylamino)-ethyl]-2-methylamino-benzamide | 1 | 484.5 (M + H)+ |
| 13.202 | N-(4-tert-Butyl-benzyl)-5-chloro-2-methylamino-N-(2-naphthalen-2-yl-ethyl)-benzamide | 1 | 485.4 (M + H)+ |
| 13.203 | 6-Chloro-3-methylamino-pyridine-2-carboxylic acid (4-tert-butyl-benzyl)-[2-(4-chloro-phenylamino)-ethyl]-amide | 1 | 485.3 (M + H)+ |
| 13.204 | 6-Chloro-3-methylamino-pyridine-2-carboxylic acid (4-tert-butyl-benzyl)-(2-naphthalen-2-yl-ethyl)-amide | 1 | 486.4 (M + H)+ |
| 13.205 | 5-Chloro-2-methylamino-N-(4-pentafluoroethyl-benzyl)-N-[2-(3-trifluoromethyl-phenyl)-ethyl]-nicotinamide | 1 | 566.3 (M + H)+ |
| 13.206 | 2-Chloro-5-methylamino-N-(4-pentafluoroethyl-benzyl)-N-[2-(3-trifluoromethyl-phenyl)-ethyl]-isonicotinamide | 1 | 566.3 (M + H)+ |
| 13.207 | 2-Chloro-N-[2-(4-chloro-phenyl)-ethyl]-5-methylamino-N-(4-pentafluoroethyl-benzyl)-isonicotinamide | 1 | 532.2 (M + H)+ |
| 13.208 | 5-Chloro-2-ethylamino-N-(4-pentafluoroethyl-benzyl)-N-[2-(3-trifluoromethyl-phenyl)-ethyl]-benzamide | 1 | 579.3 (M + H)+ |
| 13.209 | 5-Chloro-N-[2-(4-chloro-phenyl)-ethyl]-2-ethylamino-N-(4-pentafluoroethyl-benzyl)-benzamide | 1 | 545.3 (M + H)+ |
| 13.210 | N-(4-tert-Butyl-benzyl)-5-chloro-2-methylamino-N-(2-phenoxy-ethyl)-benzamide | 1 | 451.2 (M + H)+ |
| 13.211 | 6-Chloro-3-methylamino-pyridine-2-carboxylic acid (4-tert-butyl-benzyl)-(2-phenoxy-ethyl)-amide | 1 | 452.3 (M + H)+ |
| 13.212 | 6-Chloro-3-methylamino-pyrazine-2-carboxylic acid (4-cyclobutyl-benzyl)-[2-(4-fluoro-phenyl)-ethyl]-amide | 1 | 453.1 (M + H)+ |
| 13.213 | 6-Chloro-3-methylamino-pyrazine-2-carboxylic acid (4-cyclobutyl-benzyl)-[2-(3-trifluoromethyl-phenyl)-ethyl]-amide | 1 | 503.0 (M + H)+ |
| 13.214 | 6-Chloro-3-methylamino-pyrazine-2-carboxylic acid [2-(4-chloro-phenyl)-ethyl]-(4-cyclobutyl-benzyl)-amide | 1 | 469.2 (M + H)+ |
| 13.215 | 6-Chloro-3-methylamino-pyridine-2-carboxylic acid [2-(4-chloro-phenyl)-ethyl]-(4-cyclobutyl-benzyl)-amide | 1 | 468.1 (M + H)+ |
| 13.216 | 6-Chloro-3-methylamino-pyridine-2-carboxylic acid (4-cyclobutyl-benzyl)-[2-(4-fluoro-phenyl)-ethyl]-amide | 1 | 452.1 (M + H)+ |
| 13.217 | 3-Amino-6-methyl-pyridine-2-carboxylic acid [2-(4-chloro-phenyl)-ethyl]-(4-cyclobutyl-benzyl)-amide | 1 | 434.4 (M + H)+ |
| 13.218 | 3-Amino-6-methyl-pyridine-2-carboxylic acid (4-cyclobutyl-benzyl)-[2-(4-fluoro-phenyl)-ethyl]-amide | 1 | 418.3 (M + H)+ |
| 13.219 | 3-Amino-6-methyl-pyridine-2-carboxylic acid (4-cyclobutyl-benzyl)-[2-(3-trifluoromethyl-phenyl)-ethyl]-amide | 1 | 468.5 (M + H)+ |
| 13.220 | 6-Methyl-3-methylamino-pyridine-2-carboxylic acid (4-cyclobutyl-benzyl)-[2-(4-fluoro-phenyl)-ethyl]-amide | 3 | 432.4 (M + H)+ |
| 13.221 | 6-Methyl-3-methylamino-pyridine-2-carboxylic acid (4-cyclobutyl-benzyl)-[2-(3-trifluoromethyl-phenyl)-ethyl]-amide | 3 | 482.5 (M + H)+ |
| 13.222 | N-(4-tert-Butyl-benzyl)-5-chloro-3-fluoro-2-methylamino-N-[2-(3-trifluoromethyl-phenyl)-ethyl]-benzamide | 1 | 521.4 (M + H)+ |
| 13.223 | N-(4-tert-Butyl-benzyl)-5-chloro-N-[2-(3,4-dichloro-phenyl)-ethyl]-3-fluoro-2-methylamino-benzamide | 1 | 521.3 (M + H)+ |
| 13.224 | 2-Acetylamino-N-(4-tert-butyl-benzyl)-5-chloro-3-fluoro-N-[2-(3-trifluoromethyl-phenyl)-ethyl]-benzamide | 1 | 549.4 (M + H)+ |

-continued

| Ex. | Name | * | MS (ISP) |
|---|---|---|---|
| 13.225 | 2-Amino-N-(4-tert-butyl-benzyl)-5-chloro-N-[2-(4-fluoro-phenyl)-ethyl]-3-iodo-benzamide | 1 | 565.1 (M + H)+ |
| 13.226 | N-(4-tert-Butyl-benzyl)-2,3-dichloro-6-methylamino-N-[2-(3-trifluoromethyl-phenyl)-ethyl]-benzamide | 5 | 537.5 (M + H)+ |
| 13.227 | 6-Amino-N-(4-tert-butyl-benzyl)-2,3-dichloro-N-[2-(3-trifluoromethyl-phenyl)-ethyl]-benzamide | 5 | 522.2 (M + H)+ |
| 13.228 | N-(4-tert-Butyl-benzyl)-2,3-dichloro-6-(cyclopropane-carbonyl-amino)-N-[2-(3-trifluoromethyl-phenyl)-ethyl]-benzamide | 6 | 591.5 (M + H)+ |
| 13.229 | 6-Acetylamino-N-(4-tert-butyl-benzyl)-2,3-dichloro-N-[2-(3-trifluoromethyl-phenyl)-ethyl]-benzamide | 6 | 565.4 (M + H)+ |
| 13.230 | N-(4-tert-Butyl-benzyl)-2,3-dichloro-6-propionylamino-N-[2-(3-trifluoromethyl-phenyl)-ethyl]-benzamide | 6 | 579.4 (M + H)+ |
| 13.231 | 6-Amino-N-(4-tert-butyl-benzyl)-2,3-dichloro-N-[2-(3-difluoromethoxy-phenyl)-ethyl]-benzamide | 1 | 521.5 (M + H)+ |
| 13.232 | 6-Acetylamino-N-(4-tert-butyl-benzyl)-2,3-dichloro-N-[2-(3-difluoromethoxy-phenyl)-ethyl]-benzamide | 6 | 580.3 (M + H)+ |
| 13.233 | N-(4-tert-Butyl-benzyl)-2,3-dichloro-N-[2-(3-difluoromethoxy-phenyl)-ethyl]-6-propionylamino-benzamide | 6 | 577.3 (M + H)+ |
| 13.234 | 2-Amino-N-(4-tert-butyl-benzyl)-6-chloro-N-[2-(3-trifluoromethyl-phenyl)-ethyl]-benzamide | 1 | 489.4 (M + H)+ |
| 13.235 | 2-Amino-N-(4-tert-butyl-benzyl)-6-methyl-N-[2-(3-trifluoromethyl-phenyl)-ethyl]-benzamide | 1 | 469.5 (M + H)+ |
| 13.236 | 2-Acetylamino-N-(4-tert-butyl-benzyl)-6-chloro-N-[2-(3-trifluoromethyl-phenyl)-ethyl]-benzamide | 6 | 531.3 (M + H)+ |
| 13.237 | 2-Acetylamino-N-(4-tert-butyl-benzyl)-6-methyl-N-[2-(3-trifluoromethyl-phenyl)-ethyl]-benzamide | 6 | 511.5 (M + H)+ |
| 13.238 | 2-Amino-N-(4-tert-butyl-benzyl)-5-chloro-N-[2-(3-trifluoromethoxy-phenyl)-ethyl]-benzamide | 1 | 505.1 (M + H)+ |
| 13.239 | 2-Acetylamino-N-butyl-N-(4-tert-butyl-benzyl)-5-chloro-benzamide | 6 | 415.3 (M + H)+ |
| 13.240 | 2-Acetylamino-N-(4-tert-butyl-benzyl)-5-chloro-N-[2-(3-trifluoromethoxy-phenyl)-ethyl]-benzamide | 6 | 547.3 (M + H)+ |
| 13.241 | 6-Amino-N-(4-tert-butyl-benzyl)-3-chloro-2-fluoro-N-[2-(3-trifluoromethyl-phenyl)-ethyl]-benzamide | 1 | 507.1 (M + H)+ |
| 13.242 | 2-Amino-N-(4-tert-butyl-benzyl)-3-chloro-6-fluoro-N-[2-(3-trifluoromethyl-phenyl)-ethyl]-benzamide | 1 | 507.3 (M + H)+ |
| 13.243 | N-(4-tert-Butyl-benzyl)-2,3-dichloro-6-(2,2,2-trifluoro-acetylamino)-N-[2-(3-trifluoromethyl-phenyl)-ethyl]-benzamide | 6 | 619.3 (M + H)+ |
| 13.244 | 6-Acetylamino-N-(4-tert-butyl-benzyl)-3-chloro-2-fluoro-N-[2-(3-trifluoromethyl-phenyl)-ethyl]-benzamide | 6 | 549.4 (M + H)+ |
| 13.245 | 2-Amino-N-(4-tert-butyl-benzyl)-5-chloro-N-[2-(2-chloro-phenyl)-ethyl]-benzamide | 1 | 455.4 (M + H)+ |
| 13.246 | 2-Amino-N-(4-tert-butyl-benzyl)-5-chloro-N-[2-(3-chloro-phenyl)-ethyl]-benzamide | 1 | 455.4 (M + H)+ |
| 13.247 | 2-Acetylamino-N-(4-tert-butyl-benzyl)-5-chloro-N-[2-(2-chloro-phenyl)-ethyl]-benzamide | 6 | 496.2 (M + H)+ |
| 13.248 | 2-Acetylamino-N-(4-tert-butyl-benzyl)-5-chloro-N-[2-(3-chloro-phenyl)-ethyl]-benzamide | 6 | 496.2 (M + H)+ |
| 13.249 | 2-Acetylamino-N-(4-tert-butyl-benzyl)-3-chloro-6-fluoro-N-[2-(3-trifluoromethyl-phenyl)-ethyl]-benzamide | 6 | 549.4 (M + H)+ |
| 13.250 | 2-Amino-N-(4-tert-butyl-benzyl)-5-chloro-N-[2-(4-chloro-phenyl)-ethyl]-benzamide | 1 | 455.4 (M + H)+ |
| 13.251 | 2-Amino-N-(4-tert-butyl-benzyl)-5-chloro-N-[2-(4-methoxy-phenyl)-ethyl]-benzamide | 1 | 451.2 (M + H)+ |
| 13.252 | 2-Acetylamino-N-(4-tert-butyl-benzyl)-5-chloro-N-[2-(4-chloro-phenyl)-ethyl]-benzamide | 6 | 497.1 (M + H)+ |
| 13.253 | 2-Acetylamino-N-(4-tert-butyl-benzyl)-5-chloro-N-[2-(4-methoxy-phenyl)-ethyl]-benzamide | 6 | 493.2 (M + H)+ |
| 13.254 | N-(4-tert-Butyl-benzyl)-3-chloro-6-fluoro-2-methylamino-N-[2-(3-trifluoromethyl-phenyl)-ethyl]-benzamide | 3 | 521.4 (M + H)+ |
| 13.255 | 2-Amino-N-(4-tert-butyl-benzyl)-3,5-dichloro-6-fluoro-N-[2-(3-trifluoromethyl-phenyl)-ethyl]-benzamide | 1 | 541.3 (M + H)+ |
| 13.256 | 2-Acetylamino-5-chloro-N-[(R)-2-(4-chloro-phenyl)-2-hydroxy-ethyl]-N-(4-cyclopropyl-benzyl)-benzamide | 6 | 497 (M + H)+ |
| 13.257 | 2-Acetylamino-N-(4-tert-butyl-benzyl)-3,5-dichloro-6-fluoro-N-[2-(3-trifluoromethyl-phenyl)-ethyl]-benzamide | 6 | 583 (M + H)+ |
| 13.258 | 2-Amino-3,5-dichloro-N-[(R)-2-(4-chloro-phenyl)-2-hydroxy-ethyl]-N-(4-cyclopropyl-benzyl)-6-fluoro-benzamide | 6 | 507.2 (M + H)+ |

-continued

| Ex. | Name | * | MS (ISP) |
|---|---|---|---|
| 13.259 | 6-Acetylamino-2,3-dichloro-N-[(R)-2-(4-chloro-phenyl)-2-hydroxy-ethyl]-N-(4-cyclopropyl-benzyl)-benzamide | 6 | 531.2 (M + H)+ |
| 13.260 | 2-Acetylamino-3,5-dichloro-N-[(R)-2-(4-chloro-phenyl)-2-hydroxy-ethyl]-N-(4-cyclopropyl-benzyl)-6-fluoro-benzamide | 6 | 549.3 (M + H)+ |
| 13.261 | 2-Acetylamino-5-chloro-N-(4-cyclopropyl-benzyl)-N-[2-(3-trifluoromethoxy-phenyl)-ethyl]-benzamide | 6 | 531.3 (M + H)+ |
| 13.262 | 2-Acetylamino-5-chloro-N-(4-cyclopropyl-benzyl)-N-[2-(3-trifluoromethyl-phenyl)-ethyl]-benzamide | 6 | 515.3 (M + H)+ |
| 13.263 | 2-Amino-3,5-dichloro-N-(4-cyclopropyl-benzyl)-6-fluoro-N-[2-(3-trifluoromethoxy-phenyl)-ethyl]-benzamide | 1 | 541.3 (M + H)+ |
| 13.264 | 2-Amino-3,5-dichloro-N-(4-cyclopropyl-benzyl)-6-fluoro-N-[2-(3-trifluoromethyl-phenyl)-ethyl]-benzamide | 1 | 525.3 (M + H)+ |
| 13.265 | 6-Acetylamino-2,3-dichloro-N-(4-cyclopropyl-benzyl)-N-[2-(3-trifluoromethoxy-phenyl)-ethyl]-benzamide | 6 | 565.3 (M + H)+ |
| 13.266 | 6-Acetylamino-2,3-dichloro-N-(4-cyclopropyl-benzyl)-N-[2-(3-trifluoromethyl-phenyl)-ethyl]-benzamide | 6 | 549.2 (M + H)+ |
| 13.267 | 2-Amino-3,5-dichloro-N-(2-chloro-4-cyclopropyl-benzyl)-6-fluoro-N-[2-(3-trifluoromethyl-phenyl)-ethyl]-benzamide | 1 | 559.1 (M + H)+ |
| 13.268 | 2-Acetylamino-3,5-dichloro-N-(2-chloro-4-cyclopropyl-benzyl)-6-fluoro-N-[2-(3-trifluoromethyl-phenyl)-ethyl]-benzamide | 1 | 601.0 (M + H)+ |
| 13.269 | 2-Acetylamino-3,5-dichloro-N-(4-cyclopropyl-benzyl)-6-fluoro-N-[2-(3-trifluoromethoxy-phenyl)-ethyl]-benzamide | 6 | 583 (M + H)+ |
| 13.270 | 2-Acetylamino-3,5-dichloro-N-(4-cyclopropyl-benzyl)-6-fluoro-N-[2-(3-trifluoromethyl-phenyl)-ethyl]-benzamide | 6 | 567.2 (M + H)+ |
| 13.271 | 2-Amino-5-chloro-N-(2-chloro-4-cyclopropyl-benzyl)-N-[2-(3-trifluoromethyl-phenyl)-ethyl]-benzamide | 1 | 507.2 (M + H)+ |
| 13.272 | 2-Acetylamino-5-chloro-N-(2-chloro-4-cyclopropyl-benzyl)-N-[2-(3-trifluoromethyl-phenyl)-ethyl]-benzamide | 6 | 547.2 (M + H)+ |
| 13.273 | 5-Chloro-N-(4-cyclopropyl-benzyl)-2-methylamino-N-[2-(3-trifluoromethyl-phenyl)-ethyl]-benzamide | 7 | 587.2 (M + H)+ |
| 13.274 | 5-Chloro-2-(cyanomethyl-amino)-N-(4-cyclopropyl-benzyl)-N-[2-(3-trifluoromethoxy-phenyl)-ethyl]-benzamide | 7 | 528.1 (M + H)+ |
| 13.275 | 5-Chloro-2-(cyanomethyl-amino)-N-(4-cyclopropyl-benzyl)-N-[2-(3-trifluoromethyl-phenyl)-ethyl]-benzamide | 7 | 511.3 (M + H)+ |
| 13.276 | 2,3-Dichloro-6-(cyanomethyl-amino)-N-(4-cyclopropyl-benzyl)-N-[2-(3-trifluoromethoxy-phenyl)-ethyl]-benzamide | 7 | 579.1 (M + H)+ |
| 13.277 | 2,3-Dichloro-N-(4-cyclopropyl-benzyl)-6-methylamino-N-[2-(3-trifluoromethoxy-phenyl)-ethyl]-benzamide | 7 | 537.2 (M + H)+ |
| 13.278 | 2,3-Dichloro-6-(cyanomethyl-amino)-N-(4-cyclopropyl-benzyl)-N-[2-(3-trifluoromethyl-phenyl)-ethyl]-benzamide | 7 | 563.3 (M + H)+ |
| 13.279 | 2,3-Dichloro-N-(4-cyclopropyl-benzyl)-6-methylamino-N-[2-(3-trifluoromethyl-phenyl)-ethyl]-benzamide | 7 | 521.2 (M + H)+ |
| 13.280 | 5-Chloro-N-(4-cyclopropyl-benzyl)-2-ethylamino-N-[2-(3-trifluoromethyl-phenyl)-ethyl]-benzamide | 1 | 501.1 (M + H)+ |
| 13.281 | 5-Chloro-N-(4-cyclopropyl-benzyl)-2-ethylamino-N-[2-(3-trifluoromethoxy-phenyl)-ethyl]-benzamide | 1 | 517.2 (M + H)+ |
| 13.282 | N-(4-tert-Butyl-benzyl)-5-chloro-2-ethylamino-N-[2-(3-trifluoromethoxy-phenyl)-ethyl]-benzamide | 1 | 533.2 (M + H)+ |
| 13.283 | 5-Chloro-N-(4-cyclopropyl-2-fluoro-benzyl)-2-ethyl-amino-N-[2-(3-trifluoromethyl-phenyl)-ethyl]-benzamide | 1 | 519.1 (M + H)+ |
| 13.284 | 5-Chloro-N-(4-cyclopropyl-3-fluoro-benzyl)-2-ethyl-amino-N-[2-(3-trifluoromethyl-phenyl)-ethyl]-benzamide | 1 | 519.1 (M + H)+ |
| 13.285 | 3,5-Dichloro-N-(4-cyclopropyl-benzyl)-2-fluoro-6-methylamino-N-[2-(3-trifluoromethyl-phenyl)-ethyl]-benzamide | 7 | 539.2 (M + H)+ |
| 13.286 | 2-Acetylamino-3,5-dichloro-N-(4-cyclopropyl-benzyl)-N-[2-(3-trifluoromethoxy-phenyl)-ethyl]-benzamide | 6 | 565.2 (M + H)+ |
| 13.287 | 3,5-Dichloro-N-(4-cyclopropyl-benzyl)-2-methylamino-N-[2-(3-trifluoromethoxy-phenyl)-ethyl]-benzamide | 7 | 537.2 (M + H)+ |
| 13.288 | 3,5-Dichloro-N-(4-cyclopropyl-benzyl)-2-ethylamino-N-[2-(3-trifluoromethoxy-phenyl)-ethyl]-benzamide | 7 | 550.1 (M + H)+ |

-continued

| Ex. | Name | * | MS (ISP) |
|---|---|---|---|
| 13.289 | 3,5-Dichloro-2-(cyanomethyl-amino)-N-(4-cyclopropyl-benzyl)-N-[2-(3-trifluoromethoxy-phenyl)-ethyl]-benzamide | 7 | 562.3 (M + H)+ |
| 13.290 | 3,5-Dichloro-2-(cyanomethyl-amino)-N-(4-cyclopropyl-benzyl)-6-fluoro-N-[2-(3-trifluoromethyl-phenyl)-ethyl]-benzamide | 7 | 564.2 (M + H)+ |
| 13.291 | 5-Chloro-N-[2-(4-chloro-phenyl)-ethyl]-N-(4-cyclopropyl-benzyl)-2-methylamino-benzamide | 7 | 452.9 (M + H)+ |
| 13.292 | 5-Chloro-N-(4-cyclopropyl-benzyl)-N-[2-(4-fluoro-phenyl)-ethyl]-2-methylamino-benzamide | 7 | 437 (M + H)+ |
| 13.293 | (2-{(4-tert-Butyl-benzyl)-[2-(3-trifluoromethoxy-phenyl)-ethyl]-carbamoyl}-4-chloro-phenylamino)-acetic acid ethyl ester | 7 | 591.2 (M + H)+ |
| 13.294 | 5-Chloro-N-[2-(4-chloro-phenyl)-ethyl]-N-(4-cyclopropyl-benzyl)-2-ethylamino-benzamide | 7 | 467.4 (M + H)+ |
| 13.295 | 5-Chloro-N-[2-(4-chloro-phenyl)-ethyl]-2-(cyanomethyl-amino)-N-(4-cyclopropyl-benzyl)-benzamide | 7 | 478.4 (M + H)+ |
| 13.296 | 5-Chloro-N-[2-(4-chloro-phenyl)-ethyl]-2-methylamino-N-[4-(1,2,2,2-tetrafluoro-1-trifluoromethyl-ethyl)-benzyl]-benzamide | 7 | 581.1 (M + H)+ |
| 13.297 | N-(4-tert-Butyl-benzyl)-5-chloro-2-(cyanomethyl-amino)-N-[2-(3-trifluoromethoxy-phenyl)-ethyl]-benzamide | 7 | 544.3 (M + H)+ |
| 13.298 | N-(4-tert-Butyl-benzyl)-5-chloro-2-(cyanomethyl-amino)-N-[2-(3-trifluoromethyl-phenyl)-ethyl]-benzamide | 7 | 519.4 (M + H)+ |
| 13.299 | 5-Chloro-2-methylamino-N-(4-trifluoromethoxy-benzyl)-N-[2-(3-trifluoromethyl-phenyl)-ethyl]-benzamide | 7 | 531.1 (M + H)+ |
| 13.300 | 5-Chloro-2-ethylamino-N-(4-trifluoromethoxy-benzyl)-N-[2-(3-trifluoromethyl-phenyl)-ethyl]-benzamide | 7 | 545.2 (M + H)+ |
| 13.301 | 5-Chloro-N-[2-(4-chloro-phenyl)-ethyl]-2-ethylamino-N-[4-(1,2,2,2-tetrafluoro-1-trifluoromethyl-ethyl)-benzyl]-benzamide | 7 | 595.1 (M + H)+ |
| 13.302 | 5-Chloro-N-[2-(4-chloro-phenyl)-ethyl]-2-(cyanomethyl-amino)-N-[4-(1,2,2,2-tetrafluoro-1-trifluoromethyl-ethyl)-benzyl]-benzamide | 7 | 606.4 (M + H)+ |
| 13.303 | 5-Chloro-2-(cyanomethyl-amino)-N-(4-trifluoromethoxy-benzyl)-N-[2-(3-trifluoromethyl-phenyl)-ethyl]-benzamide | 7 | 556.0 (M + H)+ |
| 13.304 | 5-Chloro-N-[2-(4-fluoro-phenyl)-ethyl]-2-methylamino-N-(4-trifluoromethoxy-benzyl)-benzamide | 7 | 481.2 (M + H)+ |
| 13.305 | 5-Chloro-2-ethylamino-N-[2-(4-fluoro-phenyl)-ethyl]-N-(4-trifluoromethoxy-benzyl)-benzamide | 7 | 495.2 (M + H)+ |
| 13.306 | 5-Chloro-2-(cyanomethyl-amino)-N-[2-(4-fluoro-phenyl)-ethyl]-N-(4-trifluoromethoxy-benzyl)-benzamide | 7 | 506.1 (M + H)+ |
| 13.307 | {4-Chloro-2-[[2-(4-fluoro-phenyl)-ethyl]-(4-trifluoromethoxy-benzyl)-carbamoyl]-phenylamino}-acetic acid ethyl ester | 7 | 553.0 (M + H)+ |
| 13.308 | {4-Chloro-2-[[2-(4-fluoro-phenyl)-ethyl]-(4-trifluoromethoxy-benzyl)-carbamoyl]-phenylamino}-acetic acid | 8 | 525 (M + H)+ |
| 13.309 | 5-Chloro-N-(3-chloro-4-trifluoromethoxy-benzyl)-N-[2-(4-fluoro-phenyl)-ethyl]-2-methylamino-benzamide | 7 | 515.0 (M + H)+ |
| 13.310 | 5-Chloro-2-(cyanomethyl-amino)-N-(4-cyclobutyl-benzyl)-N-[2-(3-trifluoromethyl-phenyl)-ethyl]-benzamide | 7 | 525.2 (M + H)+ |
| 13.311 | 5-Chloro-N-(3-chloro-4-trifluoromethoxy-benzyl)-2-ethylamino-N-[2-(4-fluoro-phenyl)-ethyl]-benzamide | 7 | 529.1 (M + H)+ |
| 13.312 | 5-Chloro-N-(3-chloro-4-trifluoromethoxy-benzyl)-2-(cyanomethyl-amino)-N-[2-(4-fluoro-phenyl)-ethyl]-benzamide | 7 | 541.1 (M + H)+ |
| 13.313 | 5-Chloro-N-[2-(4-chloro-phenyl)-ethyl]-2-methylamino-N-(4-trifluoromethoxy-benzyl)-benzamide | 7 | 497 (M + H)+ |
| 13.314 | 5-Chloro-N-[2-(4-chloro-phenyl)-ethyl]-2-ethylamino-N-(4-trifluoromethoxy-benzyl)-benzamide | 7 | 511.2 (M + H)+ |
| 13.315 | 5-Chloro-N-(4-cyclobutyl-benzyl)-2-methylamino-N-[2-(3-trifluoromethyl-phenyl)-ethyl]-benzamide | 7 | 501.1 (M + H)+ |
| 13.316 | 5-Chloro-N-[2-(4-chloro-phenyl)-ethyl]-2-(cyanomethyl-amino)-N-(4-trifluoromethoxy-benzyl)-benzamide | 7 | 522.0 (M + H)+ |
| 13.317 | 5-Chloro-N-[4-(1-methoxy-cyclopropyl)-benzyl]-2-methylamino-N-[2-(3-trifluoromethoxy-phenyl)-ethyl]-benzamide | 7 | 533.2 (M + H)+ |

-continued

| Ex. | Name | * | MS (ISP) |
|---|---|---|---|
| 13.318 | 5-Chloro-2-ethylamino-N-[4-(1-methoxy-cyclopropyl)-benzyl]-N-[2-(3-trifluoromethoxy-phenyl)-ethyl]-benzamide | 7 | 547.3 (M + H)⁺ |
| 13.319 | 5-Chloro-2-(cyanomethyl-amino)-N-[4-(1-methoxy-cyclopropyl)-benzyl]-N-[2-(3-trifluoromethoxy-phenyl)-ethyl]-benzamide | 7 | 558.2 (M + H)⁺ |
| 13.320 | 5-Chloro-N-(4-cyclobutyl-benzyl)-2-methylamino-N-[2-(3-trifluoromethoxy-phenyl)-ethyl]-benzamide | 7 | 517.2 (M + H)⁺ |
| 13.321 | 5-Chloro-N-(4-cyclobutyl-benzyl)-2-ethylamino-N-[2-(3-trifluoromethoxy-phenyl)-ethyl]-benzamide | 7 | 530.2 (M + H)⁺ |
| 13.322 | 5-Chloro-2-(cyanomethyl-amino)-N-(4-cyclobutyl-benzyl)-N-[2-(3-trifluoromethoxy-phenyl)-ethyl]-benzamide | 7 | 541.1 (M + H)⁺ |
| 13.323 | N-(4-Benzyloxy-benzyl)-5-chloro-2-methylamino-N-[2-(3-trifluoromethyl-phenyl)-ethyl]-benzamide | 1 | 553.1 (M + H)⁺ |
| 13.324 | [4-({(5-Chloro-2-methylamino-benzoyl)-[2-(3-trifluoromethyl-phenyl)-ethyl]-amino}-methyl)-phenoxy]-acetic acid methyl ester | 9 | 535.0 (M + H)⁺ |
| 13.325 | N-(4-tert-Butyl-benzyl)-2,3-dichloro-N-[2-(4-chloro-phenyl)-ethyl]-6-methylamino-benzamide | 1 | 503.0 (M + H)⁺ |
| 13.326 | 2,3-Dichloro-N-[2-(4-chloro-phenyl)-ethyl]-6-methyl-amino-N-[4-(1,2,2,2-tetrafluoro-1-trifluoromethyl-ethyl)-benzyl]-benzamide | 1 | 615.2 (M + H)⁺ |
| 13.327 | N-(4-tert-Butyl-benzyl)-2,3-dichloro-6-methylamino-N-[2-(3-trifluoromethoxy-phenyl)-ethyl]-benzamide | 1 | 553.4 (M + H)⁺ |
| 13.328 | N-(4-tert-Butyl-benzyl)-2,3-dichloro-N-[2-(4-fluoro-phenyl)-ethyl]-6-methylamino-benzamide | 1 | 487.3 (M + H)⁺ |
| 13.329 | 5-Chloro-N-[4-(4-cyano-benzyloxy)-benzyl]-2-methyl-amino-N-[2-(3-trifluoromethyl-phenyl)-ethyl]-benzamide | 9 | 578.2 (M + H)⁺ |
| 13.330 | 5-Chloro-N-[4-(4-fluoro-benzyloxy)-benzyl]-2-methyl-amino-N-[2-(3-trifluoromethyl-phenyl)-ethyl]-benzamide | 9 | 571.2 (M + H)⁺ |
| 13.331 | 2,3-Dichloro-N-[4-(1-methoxy-cyclopropyl)-benzyl]-6-methylamino-N-[2-(3-trifluoromethyl-phenyl)-ethyl]-benzamide | 1 | 551.1 (M + H)⁺ |
| 13.332 | 5-Chloro-N-[2-(4-chloro-phenyl)-ethyl]-N-[4-(1-methoxy-cyclopropyl)-benzyl]-2-methylamino-benzamide | 1 | 483.2 (M + H)⁺ |
| 13.333 | 2,3-Dichloro-N-[2-(4-chloro-phenyl)-ethyl]-N-[4-(1-methoxy-cyclopropyl)-benzyl]-6-methylamino-benzamide | 1 | 517.1 (M + H)⁺ |
| 13.334 | 6-Chloro-3-methylamino-pyridine-2-carboxylic acid (4-tert-butyl-benzyl)-[2-(3-trifluoromethoxy-phenyl)-ethyl]-amide | 1 | 519.3 (M + H)⁺ |
| 13.335 | N-(4-tert-Butoxy-benzyl)-2,3-dichloro-N-[2-(4-chloro-phenyl)-ethyl]-6-methylamino-benzamide | 1 | 519.2 (M + H)⁺ |
| 13.336 | N-(4-tert-Butoxy-benzyl)-5-chloro-N-[2-(4-chloro-phenyl)-ethyl]-2-methylamino-benzamide | 1 | 485.2 (M + H)⁺ |
| 13.337 | 5-Chloro-N-[2-(4-chloro-phenyl)-ethyl]-2-methylamino-N-(4-trifluoromethyl-benzyl)-benzamide | 1 | 481.0 (M + H)⁺ |
| 13.338 | 2,3-Dichloro-N-[2-(4-chloro-phenyl)-ethyl]-6-methyl-amino-N-(4-trifluoromethyl-benzyl)-benzamide | 1 | 515.0 (M + H)⁺ |
| 13.339 | 5-Chloro-N-[2-(4-chloro-phenyl)-ethyl]-2-methylamino-N-[4-(1,1,2,2-tetrafluoro-ethoxy)-benzyl]-benzamide | 1 | 529.0 (M + H)⁺ |
| 13.340 | 5-Chloro-N-[2-(4-chloro-phenyl)-ethyl]-2-methylamino-N-(4-phenoxy-benzyl)-benzamide | 1 | 505.2 (M + H)⁺ |
| 13.341 | 2,3-Dichloro-N-[2-(4-chloro-phenyl)-ethyl]-6-methyl-amino-N-[4-(1,1,2,2-tetrafluoro-ethoxy)-benzyl]-benzamide | 1 | 563.3 (M + H)⁺ |
| 13.342 | 2,3-Dichloro-N-[2-(4-chloro-phenyl)-ethyl]-6-methyl-amino-N-(4-phenoxy-benzyl)-benzamide | 1 | 541.3 (M + H)⁺ |
| 13.343 | 5-Chloro-2-methylamino-N-[4-(3,3,3-trifluoro-2-hydroxy-propoxy)-benzyl]-N-[2-(3-trifluoromethyl-phenyl)-ethyl]-benzamide | 9 | 575.3 (M + H)⁺ |
| 13.344 | Methanesulfonic acid 4-({(5-chloro-2-methylamino-benzoyl)-[2-(3-trifluoromethyl-phenyl)-ethyl]-amino}-methyl)-phenyl ester | 9 | 541.1 (M + H)⁺ |
| 13.345 | N-(4-tert-Butoxy-benzyl)-5-chloro-N-[2-(4-chloro-phenyl)-ethyl]-2-ethylamino-benzamide | 1 | 499.3 (M + H)⁺ |
| 13.346 | N-(4-tert-Butoxy-benzyl)-5-chloro-N-[2-(4-chloro-phenyl)-ethyl]-2-methylamino-nicotinamide | 1 | 486.2 (M + H)⁺ |
| 13.347 | 6-Chloro-3-methylamino-pyridine-2-carboxylic acid (4-tert-butoxy-benzyl)-[2-(4-chloro-phenyl)-ethyl]-amide | 1 | 486.2 (M + H)⁺ |
| 13.348 | N-(4-tert-Butoxy-benzyl)-5-chloro-2-methylamino-N-[2-(3-trifluoromethyl-phenyl)-ethyl]-benzamide | 1 | 519.2 (M + H)⁺ |

-continued

| Ex. | Name | * | MS (ISP) |
|---|---|---|---|
| 13.349 | 6-Chloro-3-methylamino-pyridine-2-carboxylic acid (4-tert-butoxy-benzyl)-[2-(3-trifluoromethyl-phenyl)-ethyl]-amide | 1 | 520.3 (M + H)+ |
| 13.350 | N-(4-tert-Butoxy-benzyl)-5-chloro-2-methylamino-N-[2-(3-trifluoromethyl-phenyl)-ethyl]-nicotinamide | 1 | 520.3 (M + H)+ |
| 13.351 | 5-Chloro-N-(4-cyclopropylmethoxy-benzyl)-2-methyl-amino-N-[2-(3-trifluoromethyl-phenyl)-ethyl]-benzamide | 9 | 517.2 (M + H)+ |
| 13.352 | N-(4-tert-Butoxy-benzyl)-5-chloro-2-methylamino-N-[2-(3-trifluoromethoxy-phenyl)-ethyl]-benzamide | 1 | 535.4 (M + H)+ |
| 13.353 | 6-Chloro-3-methylamino-pyridine-2-carboxylic acid (4-tert-butoxy-benzyl)-[2-(3-trifluoromethoxy-phenyl)-ethyl]-amide | 1 | 536.3 (M + H)+ |
| 13.354 | N-(4-tert-Butoxy-benzyl)-5-chloro-N-[2-(4-fluoro-phenyl)-ethyl]-2-methylamino-benzamide | 1 | 469.2 (M + H)+ |
| 13.355 | 6-Chloro-3-methylamino-pyridine-2-carboxylic acid (4-tert-butoxy-benzyl)-[2-(4-fluoro-phenyl)-ethyl]-amide | 1 | 470.2 (M + H)+ |
| 13.356 | N-(4-tert-Butoxy-benzyl)-5-chloro-N-[2-(4-fluoro-phenyl)-ethyl]-2-methylamino-nicotinamide | 1 | 470.2 (M + H)+ |
| 13.357 | N-(4-tert-Butoxy-benzyl)-5-chloro-2-methylamino-N-[2-(3-trifluoromethoxy-phenyl)-ethyl]-nicotinamide | 1 | 536.4 (M + H)+ |
| 13.358 | N-(4-tert-Butyl-benzyl)-5-chloro-2-ethylamino-N-[2-(4-fluoro-phenyl)-ethyl]-benzamide | 1 | 466.0 (M + H)+ |
| 13.359 | N-(4-tert-Butyl-benzyl)-5-chloro-N-[2-(4-chloro-phenyl)-ethyl]-2-ethylamino-benzamide | 1 | 482 (M + H)+ |
| 13.360 | 2-Amino-N-(4-tert-butyl-benzyl)-3,5-dichloro-N-[2-(3-trifluoromethyl-phenyl)-ethyl]-benzamide | 1 | 523.2 (M + H)+ |
| 13.361 | 2-Amino-N-(4-tert-butyl-benzyl)-3,5-dimethyl-N-[2-(3-trifluoromethyl-phenyl)-ethyl]-benzamide | 1 | 483.4 (M + H)+ |
| 13.362 | 2-Amino-3,5-dibromo-N-(4-tert-butyl-benzyl)-N-[2-(3-trifluoromethyl-phenyl)-ethyl]-benzamide | 1 | 613.2 (M + H)+ |
| 13.363 | 2-Amino-N-(4-tert-butyl-benzyl)-5-methyl-N-[2-(3-trifluoromethyl-phenyl)-ethyl]-benzamide | 1 | 469.2 (M + H)+ |
| 13.364 | N-(4-tert-Butyl-benzyl)-2-methylamino-N-[2-(3-trifluoromethyl-phenyl)-ethyl]-benzamide | 1 | 469.2 (M + H)+ |
| 13.365 | 2-Amino-N-(4-tert-butyl-benzyl)-5-iodo-N-[2-(3-trifluoromethyl-phenyl)-ethyl]-benzamide | 1 | 581.1 (M + H)+ |
| 13.366 | 2-Amino-5-bromo-N-(4-tert-butyl-benzyl)-N-[2-(3-trifluoromethyl-phenyl)-ethyl]-benzamide | 1 | 535.3 (M + H)+ |
| 13.367 | 3,5-Dibromo-N-(4-tert-butyl-benzyl)-2-methylamino-N-[2-(3-trifluoromethyl-phenyl)-ethyl]-benzamide | 11 | 627.2 (M + H)+ |
| 13.368 | 2-Amino-3-bromo-N-(4-tert-butyl-benzyl)-5-iodo-N-[2-(3-trifluoromethyl-phenyl)-ethyl]-benzamide | 11 | 661.0 (M + H)+ |
| 13.369 | 2-Amino-5-bromo-N-(4-tert-butyl-benzyl)-3-chloro-N-[2-(3-trifluoromethyl-phenyl)-ethyl]-benzamide | 12 | 569.1 (M + H)+ |
| 13.370 | 2-Amino-N-(4-tert-butyl-benzyl)-3-chloro-5-iodo-N-[2-(3-trifluoromethyl-phenyl)-ethyl]-benzamide | 12 | 615.3 (M + H)+ |
| 13.371 | N-(4-tert-Butyl-benzyl)-N-[2-(3-fluoro-4-trifluoromethyl-phenyl)-ethyl]-2-methylamino-benzamide | 1 | 487.4 (M + H)+ |
| 13.372 | N-(4-tert-Butyl-benzyl)-N-[2-(2-fluoro-3-trifluoromethyl-phenyl)-ethyl]-2-methylamino-benzamide | 1 | 487.4 (M + H)+ |
| 13.373 | N-(4-tert-Butyl-benzyl)-N-[2-(3-chloro-2-fluoro-phenyl)-ethyl]-2-methylamino-benzamide | 1 | 453.3 (M + H)+ |
| 13.374 | N-(4-tert-Butyl-benzyl)-N-[2-(3-chloro-4-fluoro-phenyl)-ethyl]-2-methylamino-benzamide | 1 | 453.3 (M + H)+ |
| 13.375 | N-(4-tert-Butyl-benzyl)-N-[2-(3-difluoromethoxy-phenyl)-ethyl]-2-methylamino-benzamide | 1 | 467.4 (M + H)+ |
| 13.376 | N-(4-tert-Butyl-benzyl)-N-[2-(4-chloro-phenyl)-ethyl]-2-methylamino-benzamide | 1 | 435.3 (M + H)+ |
| 13.377 | N-(4-tert-Butyl-benzyl)-N-[2-(4-chloro-3-fluoro-phenyl)-ethyl]-2-methylamino-benzamide | 1 | 453.4 (M + H)+ |
| 13.378 | N-(4-tert-Butyl-benzyl)-2-methylamino-N-[2-(3 trifluoromethoxy-phenyl)-ethyl]-benzamide | 1 | 485.5 (M + H)+ |
| 13.379 | N-(4-tert-Butyl-benzyl)-5-chloro-2-ethylamino-N-[2-(3 trifluoromethyl-phenyl)-ethyl]-benzamide | 5 | 517.5 (M + H)+ |
| 13.380 | N-(4-tert-Butyl-benzyl)-5-chloro-2-methylamino-N-[2-(3-trifluoromethyl-phenyl)-ethyl]-benzamide | 5 | 503.5 (M + H)+ |
| 13.381 | 2-Amino-N-(4-tert-butyl-benzyl)-5-chloro-N-[2-(3-trifluoromethyl-phenyl)-ethyl]-benzamide | 1 | 489.4 (M + H)+ |
| 13.382 | N-(4-tert-Butyl-benzyl)-2-(cyanomethyl)-amino)-N-[2-(3-trifluoromethyl-phenyl)-ethyl]-benzamide | 1 | 494.5 (M + H)+ |
| 13.383 | N-(4-tert-Butyl-benzyl)-5-chloro-N-[2-(3-chloro-4-fluoro-phenyl)-ethyl]-2-methylamino-benzamide | 5 | 487.3 (M + H)+ |
| 13.384 | N-(4-tert-Butyl-benzyl)-5-chloro-N-[2-(3,4-dichloro-phenyl)-ethyl]-2-methylamino-benzamide | 5 | 505.3 (M + H)+ |

-continued

| Ex. | Name | * | MS (ISP) |
|---|---|---|---|
| 13.385 | N-(4-tert-Butyl-benzyl)-5-chloro-N-[2-(3-difluorometh-oxy-phenyl)-ethyl]-2-methylamino-benzamide | 5 | 501.2 (M + H)$^+$ |
| 13.386 | N-(4-tert-Butyl-benzyl)-5-chloro-N-[2-(4-chloro-phenyl)-ethyl]-2-methylamino-benzamide | 5 | 469.4 (M + H)$^+$ |
| 13.387 | N-(4-tert-Butyl-benzyl)-5-chloro-2-(cyclopropylmethyl-amino)-N-[2-(3-trifluoromethyl-phenyl)-ethyl]-benzamide | 5 | ** |
| 13.388 | (2-{(4-tert-Butyl-benzyl)-[2-(3-trifluoromethyl-phenyl)-ethyl]-carbamoyl}-4-chloro-phenyl)-carbamic acid methyl ester | 6 | 545.3 (M − H)$^+$ |
| 13.389 | N-(4-tert-Butyl-benzyl)-5-chloro-2-isopropylamino-N-[2-(3-trifluoromethyl-phenyl)-ethyl]-benzamide | 1 | 531.3 (M + H)$^+$ |
| 13.390 | N-(4-tert-Butyl-benzyl)-3-chloro-2-fluoro-6-methylamino-N-[2-(3-trifluoromethyl-phenyl)-ethyl]-benzamide | 1 | 521.4 (M + H)$^+$ |
| 13.391 | 2-Amino-5-chloro-N-[2-(3-trifluoromethyl-phenyl)-ethyl]-N-(4-trimethylsilanyl-benzyl)-benzamide | 1 | 505.3 (M + H)$^+$ |
| 13.392 | 2-Amino-5-chloro-N-[2-(4-chloro-phenyl)-ethyl]-N-(4-trimethylsilanyl-benzyl)-benzamide | 1 | 471.2 (M + H)$^+$ |
| 13.393 | 2-Amino-5-chloro-N-[2-(4-fluoro-phenyl)-ethyl]-N-(4-trimethylsilanyl-benzyl)-benzamide | 1 | 455.4 (M + H)$^+$ |
| 13.394 | 2-Amino-5-chloro-N-[2-(3,4-dichloro-phenyl)-ethyl]-N-(4-trimethylsilanyl-benzyl)-benzamide | 1 | 507.4 (M + H)$^+$ |
| 13.395 | N-Butyl-N-(4-tert-butyl-benzyl)-2-methylamino-benzamide | 1 | 353.5 (M + H)$^+$ |
| 13.396 | N-(4-tert-Butyl-benzyl)-2,3-dichloro-6-methanesulfonylamino-N-[2-(3-trifluoromethyl-phenyl)-ethyl]-benzamide | 6 | 599.1 (M − H)$^-$ |
| 13.397 | N-(4-tert-Butyl-benzyl)-5-chloro-2-methanesulfonyl-amino-N-[2-(3-trifluoromethyl-phenyl)-ethyl]-benzamide | 6 | 529.2 (M + H)$^+$ |

*: Prepared in analogy to example
**: $^1$H-NMR (CDCl$_3$, 300 MHz): 0.24(q, 2H), 0.53(q, 2H), 0.87(q, 1H), 1.31(s, 9H), 2.91(m, 4H), 3.56(br s, 2H), 4.50(br s, 2H), 6.57(d, 1H), 6.95(d, 1H), 6.96-7.18(m, 2H), 7.26-7.50(6H, m).

The compounds of formula I are cholesteryl ester transfer protein (CETP) inhibitors. Atherosclerosis and its associated coronary heart disease is the leading cause of death in the industrialized world. Risk for development of coronary heart disease has been shown to be strongly correlated with certain plasma lipid levels. Lipids are transported in the blood by lipoproteins. The general structure of lipoproteins is a core of neutral lipids (triglyceride and cholesterol ester) and an envelope of polar lipids (phospholipids and non esterified cholesterol). There are three different classes of plasma lipoproteins with different core lipid content: the low density lipoprotein (LDL) which is cholesteryl ester (CE) rich; high density lipoprotein (HDL) which is also cholesteryl ester (CE) rich; and the very low density lipoprotein (VLDL) which is triglyceride (TG) rich. The different lipoproteins can be separated based on their different flotation density or size.

High LDL-cholesterol (LDL-C) and triglyceride levels are positively correlated, while high levels of HDL-cholesterol (HDL-C) are negatively correlated with the risk for developing cardiovascular diseases.

Plasma lipoprotein metabolism can be described as a flux of cholesterol between liver and the other tissues. The LDL pathway corresponds to the secretion of VLDL from the liver to deliver cholesterol by LDL to tissues. Any alteration in LDL catabolism could lead to uptake of excess cholesterol in the vessel wall forming foam cells and atherosclerosis. The opposite pathway is the mobilization of free cholesterol from peripheral tissues by HDL to deliver cholesterol to the liver to be eventually excreted with bile. In humans a significant part of cholesteryl ester (CE) is transferred from HDL to the VLDL, LDL pathway. This transfer is mediated by a 70,000 dalton plasma glycoprotein, the cholesteryl ester transfer protein (CETP).

Mutations in the CETP gene associated with CETP deficiency are characterized by high HDL-cholesterol levels (>60 mg/dL) and reduced cardiovascular risk. Such findings are consistent with studies of pharmacologically mediated inhibition of CETP in the rabbit, which argue strongly in favor of CETP inhibition as a valid therapeutic approach [Le Goff et al., Pharmacology & Therapeutics 101:17-38 (2004); Okamoto et al., Nature 406:203-207 2000)].

No wholly satisfactory HDL-elevating therapies exist. Niacin can significantly increase HDL, but has serious toleration issues which reduce compliance. Fibrates and the HMG CoA reductase inhibitors raise HDL-cholesterol only modestly (−10-12%). As a result, there is a significant unmet medical need for a well tolerated agent which can significantly elevate plasma HDL levels. The net result of CETP activity is a lowering of HDL-C and an increase in LDL-C. This effect on lipoprotein profile is believed to be pro-atherogenic, especially in subjects whose lipid profile constitutes an increased risk for coronary heart disease. Therefore by inhibiting CETP activity there is the potential to inverse this relationship towards a lower risk and ultimately to protect against coronary heart diseases and associated mortality.

Thus, CETP inhibitors are useful as medicaments for the treatment and/or prophylaxis of atherosclerosis, peripheral vascular disease, dyslipidemia, hyperbeta-lipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In addition, CETP inhibitors may be used in combination with another compound, said compound being an HMG-CoA reductase inhibitor, a microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant.

As described above, the compounds of formula I of the present invention can be used as medicaments for the treatment and/or prophylaxis of diseases which are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use as medicament for the treatment and/or prevention of dyslipidemia is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prophylaxis of diseases which are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In another embodiment, the invention relates to a method for the treatment and/or prophylaxis of diseases which are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. A method for the treatment and/or prophylaxis of dyslipidemia is preferred.

The invention further relates to the use of compounds of formula I as defined above for the treatment and/or prophylaxis of diseases are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use of compounds of formula I as defined above for the treatment and/or prophylaxis of dyslipidemia is preferred.

In addition, the invention relates to the use of compounds of formula I as defined above for the preparation of medicaments for the treatment and/or prophylaxis of diseases are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use of compounds of formula I as defined above for the preparation of medicaments for the treatment and/or prophylaxis of dyslipidemia is preferred.

In addition, CETP inhibitors are useful in combination with another compound, said compound being an HMG-CoA reductase inhibitor, an microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant.

The invention therefore also relates to pharmaceutical compositions comprising a compound of formula I as defined above in combination with an HMG-CoA reductase inhibitor, an microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant, as well as a pharmaceutically acceptable carrier and/or adjuvant.

The invention further relates to the use of compounds of formula I as defined above in combination with an HMG-CoA reductase inhibitor, a microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant for the treatment and/or prophylaxis of diseases such as atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia, as well as to the use of such a combination for the preparation of corresponding medicaments.

The compounds of formula I and their pharmaceutically acceptable salts possess valuable pharmacological properties. Specifically, it has been found that the compounds of the present invention are inhibitors of the cholesteryl ester transfer protein (CETP).

The following tests were carried out in order to determine the activity of the compounds of formula I.

Activity of CETP inhibitors was determined using a buffer assay system. Partially purified CETP transferred radiolabeled cholesteryl ester from HDL donor particles to biotin-labeled LDL acceptor particles. The reaction was stopped by addition of streptavidin-coupled scintillation proximity assay (SPA) beads. These beads captured the biotinylated acceptor particles and transferred radioactivity was measured. The assay system was purchased and performed according to manufacturer's recommendations (Amersham Biosciences). Inhibitory activity of compounds was determined as percentage of positive control activity containing CETP together with donor and acceptor particles. Serial dilution of compounds was performed in order to determine the $IC_{50}$ values.

Activity of the compounds was subsequently measured in the presence of plasma using the same assay as described above except that the source of CETP was human lipoproteindeprived serum (LPDS). Inhibitory activity of compounds was determined as percentage of positive control activity containing all the assay components except compound. Serial dilution of compounds was performed in order to determine the $IC_{50}$ values.

Under the latter assay conditions, the compounds of the present invention exhibit $IC_{50}$ values within the range of about 1 nM to about 100 µM, e.g., of about 1 nM to about 1 µM, e.g., of about 1 nM to about 200 nM. The following table shows measured values for some selected compounds of the present invention.

|  | $IC_{50}$ (nM) |
| --- | --- |
| Compound 13.230 | 5610 |
| Compound 13.63 | 30010 |
| Compound 13.254 | 295 |

In vivo activity of the compounds of formula I were determined in hamster using the following protocol:

Male golden Syrian hamsters (6-week-old, 100-130 g) under standard chow diet received compounds in the morning by oral gavage using appropriate vehicle, blood was taken 2 h later by retro-orbital bleeding under isofluran anaesthesia and 7 h later on sacrificed animals. Plasma was separated from blood using low speed centrifugation and CETP activity was measured in plasma using the radioactive CETP activity assay as described above except that diluted plasma replaced LPDS. In vivo CETP inhibition was expressed as CETP activity remaining in the plasma of treated animals as compared to plasma CETP activity of placebo treated animals.

Efficacy of compounds in modulating plasma lipid levels can be determined in hamsters after 7 days of daily administration of compounds. Male hamsters are acclimated for 3-4 days to receive food as a paste made of 10 g chow and 10 g water per day. Compounds are then mixed within this paste and a portion containing the proper amount of compounds is given every morning for 7 days. Alternatively compounds can be given by oral gavage using the proper vehicle. Blood is taken before compound treatment by retro-orbital bleeding and at the end of the treatment on sacrificed animals. Plasma is separated from blood by low speed centrifugation and selected organs are taken (e.g liver, fat, brain, etc.). Effects of compounds on plasma lipid levels are determined by measuring total cholesterol, HDL-cholesterol, LDL-cholesterol and triglyceride using colorimetric enzymatic assays (Roche Diagnostic GmbH, Mannheim, Germany). HDL-C, LDL-C and VLDL-C are e.g., quantified using size exclusion chromatography on superpose-6 column using SMART™ system (Pharmacia). Lipoprotein distribution is calculated assuming a Gaussian distribution for each peak, using a non-linear, least-squares curve-fitting procedure to calculate the area under the curve. Plasma samples are also used to quantify CETP activity as described above. Compound concentration is also determined in plasma and selected tissues as liver, fat, heart, muscle and brain.

Efficacy of compounds in modulating plasma lipid levels was also determined in cholesterol/fat fed hamsters. The protocol is identical as described above except that animals are fed with chow diet enriched with 10% (w/w) saturated fat and 0.05% (w/w) cholesterol. Animals received this high fat diet 2 weeks before starting compound administration and continued this diet throughout the study. The 2 weeks pre-treatment induced an increase in plasma cholesterol and triglyceride levels allowing a better assessment of LDL-C and triglyceride lowering. Efficacy of compounds in its ability to acutely raise HDL-C can be assessed in cynomolgus monkeys. Animals are fed with standard primate maintenance diet. Compounds are formulated with appropriate vehicle and administered to animals by oral gavage. Blood is taken before and at several time-points after compound administration (usually 30 min, 1 h, 2 h, 4 h, 7 h and 24 h). Plasma is separated from blood by low speed centrifugation and CETP activity and plasma lipids are quantified. Compound potency and efficacy can be assessed by measuring the HDL-C increase after this single-dose administration. In such pharmacodynamic model the extent together with the kinetics of the pharmacologic effect can be assessed.

The compounds of formula I and their pharmaceutically acceptable salts and esters can be used as medicaments, e.g. in the form of pharmaceutical preparations for enteral, parenteral or topical administration. They can be administered, e.g., perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, e.g., lactose, corn starch or derivatives thereof, talc, stearic acid or its salts can be used as carrier materials for tablets, coated tablets, dragées and hard gelatine capsules. Suitable carrier materials for soft gelatine capsules are, e.g., vegetable oils, waxes, fats and semi-solid and liquid polyols (depending on the nature of the active ingredient no carriers are, however, required in the case of soft gelatine capsules). Suitable carrier materials for the production of solutions and syrups are, e.g., water, polyols, sucrose, invert sugar and the like. Suitable carrier materials for injection solutions are, e.g., water, alcohols, polyols, glycerol and vegetable oils. Suitable carrier materials for suppositories are, e.g., natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, e.g., 0.5-100 mg, of a compound of formula I.

The following examples serve to illustrate the present invention in more detail. They are, however, not intended to limit its scope in any manner.

EXAMPLE A

Film Coated Tablets

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

EXAMPLE B

Capsules

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

EXAMPLE C

Injection Solutions

| | |
|---|---|
| Compound of formula (I) | 3.0 mg |
| Gelatin | 150.0 mg |
| Phenol | 4.7 mg |
| Sodium carbonate | to obtain a final pH of 7 |
| Water for injection solutions | ad 1.0 ml |

EXAMPLE D

Soft Gelatin Capsules

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

The invention claimed is:

1. A compound of formula (I):

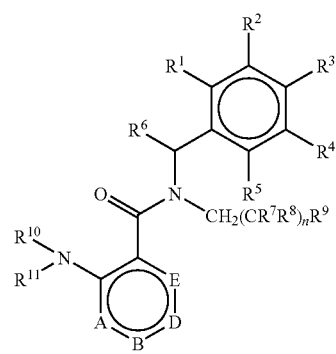

or a pharmaceutically acceptable salt thereof, wherein:
$R^1, R^2, R^4$ and $R^5$ are independently hydrogen, $C_1$-$C_6$alkyl, $C_1$-$C_6$alkoxy or halogen;
$R^3$ is selected from the group consisting of:
(1) $C_3$-$C_6$alkyl,
(2) halogen-$C_1$-$C_6$alkyl,
(3) $C_3$-$C_6$cycloalkyl optionally substituted by halogen or alkoxy,
(4) $Si(C_1$-$C_6$alkyl$)_3$,
(5) —$OR^{12}$, wherein $R^{12}$ is (a) $C_1$-$C_6$alkyl optionally substituted by halogen, hydroxy, $COOC_1$-$C_6$alkyl, $C_3$-$C_6$cycloalkyl or phenyl which phenyl is optionally substituted by halogen or cyano, (b) halogen-$C_1$-$C_6$alkyl, (c) $C_3$-$C_6$cycloalkyl, (d) phenyl, (e) benzyl optionally substituted by halogen or cyano, or (f) $S(O)_2$-$C_1$-$C_6$alkyl, and
(6) pentafluorosulfuranyl; or
$R^2$ and $R^3$ taken together with the carbon atoms they are attached to form a 5- or 6-membered carbocyclic ring or a 5- or 6-membered heterocyclic ring containing one or two heteroatoms selected from N, O or S;
$R^6$ is hydrogen or $C_1$-$C_6$alkyl;

$R^7$ and $R^8$ are independently hydrogen, $C_1$-$C_6$alkyl, hydroxy or halogen;

$R^9$ is selected from the group consisting of:
(1) hydrogen,
(2) $C_1$-$C_6$alkyl,
(3) $C_2$-$C_6$alkenyl,
(4) halogen-$C_1$-$C_6$alkyl,
(5) heterocyclyl,
(6) heteroaryl,
(7) phenyl,
(8) naphthyl, and
(9) —$NR^{14}R^{15}$, wherein $R^{14}$ and $R^{15}$ independently are hydrogen, $C_1$-$C_6$alkyl or phenyl optionally substituted by halogen;

wherein said heteroaryl or phenyl is optionally substituted by: (a) halogen, (b) $C_1$-$C_6$alkyl optionally substituted by halogen, (c) $C_1$-$C_6$alkoxy optionally substituted by halogen or (d) phenyl $R^{10}$ and $R^{11}$ are independently selected from the group consisting of: (1) hydrogen, (2) halogen, (3) $C_1$-$C_6$alkyl optionally substituted by hydroxy, (4) —COR wherein R is $C_1$-$C_6$alkyl optionally substituted by halogen, $C_1$-$C_6$alkoxy, or $C_3$-$C_6$cycloalkyl, (5) —$CH_2$—COO—$CH_2CH_3$, —$CH_2$—COOH, or —$CH_2$—$CH_2$—COOH, (6) $S(O)_2$—$C_1$-$C_6$alkyl, (7) $C_3$-$C_6$cycloalkyl, (8) cyano, and (9) phenyl; or together $R^{10}$ and $R^{11}$ are $C_1$-$C_6$alkylene;

A is $CR^{17}$ or N, wherein $R^{17}$ is hydrogen, halogen, $C_1$-$C_6$alkyl, $C_1$-$C_6$alkoxy or $C_2$-$C_6$alkenyl;

B is $CR^{18}$ or N, wherein $R^{18}$ is hydrogen, halogen, $C_1$-$C_6$alkyl, $C_1$-$C_6$alkoxy or $C_2$-$C_6$alkenyl;

D is $CR^{19}$ or N, wherein $R^{19}$ is hydrogen, halogen, $C_1$-$C_6$alkyl, $C_1$-$C_6$alkoxy, $C_2$-$C_6$alkenyl or phenyl; and E is $CR^{20}$ or N, wherein $R^{20}$ is hydrogen, halogen, $C_1$-$C_6$alkyl, $C_1$-$C_6$alkoxy or $C_2$-$C_6$alkenyl; or alternatively, E is $CR^{20}$ and -A-B-D- is —N—O—, —$NR^{21}$—N—, —S—N—, —S—CH— or —CH—S—, wherein $R^{21}$ is hydrogen, halogen, $C_1$-$C_6$alkyl, $C_1$-$C_6$alkoxy or $C_2$-$C_6$alkenyl; or E is N and -A-B-D- is —N—O—, —S—N—, —S—CH—, —CH—CH— or —CH—S—; or E is S and -A-B-D- is —CH—CH—; and n is 1, 2 or 3.

2. A compound of claim 1 wherein $R^3$ is a $C_3$-$C_6$alkyl, halogen-$C_1$-$C_6$alkyl, or $C_3$-$C_6$cycloalkyl.

3. A compound of claim 1 wherein $R^3$ is a $C_3$-$C_6$alkyl or halogen-$C_1$-$C_6$alkyl wherein the halogen is fluoro.

4. A compound of claim 1 wherein $R^9$ is: (1) heteroaryl which is unsubstituted or substituted by one to five substituents selected from the group consisting of halogen, $C_1$-$C_6$alkyl, halogen-$C_1$-$C_6$alkyl and phenyl, or (2) phenyl which is unsubstituted or substituted by one to five substituents selected from the group consisting of halogen, $C_1$-$C_6$alkyl, halogen-$C_1$-$C_6$alkyl and halogen-$C_1$-$C_6$alkoxy.

5. A compound of claim 1 wherein $R^{10}$ is hydrogen or a $C_1$-$C_6$alkyl.

6. A compound of claim 1 wherein $R^{11}$ is hydrogen or $C_1$-$C_6$alkyl.

7. A compound of claim 1 wherein E is $CR^{20}$.

8. A compound of claim 1 wherein E is N.

9. A compound of claim 1 wherein E is S and -A-B-D- is —CH—CH—.

10. A process for the production of a compound of formula I according to claim 1 which process comprises reacting an acid derivative, a compound of formula II

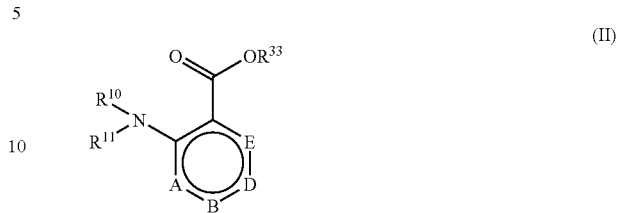

wherein
$R^{33}$ is hydrogen, Li, Na, K or $C_1$-$C_6$alkyl; and
$R^{10}$, $R^{11}$, A, B, D and E have the meanings as defined in claim 1;
with a secondary amine derivative, a compound of formula III

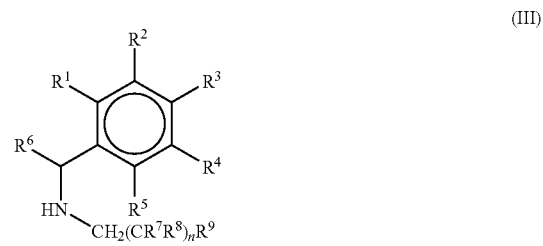

wherein $R^1$, $R^2$, $R^3$, $R^4$, $R^5$, $R^6$, $R^7$, $R^8$, $R^9$ and n have the meanings as defined in claim 1 and optionally converting the resulting compound into a pharmaceutically acceptable salt.

11. A pharmaceutical composition comprising a compound according to claim 1 and a pharmaceutically acceptable carrier, adjuvant, or mixtures thereof.

12. A compound of claim 1 selected from the group consisting of:

5-chloro-N-(4-cyclopentyl-benzyl)-2-isopropylamino-N-[2-(3-trifluoromethyl-phenyl)-ethyl]-benzamide;

N-(4-tert-butyl-benzyl)-N-2-(3,4-dichloro-phenyl)-ethyl-2-methylamino-nicotinamide;

6-methyl-3-methylamino-pyridine-2-carboxylic acid [2-(4-chloro-phenyl)-ethyl]-(4-cyclobutyl-benzyl)-amide;

N-(4-tert-butyl-benzyl)-N-[2-(3,4-dichloro-phenyl)-ethyl]-5-ethyl-2-methylamino-nicotinamide;

N-(4-tert-butylbenzyl)-2-chloro-N-[2-(3,4-dichlorophenyl)-ethyl]-3-fluoro-6-methylaminobenzamide;

2-Acetylamino-N-(4-tert-butyl-benzyl)-5-chloro-N-[2-(3-trifluoromethyl-phenyl)-ethyl]-benzamide;

5-Chloro-N-(4-cyclopropyl-benzyl)-2-methylamino-N-[2-(3-trifluoromethoxy-phenyl)-ethyl]-benzamide;

(2-{(4-tert-Butyl-benzyl)-[2-(3-trifluoromethoxy-phenyl)-ethyl]-carbamoyl}-4-chloro-phenylamino)-acetic acid;

5-Chloro-2-methylamino-N-[4-(3,3,3-trifluoro-2-hydroxy-propoxy)-benzyl]-N-[2-(3-trifluoromethyl-phenyl)-ethyl]-benzamide;

N-(4-tert-Butyl-benzyl)-5-chloro-2-(3-hydroxy-propylamino)-N-[2-(3-trifluoromethyl-phenyl)-ethyl]-benzamide;

3-(2-{(4-tert-butyl-benzyl)-[2-(3-trifluoromethyl-phenyl)-ethyl]-carbamoyl}-4-chloro-phenylamino)-propionic acid;

2-Amino-3-bromo-N-(4-tert-butyl-benzyl)-5-methyl-N-[2-(3-trifluoromethyl-phenyl)-ethyl]-benzamide;
2-Amino-N-(4-tert-butyl-benzyl)-3-chloro-5-methyl-N-[2-(3-trifluoromethyl-phenyl)-ethyl]-benzamide;
N-(4-tert-Butyl-benzyl)-5-chloro-2-(cyanomethyl-amino)-N-[2-(3-trifluoromethyl-phenyl)-ethyl]-benzamide;
6-Chloro-3-methylamino-pyridine-2-carboxylic acid (4-tert-butyl-benzyl)-[2-(2-chloro-pyridin-4-yl)-ethyl]-amide;
N-(4-tert-Butyl-benzyl)-5-chloro-N-[2-(2-chloro-pyridin-4-yl)-ethyl]-2-methylamino-nicotinamide;
N-(4-tert-Butyl-benzyl)-5-chloro-N-[2-(2-chloro-pyridin-4-yl)-ethyl]-2-methylamino-benzamide;
5-Chloro-N-[2-(4-fluoro-phenyl)-ethyl]-2-isopropylamino-N-(4-pentafluoroethyl-benzyl)-benzamide;
5-Chloro-2-isopropylamino-N-[4-(1,2,2,2-tetrafluoro-1-trifluoromethyl-ethyl)-benzyl]-N-[2-(3-trifluoromethyl-phenyl)-ethyl]-benzamide;
5-Chloro-N-[2-(4-fluoro-phenyl)-ethyl]-2-isopropylamino-N-[4-(1,2,2,2-tetrafluoro-1-trifluoromethyl-ethyl)-benzyl]-benzamide;
5-Chloro-N-[2-(3,4-dichloro-phenyl)-ethyl]-2-isopropylamino-N-[4-(1,2,2,2-tetrafluoro-1-trifluoromethyl-ethyl)-benzyl]-benzamide;
5-Chloro-2-isopropylamino-N-(4-pentafluoroethyl-benzyl)-N-[2-(3-trifluoromethoxy-phenyl)-ethyl]-benzamide;
N-(4-tert-Butyl-benzyl)-5-chloro-2-methylamino-N-[2-(4-trifluoromethyl-pyridin-2-yl)-ethyl]-nicotinamide;
N-(4-tert-Butyl-benzyl)-5-chloro-2-methylamino-N-[2-(4-trifluoromethyl-pyridin-2-yl)-ethyl]-benzamide;
6-Chloro-3-methylamino-pyridine-2-carboxylic acid (4-tert-butyl-benzyl)-[2-(5-trifluoromethyl-pyridin-2-yl)-ethyl]-amide;
N-(4-tert-Butyl-benzyl)-5-chloro-2-methylamino-N-[2-(5-trifluoromethyl-pyridin-2-yl)-ethyl]-benzamide;
6-Chloro-3-methylamino-pyridine-2-carboxylic acid (4-tert-butyl-benzyl)-[2-(6-trifluoromethyl-pyridin-2-yl)-ethyl]-amide;
N-(4-tert-Butyl-benzyl)-5-chloro-2-methylamino-N-[2-(6-trifluoromethyl-pyridin-2-yl)-ethyl]-nicotinamide;
N-(4-tert-Butyl-benzyl)-5-chloro-2-methylamino-N-[2-(6-trifluoromethyl-pyridin-2-yl)-ethyl]-benzamide;
5-Chloro-N-(4-cyclobutyl-benzyl)-N-[2-(3,4-dichloro-phenyl)-ethyl]-2-isopropylamino-benzamide;
5-Chloro-N-(4-cyclobutyl-benzyl)-2-isopropylamino-N-[2-(3-trifluoromethyl-phenyl)-ethyl]-benzamide;
N-(4-tert-Butyl-benzyl)-5-chloro-N-[2-(5-chloro-pyridin-2-yl)-ethyl]-2-methylamino-benzamide;
5-Chloro-N-[4-(1-fluoro-cyclobutyl)-benzyl]-2-methylamino-N-[2-(3-trifluoromethyl-phenyl)-ethyl]-benzamide;
5-Chloro-N-[2-(3,4-dichloro-phenyl)-ethyl]-N-[4-(1-fluoro-cyclobutyl)-benzyl]-2-methylamino-benzamide;
5-Chloro-N-[2-(3,4-dichloro-phenyl)-ethyl]-N-[4-(1-methoxy-cyclobutyl)-benzyl]-2-methylamino-nicotinamide;
N-(4-tert-Butyl-benzyl)-5-chloro-2-cyclopropylamino-N-[2-(3,4-dichloro-phenyl)-ethyl]-benzamide;
N-(4-tert-Butyl-benzyl)-5-chloro-2-cyclopropylamino-N-[2-(3-trifluoromethyl-phenyl)-ethyl]-benzamide;
N-(4-cyclobutyl-benzyl)-2-cyclopropylamino-5-trifluoromethyl-N-[2-(3-trifluoromethyl-phenyl)-ethyl]-benzamide;
5-Chloro-N-(4-cyclobutyl-benzyl)-N-[2-(3,4-dichloro-phenyl)-ethyl]-2-ethylamino-benzamide;
5-Chloro-N-(4-cyclobutyl-benzyl)-2-ethylamino-N-[2-(3-trifluoromethyl-phenyl)-ethyl]-benzamide;
5-Chloro-N-(4-cyclopentyl-benzyl)-2-ethylamino-N-[2-(3-trifluoromethyl-phenyl)-ethyl]-benzamide;
5-Chloro-N-(4-cyclobutyl-benzyl)-2-ethylamino-N-[2-(4-fluoro-3-trifluoromethyl-phenyl)-ethyl]-benzamide;
5-Chloro-N-(4-cyclopentyl-benzyl)-N-[2-(3,4-dichloro-phenyl)-ethyl]-2-ethylamino-benzamide;
5-Chloro-N-(4-cyclopentyl-benzyl)-2-ethylamino-N-[2-(4-fluoro-3-trifluoromethyl-phenyl)-ethyl]-benzamide;
N-(4-tert-Butyl -benzyl)-5-chloro-N-[2-(4-chloro-3-trifluoromethyl-pyrazol-1-yl)-ethyl]-2-methylamino-benzamide;
N-(4-tert-Butyl-benzyl)-5-chloro-2-methylamino-N-[2-(3-phenyl-pyrazol-1-yl)-ethyl]-benzamide;
N-(4-tert-Butyl-benzyl)-5-chloro-N-[2-(4-chloro-5-methyl-3-trifluoromethyl-pyrazol-1-yl)-ethyl]-2-methylamino-nicotinamide;
N-(4-tert-Butyl-benzyl)-5-chloro-N-[2-(4-chloro-3-methyl-5-trifluoromethyl-pyrazol-1-yl)-ethyl]-2-methylamino-benzamide;
N-(4-tert-Butyl-benzyl)-5-chloro-N-[2-(4-chloro-5-methyl-3-trifluoromethyl-pyrazol-1-yl)-ethyl]-2-methylamino-benzamide;
N-(4-tert-Butyl-benzyl)-5-chloro-2-methylamino-N-[2-(4-trifluoromethyl-imidazol-1-yl)-ethyl]-nicotinamide; and
a pharmaceutically acceptable salt thereof.

13. A compound of claim 1 selected from the group consisting of:
N-(4-tert-Butyl-benzyl)-5-chloro-2-methylamino-N-[2-(4-trifluoromethyl-imidazol-1-yl)-ethyl]-benzamide;
N-(4-tert-Butyl-benzyl)-5-chloro-2-methylamino-N-[2-(5-methyl-3-trifluoromethyl-pyrazol-1-yl)-ethyl]-benzamide;
N-(4-tert-Butyl-benzyl)-5-chloro-2-methylamino-N-[2-(3-trifluoromethyl-pyrazol-1-yl)-ethyl]-benzamide;
N-(4-tert-Butyl-benzyl)-5-chloro-2-methylamino-N-[2-(5-trifluoromethyl-pyrazol-1-yl)-ethyl]-benzamide;
3-Ethylamino-5-methyl-isoxazole-4-carboxylic acid (4-tert-butyl-benzyl)-[2-(3,4-dichloro-phenyl)-ethyl]-amide;
1,3-Dimethyl-5-methylamino-1H-pyrazole-4-carboxylic acid (4-tert-butyl-benzyl)-[2-(3,4-dichloro-phenyl)-ethyl]-amide;
5-Ethylamino-3-methyl-isothiazole-4-carboxylic acid (4-tert-butyl-benzyl)-[2-(3,4-dichloro-phenyl)-ethyl]-amide;
3-Methyl-5-methylamino-isothiazole-4-carboxylic acid (4-tert-butyl-benzyl)-[2-(3-trifluoromethyl-phenyl)-ethyl]-amide;
3-Methyl-5-methylamino-isothiazole-4-carboxylic acid (4-tert-butyl-benzyl)-[2-(3,4-dichloro-phenyl)-ethyl]-amide;
5-Cyclopropylamino-3-methyl-isothiazole-4-carboxylic acid (4-tert-butyl-benzyl)-[2-(3,4-dichloro-phenyl)-ethyl]-amide;
5-Cyclopropylamino-3-methyl-isothiazole-4-carboxylic acid (4-tert-butyl-benzyl)-[2-(3-trifluoromethyl-phenyl)-ethyl]-amide;
5-Isopropylamino-3-methyl-isothiazole-4-carboxylic acid (4-tert-butyl-benzyl)-[2-(3-trifluoromethyl-phenyl)-ethyl]-amide;
5-Isopropylamino-3-methyl-isothiazole-4-carboxylic acid (4-tert-butyl-benzyl)-[2-(3,4-dichloro-phenyl)-ethyl]-amide;

5-Cyclopropylamino-thiazole-4-carboxylic acid (4-tert-butyl-benzyl)-[2-(3-trifluoromethyl-phenyl)-ethyl]-amide;
2-Methylamino-thiophene-3-carboxylic acid (4-tert-butyl-benzyl)-[2-(3-trifluoromethyl-phenyl)-ethyl]-amide;
3-Methylamino-thiophene-2-carboxylic acid (4-tert-butyl-benzyl)-[2-(3-trifluoromethyl-phenyl)-ethyl]-amide;
3-Methylamino-thiophene-2-carboxylic acid (4-tert-butyl-benzyl)-[2-(3,4-dichloro-phenyl)-ethyl]-amide;
4-Methylamino-thiophene-3-carboxylic acid (4-tert-butyl-benzyl)-[2-(3-trifluoromethyl-phenyl)-ethyl]-amide;
4-Methylamino-thiophene-3-carboxylic acid (4-tert-butyl-benzyl)-[2-(3,4-dichloro-phenyl)-ethyl]-amide;
4-Acetylamino-N-(4-tert-butyl-benzyl)-N-[2-(3,4-dichloro-phenyl)-ethyl]-nicotinamide;
4-Acetylamino-N-(4-tert-butyl-benzyl)-N-[2-(4-chloro-3-trifluoromethyl-phenyl)-ethyl]-nicotinamide;
4-Acetylamino-N-(4-tert-butyl-benzyl)-N-[2-(3-trifluoromethyl-phenyl)-ethyl]-nicotinamide;
3-Amino-pyridine-2-carboxylic acid (4-tert-butyl-benzyl)-[2-(3,4-dichloro-phenyl)-ethyl]-amide;
3-Acetylamino-pyridine-2-carboxylic acid (4-tert-butyl-benzyl)-[2-(3,4-dichloro-phenyl)-ethyl]-amide;
2-Amino-N-(4-tert-butyl-benzyl)-N-[2-(4-chloro-3-trifluoromethyl-phenyl)-ethyl]-nicotinamide;
2-Amino-N-(4-tert-butyl-benzyl)-N-[2-(3-trifluoromethyl-phenyl)-ethyl]-nicotinamide;
3-Methylamino-pyridine-2-carboxylic acid (4-tert-butyl-benzyl)-[2-(3,4-dichloro-phenyl)-ethyl]-amide;
3-Amino-pyridine-2-carboxylic acid (4-tert-butyl-benzyl)-[2-(3-trifluoromethyl-phenyl)-ethyl]-amide;
3-Methylamino-pyridine-2-carboxylic acid (4-tert-butyl-benzyl)-[2-(3-trifluoromethyl-phenyl)-ethyl]-amide;
3-Amino-6-methyl-pyridine-2-carboxylic acid (4-tert-butyl-benzyl)-[2-(3,4-dichloro-phenyl)-ethyl]-amide;
6-Methyl-3-methylamino-pyridine-2-carboxylic acid (4-tert-butyl-benzyl)-[2-(3,4-dichloro-phenyl)-ethyl]-amide;
N-(4-tert-Butyl-benzyl)-N-[2-(3,4-dichloro-phenyl)-ethyl-2-ethylamino-nicotinamide;
N-(4-tert-Butyl-benzyl)-N-[2-(3,4-dichloro-phenyl)-ethyl]-2-dimethylamino-nicotinamide;
N-(4-tert-Butyl-benzyl)-N-[2-(3,4-dichloro-phenyl)-ethyl]-4-methylamino-nicotinamide;
N-(4-tert-Butyl-benzyl)-2-cyclopropylamino-N-[2-(3,4-dichloro-phenyl)-ethyl]-nicotinamide;
N-(4-tert-Butyl-benzyl)-N-[2-(3,4-dichloro-phenyl)-ethyl]-4-ethylamino-nicotinamide;
N-(4-tert-Butyl-benzyl)-5-chloro-N-[2-(3,4-dichloro-phenyl)-ethyl]-2-methylamino-nicotinamide;
5-Bromo-N-(4-tert-butyl-benzyl)-N-[2-(3,4-dichloro-phenyl)-ethyl]-2-methylamino-nicotinamide;
5-Bromo-N-(4-tert-butyl-benzyl)-N-[2-(3,4-dichloro-phenyl)-ethyl]-2-ethylamino-nicotinamide;
N-(4-tert-Butyl-benzyl)-N-[2-(3,4-dichloro-phenyl)-ethyl]-2-(2-hydroxy-ethylamino)-nicotinamide;
N-(4-tert-Butyl-benzyl)-5-chloro-N-[2-(3,4-dichloro-phenyl)-ethyl]-2-ethylamino-nicotinamide;
N-(4-tert-Butyl-benzyl)-5-chloro-2-cyclopropylamino-N-[2-(3,4-dichloro-phenyl)-ethyl]-nicotinamide;
N-(4-tert-Butyl-benzyl)-N-[2-(3,4-dichloro-phenyl)-ethyl]-5-fluoro-2-methylamino-nicotinamide;
N-(4-tert-Butyl-benzyl)-5-chloro-N-[2-(3,4-dichloro-phenyl)-ethyl]-2-(2-hydroxy-ethylamino)-nicotinamide;
3-Amino-N-(4-tert-butyl-benzyl)-N-[2-(3,4-dichloro-phenyl)-ethyl]-isonicotinamide;
3-Amino-pyrazine-2-carboxylic acid (4-tert-butyl-benzyl)-[2-(3,4-dichloro-phenyl)-ethyl]-amide;
N-(4-tert-Butyl-benzyl)-N-[2-(3,4-dichloro-phenyl)-ethyl]-3-methylamino-isonicotinamide;
3-Methylamino-pyrazine-2-carboxylic acid (4-tert-butyl-benzyl)-[2-(3,4-dichloro-phenyl)-ethyl]-amide;
N-(4-tert-Butyl-benzyl)-N-[2-(3,4-dichloro-phenyl)-ethyl]-2-ethylamino-5-fluoro-nicotinamide;
N-(4-tert-Butyl-benzyl)-2-cyclopropylamino-N-[2-(3,4-dichloro-phenyl)-ethyl]-5-fluoro-nicotinamide;
4-Amino-pyrimidine-5-carboxylic acid (4-tert-butyl-benzyl)-[2-(3,4-dichloro-phenyl)-ethyl]-amide; and
a pharmaceutically acceptable salt thereof.

14. A compound of claim 1 selected from the group consisting of:
2-Amino-N-(4-tert-butyl-benzyl)-N-[2-(3,4-dichloro-phenyl)-ethyl]-6-methyl-nicotinamide;
4-Methylamino-pyrimidine-5-carboxylic acid (4-tert-butyl-benzyl)-[2-(3,4-dichloro-phenyl)-ethyl]-amide;
N-(4-tert-Butyl-benzyl)-N-[2-(3,4-dichloro-phenyl)-ethyl]-6-methyl-2-methylamino-nicotinamide;
6-Chloro-3-methylamino-pyridine-2-carboxylic acid (4-tert-butyl-benzyl)-[2-(3,4-dichloro-phenyl)-ethyl]-amide;
5-Chloro-N-[2-(3,4-dichloro-phenyl)-ethyl]-2-methylamino-N-[4-(1,2,2,2-tetrafluoro-1-trifluoromethyl-ethyl)-benzyl]-nicotinamide;
5-Chloro-N-[2-(4-fluoro-phenyl)-ethyl]-2-methylamino-N-[4-(1,2,2,2-tetrafluoro-1-trifluoromethyl-ethyl)-benzyl]-nicotinamide;
5-Chloro-2-methylamino-N-[4-(1,2,2,2-tetrafluoro-1-trifluoromethyl-ethyl)-benzyl]-N-[2-(3-trifluoromethyl-phenyl)-ethyl]-nicotinamide;
N-(4-tert-Butyl-benzyl)-5-chloro-2-methylamino-N-[2-(3-trifluoromethyl-phenyl)-ethyl]-nicotinamide;
N-Butyl-N-(4-tert-butyl-benzyl)-5-chloro-2-methylamino-nicotinamide;
5-Chloro-2-cyclopropylamino-N-[2-(3,4-dichloro-phenyl)-ethyl]-N-[4-(1,2,2,2-tetrafluoro-1-trifluoromethyl-ethyl)-benzyl]-nicotinamide;
5-Chloro-2-cyclopropylamino-N-[2-(4-fluoro-phenyl)-ethyl]-N-[4-(1,2,2,2-tetrafluoro-1-trifluoromethyl-ethyl)-benzyl]-nicotinamide;
N-(4-tert-Butyl-benzyl)-5-chloro-2-cyclopropylamino-N-[2-(3-trifluoromethyl-phenyl)-ethyl]-nicotinamide;
5-Chloro-N-(4-cyclobutyl-benzyl)-N-[2-(3,4-dichloro-phenyl)-ethyl]-2-methylamino-nicotinamide;
5-Chloro-N-(4-cyclopentyl-benzyl)-N-[2-(3,4-dichloro-phenyl)-ethyl]-2-methylamino-nicotinamide;
5-Chloro-2-cyclopropylamino-N-[4-(1,2,2,2-tetrafluoro-1-trifluoromethyl-ethyl)-benzyl]-N-[2-(3-trifluoromethyl-phenyl)-ethyl]-nicotinamide;
5-Chloro-N-(4-cyclobutyl-benzyl)-2-cyclopropylamino-N-[2-(3,4-dichloro-phenyl)-ethyl]-nicotinamide;
5-Amino-pyrimidine-4-carboxylic acid (4-tert-butyl-benzyl)-[2-(3,4-dichloro-phenyl)-ethyl]-amide;
5-Methylamino-pyrimidine-4-carboxylic acid (4-tert-butyl-benzyl)-[2-(3,4-dichloro-phenyl)-ethyl]-amide;
N-(4-tert-Butyl-benzyl)-N-[2-(3,4-dichloro-phenyl)-ethyl]-2-methylamino-benzamide;

6-Chloro-3-methylamino-pyridine-2-carboxylic acid [2-(3,4-dichloro-phenyl)-ethyl]-[4-(1,2,2,2-tetrafluoro-1-trifluoromethyl-ethyl)-benzyl]-amide;
6-Chloro-3-methylamino-pyridine-2-carboxylic acid [2-(4-fluoro-phenyl)-ethyl]-[4-(1,2,2,2-tetrafluoro-1-trifluoromethyl-ethyl)-benzyl]-amide;
6-Chloro-3-methylamino-pyridine-2-carboxylic acid [4-(1,2,2,2-tetrafluoro-1-trifluoromethyl-ethyl)-benzyl]-[2-(3-trifluoromethyl-phenyl)-ethyl]-amide;
6-Chloro-3-methylamino-pyridine-2-carboxylic acid (4-tert-butyl-benzyl)-[2-(3-trifluoromethyl-phenyl)-ethyl]-amide;
6-Chloro-3-methylamino-pyridine-2-carboxylic acid butyl-(4-tert-butyl-benzyl)-amide;
6-Chloro-3-cyclopropylamino-pyridine-2-carboxylic acid (4-tert-butyl-benzyl)-[2-(3,4-dichloro-phenyl)-ethyl]-amide;
6-Chloro-3-cyclopropylamino-pyridine-2-carboxylic acid [2-(3,4-dichloro-phenyl)-ethyl]-[4-(1,2,2,2-tetrafluoro-1-trifluoromethyl-ethyl)-benzyl]-amide;
6-Chloro-3-cyclopropylamino-pyridine-2-carboxylic acid [2-(4-fluoro-phenyl)-ethyl]-[4-(1,2,2,2-tetrafluoro-1-trifluoromethyl-ethyl)-benzyl]-amide;
6-Chloro-3-cyclopropylamino-pyridine-2-carboxylic acid [4-(1,2,2,2-tetrafluoro-1-trifluoromethyl-ethyl)-benzyl]-[2-(3-trifluoromethyl-phenyl)-ethyl]-amide;
6-Chloro-3-methylamino-pyridazine-4-carboxylic acid (4-tert-butyl-benzyl)-[2-(3,4-dichloro-phenyl)-ethyl]-amide;
5-Fluoro-N-[2-(4-fluoro-phenyl)-ethyl]-2-methylamino-N-[4-(1,2,2,2-tetrafluoro-1-trifluoromethyl-ethyl)-benzyl]-nicotinamide;
N-(4-Cyclobutyl-benzyl)-N-[2-(3,4-dichloro-phenyl)-ethyl]-2-ethylamino-5-fluoro-nicotinamide;
6-Chloro-3-methylamino-pyridazine-4-carboxylic acid [4-(1,2,2,2-tetrafluoro-1-trifluoromethyl-ethyl)-benzyl]-[2-(3-trifluoromethyl-phenyl)-ethyl]-amide;
6-Chloro-3-methylamino-pyridazine-4-carboxylic acid (4-cyclobutyl-benzyl)-[2-(3-trifluoromethyl-phenyl)-ethyl]-amide;
5-Bromo-N-[2-(3,4-dichloro-phenyl)-ethyl]-2-methylamino-N-[4-(1,2,2,2-tetrafluoro-1-trifluoromethyl-ethyl)-benzyl]-nicotinamide;
5-Bromo-N-(4-cyclobutyl-benzyl)-N-[2-(3,4-dichloro-phenyl)-ethyl]-2-methylamino-nicotinamide;
5-Chloro-N-(4-cyclobutyl-benzyl)-2-methylamino-N-[2-(3-trifluoromethyl-phenyl)-ethyl]-nicotinamide;
6-Methoxy-3-methylamino-pyridazine-4-carboxylic acid (4-tert-butyl-benzyl)-[2-(3,4-dichloro-phenyl)-ethyl]-amide;
2-Amino-N-(4-tert-butyl-benzyl)-N-[2-(3,4-dichloro-phenyl)-ethyl]-nicotinamide;
6-Chloro-3-methylamino-pyridazine-4-carboxylic acid [2-(3,4-dichloro-phenyl)-ethyl]-[4-(1,2,2,2-tetrafluoro-1-trifluoromethyl-ethyl)-benzyl]-amide;
2-Ethylamino-5-fluoro-N-[2-(4-fluoro-phenyl)-ethyl]-N-[4-(1,2,2,2-tetrafluoro-1-trifluoromethyl-ethyl)-benzyl]-nicotinamide;
3-Methylamino-pyridazine-4-carboxylic acid (4-tert-butyl-benzyl)-[2-(3,4-dichloro-phenyl)-ethyl]-amide;
N-(4-tert-Butyl-benzyl)-N-[2-(3,4-dichloro-phenyl)-ethyl]-5-methyl-2-methylamino-nicotinamide;
5-Chloro-N-[2-(4-chloro-phenyl)-ethyl]-2-methylamino-N-[4-(1,2,2,2-tetrafluoro-1-trifluoromethyl-ethyl)-benzyl]-nicotinamide;
5-Chloro-N-(4-cyclopropyl-benzyl)-2-methylamino-N-[2-(3-trifluoromethyl-phenyl)-ethyl]-nicotinamide;
5-Chloro-N-[2-(4-chloro-phenyl)-ethyl]-N-(4-cyclopropyl-benzyl)-2-methylamino-nicotinamide;
(4-tert-Butyl-benzyl)-N-[2-(3,4-dichloro-phenyl)-ethyl]-2-ethylamino-5-methyl-nicotinamide;
5-Chloro-N-(4-cyclopropyl-benzyl)-2-ethylamino-N-[2-(3-trifluoromethyl-phenyl)-ethyl]-nicotinamide;
6-Chloro-3-methylamino-pyridine-2-carboxylic acid [2-(4-chloro-phenyl)-ethyl]-[4-(1,2,2,2-tetrafluoro-1-trifluoromethyl-ethyl)-benzyl]-amide;
6-Chloro-3-methylamino-pyridine-2-carboxylic acid (4-cyclopropyl-benzyl)-[2-(3-trifluoromethyl-phenyl)-ethyl]-amide;
6-Chloro-3-methylamino-pyridine-2-carboxylic acid [2-(4-chloro-phenyl)-ethyl]-(4-cyclopropyl-benzyl)-amide;
N-(4-tert-Butyl-benzyl)-N-[2-(3,4-dichloro-phenyl)-ethyl]-2-methylamino-5-phenyl-nicotinamide; and
a pharmaceutically acceptable salt thereof.

15. A compound of claim 1 selected from the group consisting of:
3-Amino-6-methyl-pyridine-2-carboxylic acid (4-tert-butyl-benzyl)-[2-(3-trifluoromethyl-phenyl)-ethyl]-amide;
3-Amino-6-methyl-pyrazine-2-carboxylic acid (4-tert-butyl-benzyl)-[2-(3,4-dichloro-phenyl)-ethyl]-amide;
3-Amino-6-chloro-pyrazine-2-carboxylic acid (4-tert-butyl-benzyl)-[2-(3,4-dichloro-phenyl)-ethyl]-amide;
6-Chloro-3-methylamino-pyrazine-2-carboxylic acid (4-tert-butyl-benzyl)-[2-(3,4-dichloro-phenyl)-ethyl]-amide;
6-Methyl-3-methylamino-pyrazine-2-carboxylic acid (4-tert-butyl-benzyl)-[2-(3,4-dichloro-phenyl)-ethyl]-amide;
6-Chloro-3-ethylamino-pyridine-2-carboxylic acid (4-tert-butyl-benzyl)-[2-(3,4-dichloro-phenyl)-ethyl]-amide;
6-Chloro-3-ethylamino-pyridine-2-carboxylic acid (4-tert-butyl-benzyl)-[2-(3-trifluoromethyl-phenyl)-ethyl]-amide;
N-(4-tert-Butyl-benzyl)-2-chloro-N-[2-(3,4-dichloro-phenyl)-ethyl]-5-methylamino-isonicotinamide;
N-(4-tert-Butyl-benzyl)-2-chloro-5-methylamino-N-[2-(3-trifluoromethyl-phenyl)-ethyl]-isonicotinamide;
6-Chloro-3-methylamino-pyridine-2-carboxylic acid (4-tert-butyl-benzyl)-phenethyl-amide;
6-Chloro-3-methylamino-pyridine-2-carboxylic acid [2-(3,4-dichloro-phenyl)-ethyl]-(4-(pentafluorothio)-benzyl)-amide;
N-(4-tert-Butyl-benzyl)-N-[2-(3,4-dichloro-phenyl)-ethyl]-2-methylamino-5-vinyl-nicotinamide;
2-Chloro-N-[2-(3,4-dichloro-phenyl)-ethyl]-5-methylamino-N-[4-(1,2,2,2-tetrafluoro-1-trifluoromethyl-ethyl)-benzyl]-isonicotinamide;
5-Amino-2-chloro-pyrimidine-4-carboxylic acid (4-tert-butyl-benzyl)-[2-(3,4-dichloro-phenyl)-ethyl]-amide;
2-Chloro-5-methylamino-pyrimidine-4-carboxylic acid (4-tert-butyl-benzyl)-[2-(3,4-dichloro-phenyl)-ethyl]-amide;
5-Chloro-N-[2-(3,4-dichloro-phenyl)-ethyl]-N-(4-isopropyl-benzyl)-2-methylamino-nicotinamide;
6-Chloro-3-methylamino-pyridine-2-carboxylic acid (4-cyclobutyl-benzyl)-[2-(3,4-dichloro-phenyl)-ethyl]-amide;
6-Chloro-3-methylamino-pyridine-2-carboxylic acid (4-cyclobutyl-benzyl)-[2-(3-trifluoromethyl-phenyl)-ethyl]-amide;

2-Chloro-N-(4-cyclobutyl-benzyl)-N-[2-(3,4-dichloro-phenyl)-ethyl]-5-methylamino-isonicotinamide;
2-Chloro-N-(4-cyclobutyl-benzyl)-5-methylamino-N-[2-(3-trifluoromethyl-phenyl)-ethyl]-isonicotinamide;
2-Chloro-N-[2-(4-chloro-phenyl)-ethyl]-5-methylamino-N-[4-(1,2,2,2-tetrafluoro-1-trifluoromethyl-ethyl)-benzyl]-isonicotinamide;
2-Chloro-5-methylamino-N-[4-(1,2,2,2-tetrafluoro-1-trifluoromethyl-ethyl)-benzyl]-N-[2-(3-trifluoromethyl-phenyl)-ethyl]-isonicotinamide;
5-Chloro-N-[4-(1-fluoro-cyclopropyl)-benzyl]-2-methylamino-N-[2-(3-trifluoromethyl-phenyl)-ethyl]-nicotinamide;
5-Chloro-N-[4-(1-fluoro-cyclopropyl)-benzyl]-2-methylamino-N-[2-(3-trifluoromethyl-phenyl)-ethyl]-benzamide;
5-Chloro-N-(4-isopropyl-benzyl)-2-methylamino-N-[2-(3-trifluoromethyl-phenyl)-ethyl]-nicotinamide;
5-Chloro-N-(4-isopropyl-benzyl)-2-methylamino-N-[2-(3-trifluoromethyl-phenyl)-ethyl]-benzamide;
6-Chloro-3-methylamino-pyrazine-2-carboxylic acid (4-isopropyl-benzyl)-[2-(3-trifluoromethyl-phenyl)-ethyl]-amide;
6-Chloro-3-methylamino-pyrazine-2-carboxylic acid (4-tert-butyl-benzyl)-[2-(3-trifluoromethyl-phenyl)-ethyl]-amide;
6-Chloro-3-methylamino-pyridine-2-carboxylic acid (4-isopropyl-benzyl)-[2-(3-trifluoromethyl-phenyl)-ethyl]-amide;
2-Chloro-N-(4-isopropyl-benzyl)-5-methylamino-N-[2-(3-trifluoromethyl-phenyl)-ethyl]-isonicotinamide;
5-Chloro-N-[2-(4-chloro-phenyl)-ethyl]-N-[4-(1-fluoro-cyclopropyl)-benzyl]-2-methylamino-benzamide;
5-Chloro-N-(4-isopropyl-benzyl)-2-methylamino-N-[2-(3-trifluoromethoxy-phenyl)-ethyl]-nicotinamide;
5-Chloro-N-(4-isopropyl-benzyl)-2-methylamino-N-[2-(3-trifluoromethoxy-phenyl)-ethyl]-benzamide;
5-Chloro-N-[2-(4-chloro-phenyl)-ethyl]-N-(4-isopropyl-benzyl)-2-methylamino-nicotinamide;
5-Chloro-N-[2-(4-chloro-phenyl)-ethyl]-N-(4-isopropyl-benzyl)-2-methylamino-benzamide;
6-Chloro-3-methylamino-pyridine-2-carboxylic acid (4-tert-butyl-benzyl)-(2,2-difluoro-2-phenyl-ethyl)-amide;
N-(4-tert-Butyl-benzyl)-5-chloro-N-{2-[(4-chloro-phenyl)-methyl-amino]-ethyl}-2-methylamino-nicotinamide;
N-(4-tert-Butyl-benzyl)-5-chloro-N-{2-[(4-chloro-phenyl)-methyl-amino]-ethyl}-2-methylamino-benzamide;
5-Chloro-2-methylamino-N-(4-pentafluoroethyl-benzyl)-N-[2-(3-trifluoromethyl-phenyl)-ethyl]-benzamide;
6-Chloro-3-methylamino-pyridine-2-carboxylic acid (4-pentafluoroethyl-benzyl)-[2-(3-trifluoromethyl-phenyl)-ethyl]-amide;
5-Chloro-2-methylamino-N-(4-pentafluoroethyl-benzyl)-N-[2-(3-trifluoromethoxy-phenyl)-ethyl]-benzamide;
6-Chloro-3-methylamino-pyridine-2-carboxylic acid (4-pentafluoroethyl-benzyl)-[2-(3-trifluoromethoxy-phenyl)-ethyl]-amide;
5-Chloro-N-[2-(4-chloro-phenyl)-ethyl]-2-methylamino-N-(4-pentafluoroethyl-benzyl)-benzamide;
6-Chloro-3-methylamino-pyridine-2-carboxylic acid [2-(4-chloro-phenyl)-ethyl]-(4-pentafluoroethyl-benzyl)-amide;
5-Chloro-N-[2-(3-methoxy-phenyl)-ethyl]-2-methylamino-N-(4-pentafluoroethyl-benzyl)-benzamide;
6-Chloro-3-methylamino-pyridine-2-carboxylic acid [2-(3-methoxy-phenyl)-ethyl]-(4-pentafluoroethyl-benzyl)-amide;
5-Chloro-2-methylamino-N-(4-pentafluoroethyl-benzyl)-N-(2-p-tolyl-ethyl)-benzamide;
6-Chloro-3-methylamino-pyridine-2-carboxylic acid (4-pentafluoroethyl-benzyl)-(2-p-tolyl-ethyl)-amide;
5-Chloro-N-[2-(4-fluoro-phenyl)-ethyl]-2-methylamino-N-(4-pentafluoroethyl-benzyl)-benzamide;
6-Chloro-3-methylamino-pyridine-2-carboxylic acid [2-(4-fluoro-phenyl)-ethyl]-(4-pentafluoroethyl-benzyl)-amide;
5-Chloro-N-[2-(4-fluoro-phenyl)-ethyl]-2-methylamino-N-(4-pentafluoroethyl-benzyl)-nicotinamide;
5-Chloro-N-[2-(4-chloro-phenyl)-ethyl]-2-methylamino-N-(4-pentafluoroethyl-benzyl)-nicotinamide;
5-Chloro-2-methylamino-N-(4-pentafluoroethyl-benzyl)-N-[2-(3-trifluoromethoxy-phenyl)-ethyl]-nicotinamide;
5-Chloro-N-[2-(3-methoxy-phenyl)-ethyl]-2-methylamino-N-(4-pentafluoroethyl-benzyl)-nicotinamide;
5-Chloro-2-methylamino-N-(4-pentafluoroethyl-benzyl)-N-(2-p-tolyl-ethyl)-nicotinamide; and
a pharmaceutically acceptable salt thereof.

16. A compound of claim 1 selected from the group consisting of:

N-(4-tert-Butyl-benzyl)-5-chloro-N-[2-(4-chloro-phenylamino)-ethyl]-2-methylamino-benzamide;
N-(4-tert-Butyl-benzyl)-5-chloro-2-methylamino-N-(2-naphthalen-2-yl-ethyl)-benzamide;
6-Chloro-3-methylamino-pyridine-2-carboxylic acid (4-tert-butyl-benzyl)-[2-(4-chloro-phenylamino)-ethyl]-amide;
6-Chloro-3-methylamino-pyridine-2-carboxylic acid (4-tert-butyl-benzyl)-(2-naphthalen-2-yl-ethyl)-amide;
5-Chloro-2-methylamino-N-(4-pentafluoroethyl-benzyl)-N-[2-(3-trifluoromethyl-phenyl)-ethyl]-nicotinamide;
2-Chloro-5-methylamino-N-(4-pentafluoroethyl-benzyl)-N-[2-(3-trifluoromethyl-phenyl)-ethyl]-isonicotinamide;
2-Chloro-N-[2-(4-chloro-phenyl)-ethyl]-5-methylamino-N-(4-pentafluoroethyl-benzyl)-isonicotinamide;
5-Chloro-2-ethylamino-N-(4-pentafluoroethyl-benzyl)-N-[2-(3-trifluoromethyl-phenyl)-ethyl]-benzamide;
5-Chloro-N-[2-(4-chloro-phenyl)-ethyl]-2-ethylamino-N-(4-pentafluoroethyl-benzyl)-benzamide;
6-Chloro-3-methylamino-pyrazine-2-carboxylic acid (4-cyclobutyl-benzyl)-[2-(4-fluoro-phenyl)-ethyl]-amide;
6-Chloro-3-methylamino-pyrazine-2-carboxylic acid (4-cyclobutyl-benzyl)-[2-(3-trifluoromethyl-phenyl)-ethyl]-amide;
6-Chloro-3-methylamino-pyrazine-2-carboxylic acid [2-(4-chloro-phenyl)-ethyl]-(4-cyclobutyl-benzyl)-amide;
6-Chloro-3-methylamino-pyridine-2-carboxylic acid [2-(4-chloro-phenyl)-ethyl]-(4-cyclobutyl-benzyl)-amide;
6-Chloro-3-methylamino-pyridine-2-carboxylic acid (4-cyclobutyl-benzyl)-[2-(4-fluoro-phenyl)-ethyl]-amide;
3-Amino-6-methyl-pyridine-2-carboxylic acid [2-(4-chloro-phenyl)-ethyl]-(4-cyclobutyl-benzyl)-amide;
3-Amino-6-methyl-pyridine-2-carboxylic acid (4-cyclobutyl-benzyl)-[2-(4-fluoro-phenyl)-ethyl]-amide;
3-Amino-6-methyl-pyridine-2-carboxylic acid (4-cyclobutyl-benzyl)-[2-(3-trifluoromethyl-phenyl)-ethyl]-amide;

6-Methyl-3-methylamino-pyridine-2-carboxylic acid (4-cyclobutyl-benzyl)-[2-(4-fluoro-phenyl)-ethyl]-amide;
6-Methyl-3-methylamino-pyridine-2-carboxylic acid (4-cyclobutyl-benzyl)-[2-(3-trifluoromethyl-phenyl)-ethyl]-amide;
N-(4-tert-Butyl-benzyl)-5-chloro-3-fluoro-2-methylamino-N-[2-(3-trifluoromethyl-phenyl)-ethyl]-benzamide;
N-(4-tert-Butyl-benzyl)-5-chloro-N-[2-(3,4-dichloro-phenyl)-ethyl]-3-fluoro-2-methylamino-benzamide;
2-Acetylamino-N-(4-tert-butyl-benzyl)-5-chloro-3-fluoro-N-[2-(3-trifluoromethyl-phenyl)-ethyl]-benzamide;
2-Amino-N-(4-tert-butyl-benzyl)-5-chloro-N-[2-(4-fluoro-phenyl)-ethyl]-3-iodo-benzamide;
N-(4-tert-Butyl-benzyl)-2,3-dichloro-6-methylamino-N-[2-(3-trifluoromethyl-phenyl)-ethyl]-benzamide;
6-Amino-N-(4-tert-butyl-benzyl)-2,3-dichloro-N-[2-(3-trifluoromethyl-phenyl)-ethyl]-benzamide;
N-(4-tert-Butyl-benzyl)-2,3-dichloro-6-(cyclopropanecarbonyl-amino)-N-[2-(3-trifluoromethyl-phenyl)-ethyl]-benzamide;
6-Acetylamino-N-(4-tert-butyl-benzyl)-2,3-dichloro-N-[2-(3-trifluoromethyl-phenyl)-ethyl]-benzamide;
N-(4-tert-Butyl-benzyl)-2,3-dichloro-6-propionylamino-N-[2-(3-trifluoromethyl-phenyl)-ethyl]-benzamide;
6-Amino-N-(4-tert-butyl-benzyl)-2,3-dichloro-N-[2-(3-difluoromethoxy-phenyl)-ethyl]-benzamide;
6-Acetylamino-N-(4-tert-butyl-benzyl)-2,3-dichloro-N-[2-(3-difluoromethoxy-phenyl)-ethyl]-benzamide;
N-(4-tert-Butyl-benzyl)-2,3-dichloro-N-[2-(3-difluoromethoxy-phenyl)-ethyl]-6-propionylamino-benzamide;
2-Amino-N-(4-tert-butyl-benzyl)-6-chloro-N-[2-(3-trifluoromethyl-phenyl)-ethyl]-benzamide;
2-Amino-N-(4-tert-butyl-benzyl)-6-methyl-N-[2-(3-trifluoromethyl-phenyl)-ethyl]-benzamide;
2-Acetylamino-N-(4-tert-butyl-benzyl)-6-chloro-N-[2-(3-trifluoromethyl-phenyl)-ethyl]-benzamide;
2-Acetylamino-N-(4-tert-butyl-benzyl)-6-methyl-N-[2-(3-trifluoromethyl-phenyl)-ethyl]-benzamide;
2-Amino-N-(4-tert-butyl-benzyl)-5-chloro-N-[2-(3-trifluoromethoxy-phenyl)-ethyl]-benzamide;
2-Acetylamino-N-butyl-N-(4-tert-butyl-benzyl)-5-chloro-benzamide;
2-Acetylamino-N-(4-tert-butyl-benzyl)-5-chloro-N-[2-(3-trifluoromethoxy-phenyl)-ethyl]-benzamide;
6-Amino-N-(4-tert-butyl-benzyl)-3-chloro-2-fluoro-N-[2-(3-trifluoromethyl-phenyl)-ethyl]-benzamide;
2-Amino-N-(4-tert-butyl-benzyl)-3-chloro-6-fluoro-N-[2-(3-trifluoromethyl-phenyl)-ethyl]-benzamide;
N-(4-tert-Butyl-benzyl)-2,3-dichloro-6-(2,2,2-trifluoroacetylamino)-N-[2-(3-trifluoromethyl-phenyl)-ethyl]-benzamide;
6-Acetylamino-N-(4-tert-butyl-benzyl)-3-chloro-2-fluoro-N-[2-(3-trifluoromethyl-phenyl)-ethyl]-benzamide;
2-Amino-N-(4-tert-butyl-benzyl)-5-chloro-N-[2-(2-chloro-phenyl)-ethyl]-benzamide;
2-Amino-N-(4-tert-butyl-benzyl)-5-chloro-N-[2-(3-chloro-phenyl)-ethyl]-benzamide;
2-Acetylamino-N-(4-tert-butyl-benzyl)-5-chloro-N-[2-(2-chloro-phenyl)-ethyl]-benzamide;
2-Acetylamino-N-(4-tert-butyl-benzyl)-5-chloro-N-[2-(3-chloro-phenyl)-ethyl]-benzamide;
2-Acetylamino-N-(4-tert-butyl-benzyl)-3-chloro-6-fluoro-N-[2-(3-trifluoromethyl-phenyl)-ethyl]-benzamide;
2-Amino-N-(4-tert-butyl-benzyl)-5-chloro-N-[2-(4-chloro-phenyl)-ethyl]-benzamide;
2-Amino-N-(4-tert-butyl-benzyl)-5-chloro-N-[2-(4-methoxy-phenyl)-ethyl]-benzamide;
2-Acetylamino-N-(4-tert-butyl-benzyl)-5-chloro-N-[2-(4-chloro-phenyl)-ethyl]-benzamide;
2-Acetylamino-N-(4-tert-butyl-benzyl)-5-chloro-N-[2-(4-methoxy-phenyl)-ethyl]-benzamide;
N-(4-tert-Butyl-benzyl)-3-chloro-6-fluoro-2-methylamino-N-[2-(3-trifluoromethyl-phenyl)-ethyl]-benzamide;
2-Amino-N-(4-tert-butyl-benzyl)-3,5-dichloro-6-fluoro-N-[2-(3-trifluoromethyl-phenyl)-ethyl]-benzamide;
2-Acetylamino-5-chloro-N-[(R)-2-(4-chloro-phenyl)-2-hydroxy-ethyl]-N-(4-cyclopropyl-benzyl)-benzamide;
2-Acetylamino-N-(4-tert-butyl-benzyl)-3,5-dichloro-6-fluoro-N-[2-(3-trifluoromethyl-phenyl)-ethyl]-benzamide;
2-Amino-3,5-dichloro-N-[(R)-2-(4-chloro-phenyl)-2-hydroxy-ethyl]-N-(4-cyclopropyl-benzyl)-6-fluoro-benzamide;
6-Acetylamino-2,3-dichloro-N-[(R)-2-(4-chloro-phenyl)-2-hydroxy-ethyl]-N-(4-cyclopropyl-benzyl)-benzamide;
2-Acetylamino-3,5-dichloro-N-[(R)-2-(4-chloro-phenyl)-2-hydroxy-ethyl]-N-(4-cyclopropyl-benzyl)-6-fluoro-benzamide; and
a pharmaceutically acceptable salt thereof.

17. A compound of claim 1 selected from the group consisting of:
2-Acetylamino-5-chloro-N-(4-cyclopropyl-benzyl)—N-[2-(3-trifluoromethoxy-phenyl)-ethyl]-benzamide;
2-Acetylamino-5-chloro-N-(4-cyclopropyl-benzyl)-N-[2-(3-trifluoromethyl-phenyl)-ethyl]-benzamide;
2-Amino-3,5-dichloro-N-(4-cyclopropyl-benzyl)-6-fluoro-N-[2-(3-trifluoromethoxy-phenyl)-ethyl]-benzamide;
2-Amino-3,5-dichloro-N-(4-cyclopropyl-benzyl)-6-fluoro-N-[2-(3-trifluoromethyl-phenyl)-ethyl]-benzamide;
6-Acetylamino-2,3-dichloro-N-(4-cyclopropyl-benzyl)-N-[2-(3-trifluoromethoxy-phenyl)-ethyl]-benzamide;
6-Acetylamino-2,3-dichloro-N-(4-cyclopropyl-benzyl)-N-[2-(3-trifluoromethyl-phenyl)-ethyl]-benzamide;
2-Amino-3,5-dichloro-N-(2-chloro-4-cyclopropyl-benzyl)-6-fluoro-N-[2-(3-trifluoromethyl-phenyl)-ethyl]-benzamide;
2-Acetylamino-3,5-dichloro-N-(2-chloro-4-cyclopropyl-benzyl)-6-fluoro-N-[2-(3-trifluoromethyl-phenyl)-ethyl]-benzamide;
2-Acetylamino-3,5-dichloro-N-(4-cyclopropyl-benzyl)-6-fluoro-N-[2-(3-trifluoromethoxy-phenyl)-ethyl]-benzamide;
2-Acetylamino-3,5-dichloro-N-(4-cyclopropyl-benzyl)-6-fluoro-N-[2-(3-trifluoromethyl-phenyl)-ethyl]-benzamide;
2-Amino-5-chloro-N-(2-chloro-4-cyclopropyl-benzyl)-N-[2-(3-trifluoromethyl-phenyl)-ethyl]-benzamide;
2-Acetylamino-5-chloro-N-(2-chloro-4-cyclopropyl-benzyl)-N-[2-(3-trifluoromethyl-phenyl)-ethyl]-benzamide;
5-Chloro-N-(4-cyclopropyl-benzyl)-2-methylamino-N-[2-(3-trifluoromethyl-phenyl)-ethyl]-benzamide;

5-Chloro-2-(cyanomethyl-amino)-N-(4-cyclopropyl-benzyl)-N-[2-(3-trifluoromethoxy-phenyl)-ethyl]-benzamide;
5-Chloro-2-(cyanomethyl-amino)-N-(4-cyclopropyl-benzyl)-N-[2-(3-trifluoromethyl-phenyl)-ethyl]-benzamide;
2,3-Dichloro-6-(cyanomethyl-amino)-N-(4-cyclopropyl-benzyl)-N-[2-(3-trifluoromethoxy-phenyl)-ethyl]-benzamide;
2,3-Dichloro-N-(4-cyclopropyl-benzyl)-6-methylamino-N-[2-(3-trifluoromethoxy-phenyl)-ethyl]-benzamide;
2,3-Dichloro-6-(cyanomethyl-amino)-N-(4-cyclopropyl-benzyl)-N-[2-(3-trifluoromethyl-phenyl)-ethyl]-benzamide;
2,3-Dichloro-N-(4-cyclopropyl-benzyl)-6-methylamino-N-[2-(3-trifluoromethyl-phenyl)-ethyl]-benzamide;
5-Chloro-N-(4-cyclopropyl-benzyl)-2-ethylamino-N-[2-(3-trifluoromethyl-phenyl)-ethyl]-benzamide;
5-Chloro-N-(4-cyclopropyl-benzyl)-2-ethylamino-N-[2-(3-trifluoromethoxy-phenyl)-ethyl]-benzamide;
N-(4-tert-Butyl-benzyl)-5-chloro-2-ethylamino-N-[2-(3-trifluoromethoxy-phenyl)-ethyl]-benzamide;
5-Chloro-N-(4-cyclopropyl-2-fluoro-benzyl)-2-ethylamino-N-[2-(3-trifluoromethyl-phenyl)-ethyl]-benzamide;
5-Chloro-N-(4-cyclopropyl-3-fluoro-benzyl)-2-ethylamino-N-[2-(3-trifluoromethyl-phenyl)-ethyl]-benzamide;
3,5-Dichloro-N-(4-cyclopropyl-benzyl)-2-fluoro-6-methylamino-N-[2-(3-trifluoromethyl-phenyl)-ethyl]-benzamide;
2-Acetylamino-3,5-dichloro-N-(4-cyclopropyl-benzyl)-N-[2-(3-trifluoromethoxy-phenyl)-ethyl]-benzamide;
3,5-Dichloro-N-(4-cyclopropyl-benzyl)-2-methylamino-N-[2-(3-trifluoromethoxy-phenyl)-ethyl]-benzamide;
3,5-Dichloro-N-(4-cyclopropyl-benzyl)-2-ethylamino-N-[2-(3-trifluoromethoxy-phenyl)-ethyl]-benzamide;
3,5-Dichloro-2-(cyanomethyl-amino)-N-(4-cyclopropyl-benzyl)-N-[2-(3-trifluoromethoxy-phenyl)-ethyl]-benzamide;
3,5-Dichloro-2-(cyanomethyl-amino)-N-(4-cyclopropyl-benzyl)-6-fluoro-N-[2-(3-trifluoromethyl-phenyl)-ethyl]-benzamide;
5-Chloro-N-[2-(4-chloro-phenyl)-ethyl]-N-(4-cyclopropyl-benzyl)-2-methylamino-benzamide;
5-Chloro-N-(4-cyclopropyl-benzyl)-N-[2-(4-fluoro-phenyl)-ethyl]-2-methylamino-benzamide;
(2-{(4-tert-Butyl-benzyl)-[2-(3-trifluoromethoxy-phenyl)-ethyl]-carbamoyl}-4-chloro-phenylamino)-acetic acid ethyl ester;
5-Chloro-N-[2-(4-chloro-phenyl)-ethyl]-N-(4-cyclopropyl-benzyl)-2-ethylamino-benzamide;
5-Chloro-N-[2-(4-chloro-phenyl)-ethyl]-2-(cyanomethyl-amino)-N-(4-cyclopropyl-benzyl)-benzamide;
5-Chloro-N-[2-(4-chloro-phenyl)-ethyl]-2-methylamino-N-[4-(1,2,2,2-tetrafluoro-1-trifluoromethyl-ethyl)-benzyl]-benzamide;
N-(4-tert-Butyl-benzyl)-5-chloro-2-(cyanomethyl-amino)-N-[2-(3-trifluoromethoxy-phenyl)-ethyl]-benzamide;
N-(4-tert-Butyl-benzyl)-5-chloro-2-(cyanomethyl-amino)-N-[2-(3-trifluoromethoxy-phenyl)-ethyl]-benzamide;
5-Chloro-2-methylamino-N-(4-trifluoromethoxy-benzyl)-N-[2-(3-trifluoromethyl-phenyl)-ethyl]-benzamide;
5-Chloro-2-ethylamino-N-(4-trifluoromethoxy-benzyl)-N-[2-(3-trifluoromethyl-phenyl)-ethyl]-benzamide;
5-Chloro-N-[2-(4-chloro-phenyl)-ethyl]-2-ethylamino-N-[4-(1,2,2,2-tetrafluoro-1-trifluoromethyl-ethyl)-benzyl]-benzamide;
5-Chloro-N-[2-(4-chloro-phenyl)-ethyl]-2-(cyanomethyl-amino)-N-[4-(1,2,2,2-tetrafluoro-1-trifluoromethyl-ethyl)-benzyl]-benzamide;
5-Chloro-2-(cyanomethyl-amino)-N-(4-trifluoromethoxy-benzyl)-N-[2-(3-trifluoromethyl-phenyl)-ethyl]-benzamide;
5-Chloro-N-[2-(4-fluoro-phenyl)-ethyl]-2-methylamino-N-(4-trifluoromethoxy-benzyl)-benzamide;
5-Chloro-2-ethylamino-N-[2-(4-fluoro-phenyl)-ethyl]-N-(4-trifluoromethoxy-benzyl)-benzamide;
5-Chloro-2-(cyanomethyl-amino)-N-[2-(4-fluoro-phenyl)-ethyl]-N-(4-trifluoromethoxy-benzyl)-benzamide;
{4-Chloro-2-[[2-(4-fluoro-phenyl)-ethyl]-(4-trifluoromethoxy-benzyl)-carbamoyl]-phenylamino}-acetic acid ethyl ester;
{4-Chloro-2-[[2-(4-fluoro-phenyl)-ethyl]-(4-trifluoromethoxy-benzyl)-carbamoyl]-phenylamino}-acetic acid;
5-Chloro-N-(3-chloro-4-trifluoromethoxy-benzyl)-N-[2-(4-fluoro-phenyl)-ethyl]-2-methylamino-benzamide;
5-Chloro-2-(cyanomethyl-amino)-N-(4-cyclobutyl-benzyl)-N-[2-(3-trifluoromethyl-phenyl)-ethyl]-benzamide;
5-Chloro-N-(3-chloro-4-trifluoromethoxy-benzyl)-2-ethylamino-N-[2-(4-fluoro-phenyl)-ethyl]-benzamide;
5-Chloro-N-(3-chloro-4-trifluoromethoxy-benzyl)-2-(cyanomethyl-amino)-N-[2-(4-fluoro-phenyl)-ethyl]-benzamide;
5-Chloro-N-[2-(4-chloro-phenyl)-ethyl]-2-methylamino-N-(4-trifluoromethoxy-benzyl)-benzamide;
5-Chloro-N-[2-(4-chloro-phenyl)-ethyl]-2-ethylamino-N-(4-trifluoromethoxy-benzyl)-benzamide;
5-Chloro-N-(4-cyclobutyl-benzyl)-2-methylamino-N-[2-(3-trifluoromethyl-phenyl)-ethyl]-benzamide;
5-Chloro-N-[2-(4-chloro-phenyl)-ethyl]-2-(cyanomethyl-amino)-N-(4-trifluoromethoxy-benzyl)-benzamide;
5-Chloro-N-[4-(1-methoxy-cyclopropyl)-benzyl]-2-methylamino-N-[2-(3-trifluoromethoxy-phenyl)-ethyl]-benzamide;
5-Chloro-2-ethylamino-N-[4-(1-methoxy-cyclopropyl)-benzyl]-N-[2-(3-trifluoromethoxy-phenyl)-ethyl]-benzamide;
5-Chloro-2-(cyanomethyl-amino)-N-[4-(1-methoxy-cyclopropyl)-benzyl]-N-[2-(3-trifluoromethoxy-phenyl)-ethyl]-benzamide;
5-Chloro-N-(4-cyclobutyl-benzyl)-2-methylamino-N-[2-(3-trifluoromethoxy-phenyl)-ethyl]-benzamide;
5-Chloro-N-(4-cyclobutyl-benzyl)-2-ethylamino-N-[2-(3-trifluoromethoxy-phenyl)-ethyl]-benzamide;
5-Chloro-2-(cyanomethyl-amino)-N-(4-cyclobutyl-benzyl)-N-[2-(3-trifluoromethoxy-phenyl)-ethyl]-benzamide;
N-(4-Benzyloxy-benzyl)-5-chloro-2-methylamino-N-[2-(3-trifluoromethyl-phenyl)-ethyl]-benzamide;
[4-({(5-Chloro-2-methylamino-benzoyl)-[2-(3-trifluoromethyl-phenyl)-ethyl]-amino}-methyl)-phenoxy]-acetic acid methyl ester;
N-(4-tert-Butyl-benzyl)-2,3-dichloro-N-[2-(4-chloro-phenyl)-ethyl]-6-methylamino-benzamide; and
a pharmaceutically acceptable salt thereof.
18. A compound of claim 1 selected from the group consisting of:

2,3-Dichloro-N-[2-(4-chloro-phenyl)-ethyl]-6-methylamino-N-[4-(1,2,2,2-tetrafluoro-1-trifluoromethyl-ethyl)-benzyl]-benzamide;
N-(4-tert-Butyl-benzyl)-2,3-dichloro-6-methylamino-N-[2-(3-trifluoromethoxy-phenyl)-ethyl]-benzamide;
N-(4-tert-Butyl-benzyl)-2,3-dichloro-N-[2-(4-fluoro-phenyl)-ethyl]-6-methylamino-benzamide;
5-Chloro-N-[4-(4-cyano-benzyloxy)-benzyl]-2-methylamino-N-[2-(3-trifluoromethyl-phenyl)-ethyl]-benzamide;
5-Chloro-N-[4-(4-fluoro-benzyloxy)-benzyl]-2-methylamino-N-[2-(3-trifluoromethyl-phenyl)-ethyl]-benzamide;
2,3-Dichloro-N-[4-(1-methoxy-cyclopropyl)-benzyl]-6-methylamino-N-[2-(3-trifluoromethyl-phenyl)-ethyl]-benzamide;
5-Chloro-N-[2-(4-chloro-phenyl)-ethyl]-N-[4-(1-methoxy-cyclopropyl)-benzyl]-2-methylamino-benzamide;
2,3-Dichloro-N-[2-(4-chloro-phenyl)-ethyl]-N-[4-(1-methoxy-cyclopropyl)-benzyl]-6-methylamino-benzamide;
6-Chloro-3-methylamino-pyridine-2-carboxylic acid (4-tert-butyl-benzyl)-[2-(3-trifluoromethoxy-phenyl)-ethyl]-amide;
N-(4-tert-Butoxy-benzyl)-2,3-dichloro-N-[2-(4-chloro-phenyl)-ethyl]-6-methylamino-benzamide;
N-(4-tert-Butoxy-benzyl)-5-chloro-N-[2-(4-chloro-phenyl)-ethyl]-2-methylamino-benzamide;
5-Chloro-N-[2-(4-chloro-phenyl)-ethyl]-2-methylamino-N-(4-trifluoromethyl-benzyl)-benzamide;
2,3-Dichloro-N-[2-(4-chloro-phenyl)-ethyl]-6-methylamino-N-(4-trifluoromethyl-benzyl)-benzamide;
5-Chloro-N-[2-(4-chloro-phenyl)-ethyl]-2-methylamino-N-[4-(1,1,2,2-tetrafluoro-ethoxy)-benzyl]-benzamide;
5-Chloro-N-[2-(4-chloro-phenyl)-ethyl]-2-methylamino-N-(4-phenoxy-benzyl)-benzamide;
2,3-Dichloro-N-[2-(4-chloro-phenyl)-ethyl]-6-methylamino-N-[4-(1,1,2,2-tetrafluoro-ethoxy)-benzyl]-benzamide;
2,3-Dichloro-N-[2-(4-chloro-phenyl)-ethyl]-6-methylamino-N-(4-phenoxy-benzyl)-benzamide;
5-Chloro-2-methylamino-N-[4-(3,3,3-trifluoro-2-hydroxy-propoxy)-benzyl]-N-[2-(3-trifluoromethyl-phenyl)-ethyl]-benzamide;
Methanesulfonic acid 4-({(5-chloro-2-methylamino-benzoyl)-[2-(3-trifluoromethyl-phenyl)-ethyl]-amino}-methyl)-phenyl ester;
N-(4-tert-Butoxy-benzyl)-5-chloro-N-[2-(4-chloro-phenyl)-ethyl]-2-ethylamino-benzamide;
N-(4-tert-Butoxy-benzyl)-5-chloro-N-[2-(4-chloro-phenyl)-ethyl]-2-methylamino-nicotinamide;
6-Chloro-3-methylamino-pyridine-2-carboxylic acid (4-tert-butoxy-benzyl)-[2-(4-chloro-phenyl)-ethyl]-amide;
N-(4-tert-Butoxy-benzyl)-5-chloro-2-methylamino-N-[2-(3-trifluoromethyl-phenyl)-ethyl]-benzamide;
6-Chloro-3-methylamino-pyridine-2-carboxylic acid (4-tert-butoxy-benzyl)-[2-(3-trifluoromethyl-phenyl)-ethyl]-amide;
N-(4-tert-Butoxy-benzyl)-5-chloro-2-methylamino-N-[2-(3-trifluoromethyl-phenyl)-ethyl]-nicotinamide;
5-Chloro-N-(4-cyclopropylmethoxy-benzyl)-2-methylamino-N-[2-(3-trifluoromethyl-phenyl)-ethyl]-benzamide;
N-(4-tert-Butoxy-benzyl)-5-chloro-2-methylamino-N-[2-(3-trifluoromethoxy-phenyl)-ethyl]-benzamide;
6-Chloro-3-methylamino-pyridine-2-carboxylic acid (4-tert-butoxy-benzyl)-[2-(3-trifluoromethoxy-phenyl)-ethyl]-amide;
N-(4-tert-Butoxy-benzyl)-5-chloro-N-[2-(4-fluoro-phenyl)-ethyl]-2-methylamino-benzamide;
6-Chloro-3-methylamino-pyridine-2-carboxylic acid (4-tert-butoxy-benzyl)-[2-(4-fluoro-phenyl)-ethyl]-amide;
N-(4-tert-Butoxy-benzyl)-5-chloro-N-[2-(4-fluoro-phenyl)-ethyl]-2-methylamino-nicotinamide;
N-(4-tert-Butoxy-benzyl)-5-chloro-2-methylamino-N-[2-(3-trifluoromethoxy-phenyl)-ethyl]-nicotinamide;
N-(4-tert-Butyl-benzyl)-5-chloro-2-ethylamino-N-[2-(4-fluoro-phenyl)-ethyl]-benzamide;
N-(4-tert-Butyl-benzyl)-5-chloro-N-[2-(4-chloro-phenyl)-ethyl]-2-ethylamino-benzamide;
2-Amino-N-(4-tert-butyl-benzyl)-3,5-dichloro-N-[2-(3-trifluoromethyl-phenyl)-ethyl]-benzamide;
2-Amino-N-(4-tert-butyl-benzyl)-3,5-dimethyl-N-[2-(3-trifluoromethyl-phenyl)-ethyl]-benzamide;
2-Amino-3,5-dibromo-N-(4-tert-butyl-benzyl)-N-[2-(3-trifluoromethyl-phenyl)-ethyl]-benzamide;
2-Amino-N-(4-tert-butyl-benzyl)-5-methyl-N-[2-(3-trifluoromethyl-phenyl)-ethyl]-benzamide;
N-(4-tert-Butyl-benzyl)-2-methylamino-N-[2-(3-trifluoromethyl-phenyl)-ethyl]-benzamide;
2-Amino-N-(4-tert-butyl-benzyl)-5-iodo-N-[2-(3-trifluoromethyl-phenyl)-ethyl]-benzamide;
2-Amino-5-bromo-N-(4-tert-butyl-benzyl)-N-[2-(3-trifluoromethyl-phenyl)-ethyl]-benzamide;
3,5-Dibromo-N-(4-tert-butyl-benzyl)-2-methylamino-N-[2-(3-trifluoromethyl-phenyl)-ethyl]-benzamide;
2-Amino-3-bromo-N-(4-tert-butyl-benzyl)-5-iodo-N-[2-(3-trifluoromethyl-phenyl)-ethyl]-benzamide;
2-Amino-5-bromo-N-(4-tert-butyl-benzyl)-3-chloro-N-[2-(3-trifluoromethyl-phenyl)-ethyl]-benzamide;
2-Amino-N-(4-tert-butyl-benzyl)-3-chloro-5-iodo-N-[2-(3-trifluoromethyl-phenyl)-ethyl]-benzamide;
N-(4-tert-Butyl-benzyl)-N-[2-(3-fluoro-4-trifluoromethyl-phenyl)-ethyl]-2-methylamino-benzamide;
N-(4-tert-Butyl-benzyl)-N-[2-(2-fluoro-3-trifluoromethyl-phenyl)-ethyl]-2-methylamino-benzamide;
N-(4-tert-Butyl-benzyl)-N-[2-(3-chloro-2-fluoro-phenyl)-ethyl]-2-methylamino-benzamide;
N-(4-tert-Butyl-benzyl)-N-[2-(3-chloro-4-fluoro-phenyl)-ethyl]-2-methylamino-benzamide;
N-(4-tert-Butyl-benzyl)-N-[2-(3-difluoromethoxy-phenyl)-ethyl]-2-methylamino-benzamide;
N-(4-tert-Butyl-benzyl)-N-[2-(4-chloro-phenyl)-ethyl]-2-methylamino-benzamide;
N-(4-tert-Butyl-benzyl)-N-[2-(4-chloro-3-fluoro-phenyl)-ethyl]-2-methylamino-benzamide;
N-(4-tert-Butyl-benzyl)-2-methylamino-N-[2-(3-trifluoromethoxy-phenyl)-ethyl]-benzamide;
N-(4-tert-Butyl-benzyl)-5-chloro-2-ethylamino-N-[2-(3-trifluoromethyl-phenyl)-ethyl]-benzamide;
N-(4-tert-Butyl-benzyl)-5-chloro-2-methylamino-N-[2-(3-trifluoromethyl-phenyl)-ethyl]-benzamide;
2-Amino-N-(4-tert-butyl-benzyl)-5-chloro-N-[2-(3-trifluoromethyl-phenyl)-ethyl]-benzamide;
N-(4-tert-Butyl-benzyl)-2-(cyanomethyl-amino)-N-[2-(3-trifluoromethyl-phenyl)-ethyl]-benzamide
N-(4-tert-Butyl-benzyl)-5-chloro-N-[2-(3-chloro-4-fluoro-phenyl)-ethyl]-2-methylamino-benzamide;
N-(4-tert-Butyl-benzyl)-5-chloro-N-[2-(3,4-dichloro-phenyl)-ethyl]-2-methylamino-benzamide;

N-(4-tert-Butyl-benzyl)-5-chloro-N-[2-(3-difluoromethoxy-phenyl)-ethyl]-2-methylamino-benzamide;

N-(4-tert-Butyl-benzyl)-5-chloro-N-[2-(4-chloro-phenyl)-ethyl]-2-methylamino-benzamide;

N-(4-tert-Butyl-benzyl)-5-chloro-2-(cyclopropylmethylamino)-N-[2-(3-trifluoromethyl-phenyl)-ethyl]-benzamide;

(2-{(4-tert-Butyl-benzyl)-[2-(3-trifluoromethyl-phenyl)-ethyl]-carbamoyl}-4-chloro-phenyl)-carbamic acid methyl ester;

N-(4-tert-Butyl-benzyl)-5-chloro-2-isopropylamino-N-[2-(3-trifluoromethyl-phenyl)-ethyl]-benzamide;

N-(4-tert-Butyl-benzyl)-3-chloro-2-fluoro-6-methylamino-N-[2-(3-trifluoromethyl-phenyl)-ethyl]-benzamide;

2-Amino-5-chloro-N-[2-(3-trifluoromethyl-phenyl)-ethyl]-N-(4-trimethylsilanyl-benzyl)-benzamide;

2-Amino-5-chloro-N-[2-(4-chloro-phenyl)-ethyl]-N-(4-trimethylsilanyl-benzyl)-benzamide;

2-Amino-5-chloro-N-[2-(4-fluoro-phenyl)-ethyl]-N-(4-trimethylsilanyl-benzyl)-benzamide;

2-Amino-5-chloro-N-[2-(3,4-dichloro-phenyl)-ethyl]-N-(4-trimethylsilanyl-benzyl)-benzamide;

N-Butyl-N-(4-tert-butyl-benzyl)-2-methylamino-benzamide;

N-(4-tert-Butyl-benzyl)-2,3-dichloro-6-methanesulfonylamino-N-[2-(3-trifluoromethyl-phenyl)-ethyl]-benzamide;

N-(4-tert-Butyl-benzyl)-5-chloro-2-methanesulfonylamino-N-[2-(3-trifluoromethyl-phenyl)-ethyl]-benzamide; and a pharmaceutically acceptable salt thereof.

19. A compound of claim 1 selected from the group consisting of:

N-(4-tert-Butyl-benzyl)-5-chloro-2-methylamino-N-[2-(3-trifluoromethyl-phenyl)-ethyl]-nicotinamide;

N-(4-tert-Butyl-benzyl)-2-chloro-5-methylamino-N-[2-(3-trifluoromethyl-phenyl)-ethyl]-isonicotinamide;

5-Chloro-N-[2-(4-chloro-phenyl)-ethyl]-2-methylamino-N-[4-(1,2,2,2-tetrafluoro-1-trifluoromethyl-ethyl)-benzyl]-benzamide;

5-Chloro-N-[2-(4-chloro-phenyl)-ethyl]-2-ethylamino-N-[4-(1,2,2,2-tetrafluoro-1-trifluoromethyl-ethyl)-benzyl]-benzamide;

N-(4-tert-Butyl-benzyl)-5-chloro-2-methylamino-N-[2-(3-trifluoromethyl-phenyl)-ethyl]-benzamide; and a pharmaceutically acceptable salt thereof.

20. A compound of selected from the group consisting of:

N-(4-tert-Butyl-benzyl)-N-[2-(3,4-dichloro-phenyl)-ethyl]-2-((R)-2-hydroxymethyl-pyrrolidin-1-yl)-nicotinamide;

N-(4-tert-Butyl-benzyl)-N-[2-(3,4-dichloro-phenyl)-ethyl]-2-pyrrolidin-1-yl-nicotinamide;

2-Azetidin-1-yl-N-(4-tert-butyl-benzyl)-N-[2-(3,4-dichloro-phenyl)-ethyl]-nicotinamide;

5-Chloro-2-methylamino-N-(4-methyl-benzyl)-N-[2-(3-trifluoromethyl-phenyl)-ethyl]-benzamide;

5-Chloro-N-(4-ethyl-benzyl)-2-methylamino-N-[2-(3-trifluoromethyl-phenyl)-ethyl]-benzamide;

5-Chloro-N-(4-ethyl-benzyl)-2-methylamino-N-[2-(3-trifluoromethyl-phenyl)-ethyl]-nicotinamide;

N-(4-tert-Butyl-benzyl)-5-chloro-2-methylamino-N-(2-phenoxy-ethyl)-benzamide;

6-Chloro-3-methylamino-pyridine-2-carboxylic acid (4-tert-butyl-benzyl)-(2-phenoxy-ethyl)-amide; and a pharmaceutically acceptable salt thereof.

* * * * *

UNITED STATES PATENT AND TRADEMARK OFFICE
CERTIFICATE OF CORRECTION

PATENT NO. : 7,678,818 B2  Page 1 of 1
APPLICATION NO. : 11/655538
DATED : March 16, 2010
INVENTOR(S) : Conte et al.

It is certified that error appears in the above-identified patent and that said Letters Patent is hereby corrected as shown below:

Claim 1, column 87, line 19, delete "phenyl" and insert -- phenyl; --

Claim 12, column 90, line 11, delete "N-(4-tert-Butyl   -benzyl)" and insert -- N-(4-tert-Butyl-benzyl) --

Claim 20, column 104, line 16, delete "A compound of selected" and insert -- A compound selected --

Signed and Sealed this

Fifteenth Day of June, 2010

David J. Kappos
*Director of the United States Patent and Trademark Office*